(12) United States Patent
Kannicht et al.

(10) Patent No.: US 11,738,069 B2
(45) Date of Patent: *Aug. 29, 2023

(54) POLYPEPTIDES MODULATING SIGLEC DEPENDENT IMMUNE RESPONSES

(71) Applicant: OCTAPHARMA AG, Lachen (CH)

(72) Inventors: Christoph Kannicht, Berlin (DE); Stefan Winge, Arsta (SE); Guido Kohla, Berlin (DE); Barbara Solecka-Witulska, Berlin (DE)

(73) Assignee: OCTAPHARMA AG, Lachen (CH)

( * ) Notice: Subject to any disclaimer, the term of this patent is extended or adjusted under 35 U.S.C. 154(b) by 151 days.

This patent is subject to a terminal disclaimer.

(21) Appl. No.: 17/326,709

(22) Filed: May 21, 2021

(65) Prior Publication Data

US 2021/0275644 A1    Sep. 9, 2021

Related U.S. Application Data

(62) Division of application No. 16/302,447, filed as application No. PCT/EP2017/062295 on May 22, 2017, now Pat. No. 11,013,789.

(30) Foreign Application Priority Data

May 20, 2016   (EP) .................................. 16170690

(51) Int. Cl.
| | | |
|---|---|---|
| *A61K 38/37* | (2006.01) | |
| *C07K 14/745* | (2006.01) | |
| *C07K 14/755* | (2006.01) | |
| *A61P 7/04* | (2006.01) | |
| *C12N 15/62* | (2006.01) | |
| *A61K 38/00* | (2006.01) | |

(52) U.S. Cl.
CPC .............. *A61K 38/37* (2013.01); *A61P 7/04* (2018.01); *C07K 14/745* (2013.01); *C07K 14/755* (2013.01); *C12N 15/62* (2013.01); *A61K 38/00* (2013.01); *C07K 2319/00* (2013.01); *C07K 2319/02* (2013.01); *C07K 2319/20* (2013.01); *C07K 2319/31* (2013.01); *C07K 2319/35* (2013.01)

(58) Field of Classification Search
CPC ......... A61K 38/37; A61P 7/04; C07K 14/745; C07K 14/755
See application file for complete search history.

(56) References Cited

U.S. PATENT DOCUMENTS

2016/0279252 A1    9/2016   Aswad

FOREIGN PATENT DOCUMENTS

| CN | 105451774 | 3/2016 |
|---|---|---|
| RU | 2 328 505 | 1/2006 |
| WO | 2013/120939 | 8/2013 |
| WO | 2014/179184 | 11/2014 |

OTHER PUBLICATIONS

Pegon et al., "Factor VIII and von Willebrand factor are ligands for the carbohydrate-receptor Siglec-5", Haematologica 97(12): 1855-1863 (2012).
Lai et al., "To clear or to fear: An innate perspective on factor VIII immunity", Cellular Immunology, 301: 82-89 (2016).
Solecka et al., "Site-specific analysis of von Willebrand factor O-glycosylation", Journal of Thrombosis and Haemostasis, 14(4): 733-746 (2016).
Canis et al., "The plasma von Willebrand factor O-glycome comprises a surprising variety of suuctures including ABH antigens and disialosyl motifs", Journal of Thrombosis and Haemostasis, 8(1): 137-145 (2010).
Lenting et al., "von Willebrand factor: the old, the new and the unknown", Journal of Thrombosis and Haemostasis, 10(12): 2428-2437 (2012).
International Search Report and Written Opinion of the International Searching Authority, dated Aug. 16, 2017 in corresponding International Patent Application No. PCT/EP2017/062295.

*Primary Examiner* — Jeanette M Lieb
(74) *Attorney, Agent, or Firm* — Wenderoth, Lind & Ponack, L.L.P.

(57) ABSTRACT

The invention relates to a glycosylated polypeptide comprising an amino acid sequence being identical or homologous to at least a fragment of a mammalian, preferably a human protein, wherein said glycosylated polypeptide contains one or more sialylated O-glycans and wherein the glycosylated polypeptide shows an increased binding affinity to one or more SIGLECs, selected from SIG-5, SIG-7, SIG-8, and SIG-9 compared to the mammalian protein or fragment thereof. The invention further relates to composition comprising a first and a second polypeptide, wherein the first polypeptide is a glycosylated polypeptide containing one or more sialylated O-glycans and the second polypeptide contains an amino acid sequence homologous or identical to a second mammalian, in particular human protein, wherein compared to the second polypeptide the composition has an increased binding affinity to a SIGLEC selected from to one or more SIGLECs, selected from SIG-5, SIG-7, SIG-8, and SIG-9.

25 Claims, 17 Drawing Sheets
Specification includes a Sequence Listing.

|       | SIGLEC 5 | SIGLEC 7 | SIGLEC 8 | SIGLEC 9 |
|-------|----------|----------|----------|----------|
| Seq11 | 0.494    | 0.371    | 1.027    | 0.591    |
| Seq12 | 0.140    | 0.005    | 0.015    | 0.041    |

Estimated KD values based on Scatchard plots expressed in µM

Fig. 14

POLYPEPTIDES MODULATING SIGLEC DEPENDENT IMMUNE RESPONSES

SEQUENCE LISTING

A sequence listing in electronic (ASCII text file) format is filed with this application and incorporated herein by reference. The name of the ASCII text file is "2018_1966A.txt"; the file was created on Dec. 16, 2020; the size of the file is 61 KB.

FIELD OF THE INVENTION

The present invention relates to glycosylated polypeptides based on a mammalian protein exhibiting reduced immune response or increased immune tolerance due to modulated SIGLEC binding and methods of treatment using the glycosylated polypeptide. The invention further relates to protein complexes exhibiting reduced immune response or increased immune tolerance due to modulated SIGLEC binding and methods of treatment using the protein complexes.

BACKGROUND OF THE INVENTION

Hemophilia is a group of hereditary genetic disorders that impair the body's ability to control blood clotting or coagulation. In its most common form, Hemophilia A, clotting factor VIII (FVIII) is deficient, Hemophilia A occurs in about 1 in 5,000-10,000 male births. The FVIII protein is an essential cofactor in blood coagulation with multifunctional properties. The deficiency of FVIII can be treated with plasma-derived concentrates of FVIII or with recombinantly produced FVIII. The treatment with FVIII concentrates has led to a normalized life of the hemophilia patients. Historically, Hemophilia A has been treated with FVIII originating from human blood plasma. In blood plasma, under normal conditions, the FVIII molecule is always associated with its cofactor; von Willebrand factor (vWF), which stabilizes the FVIII molecule from different forms of degeneration.

Many processes have been described for purification of Factor VIII from plasma or cultures which recombinantly produce Factor VIII (rFVIII) with or without the presence of von Willebrand Factor. In the 90's, the first recombinant FVIII (rFVIII) products were marketed, divided in full length rFVIII molecules, mimicking the main form of FVIII in blood plasma, and B-domain deleted rFVIII molecules (Eriksson et al., 2001), in which one inactive portion (the B-domain) has been removed, both with a high degree of purity (all without vWF).

Hemophilia A patients are treated with FVIII on demand or as a prophylactic therapy administered several times a week. For prophylactic treatment 15-25 IU/kg bodyweight of FVIII is administered three times a week which is necessary due to the constant need of FVIII and its short half-life in the blood system, which is in humans only about 11 hours. (Ewenstein et al., 2004).

In frequent cases the constant treatment with exogenously administered FVIII causes a response of the patient's immune system (Saenko et al., Haemophilia 8:1-11 (2002), which presents a serious limitation to the therapy.

Presently, the most common option to achieve immune tolerance in patients with haemophilia A (congenital FVIII-deficiency) and inhibitors is immune tolerance induction (ITI), where high doses of FVIII are administered for prolonged periods of time. However, the treatment can take up to two years, remains unsuccessful in approximately 30% of patients, is extraordinarily costly, and cannot be used in a prophylactic manner to suppress the initial development of inhibitory antibodies.

Thus, approaches to attenuate the immune response are needed. One promising approach is the optimization of the glycosylation of either FVIII or its binding partner vWF.

For example, WO 2014/176125 A1 relates to immune conjugates for inducing antigen specific immune tolerance to FVIII. The immune conjugates are FVIII proteins conjugated to specific glycan ligands that target SIGLECs expressed on B-cells, namely SIG-1 or SIG-10 (or the ortholog SIG-G). The glycans ligands are in particular coupled to liposomes into which FVIII is introduced.

Sialic Acid Binding Immunoglobulin Lectins (SIGLECs) comprise a family of 15 human and 9 murine cell surface receptors that are expressed on various white blood cells of the immune system with the exception of most T-cells in mouse and man. The SIGLECs are located on different cell types and bind to different glycans structures (reviewed in Paulson et al. 2012). For example a binding of vWF and FVIII to SIG-5 has been demonstrated (Pegon 2012). However, the mechanism of binding remains unknown.

A different approach is described in WO 2014/179184 A1. The authors suggest reducing undesired antibody immune responses and inducing immune tolerance of blood coagulation factors, such as FVIII by addition of SIGLEC ligands. The SIGLEC ligands are selected from 9-N-biphenylcarboxyl-NeuAca2-6Gal~I-4GlcNAc (6'-BPCNeuAc), NeuAca2-6Galwl-4GlcNAc and NeuAca2-6Galwl-4(6-sulfo)GlcNAc. The SIGLEC ligand is linked to the coagulation factor via a water soluble polymer.

SUMMARY OF THE INVENTION

The present invention is, inter alia, based on the finding that the glycan structure naturally occurring in plasma derived proteins, in particular vWF enables an interaction with a group of SIGLECs, in particular SIG-5, SIG-7, SIG-8 and SIG-9. Moreover, the inventors found that by modification of the glycan structure on a protein the interaction with SIGLECs, such as SIG-5, SIG-7, SIG-8 and SIG-9 can be increased. This increase leads to a reduced immune response and/or increased immune tolerance of a patient to which the protein is administered.

Thus, according to a first aspect, the invention provides a glycosylated polypeptide comprising an amino acid sequence being identical or homologous to at least a fragment of a mammalian, preferably a human protein, wherein said glycosylated polypeptide contains one or more sialylated O-glycans and wherein the polypeptide has an increased binding affinity to one or more SIGLECs, selected from the group consisting of SIG-5, SIG-7, SIG-8, and SIG-9 compared to the mammalian protein or fragment thereof.

The inventors have specifically defined a glycan structure that is on the one hand needed for interaction with the SIGLECs but also the addition of which leads to an increased binding to the SIGLECs. Responsible for this are sialylated core 2 O-glycans and/or extended core 1 O-glycans.

Thus, the glycosylated polypeptide according to the first aspect can also be defined as a glycosylated polypeptide comprising an amino acid sequence being identical or homologous to at least a fragment of a mammalian, preferably a human protein, wherein said glycosylated polypeptide contains one or more sialylated O-glycans and wherein the combined number of sialylated core 2 O-glycans and sialylated extended core 1 O-glycans of the glycosylated polypeptide is higher than the combined number of sialylated core 2 O-glycans and sialylated extended core 1 O-glycans of the mammalian protein or fragment thereof.

A protein with a glycan composition including sialylated core 2 O-glycans and/or sialylated extended core 1 O-glycans, in particular sialylated core 2 O-glycans, can be used to modify the immune response of a patient to a therapeutic protein by combined administration.

Thus, according to a second aspect the invention relates to the use of a glycosylated polypeptide containing one or more sialylated O-glycans and exhibiting binding to one or more SIGLECs, selected from SIG-5, SIG-7, SIG-8, and SIG-9 for reducing the immune response or increasing the immune tolerance of a patient to therapeutic protein.

Using the modification of the glycosylated polypeptide with a binding affinity to SIGLECs it is not only possible to directly modify the SIGLEC binding affinity of the modified polypeptide itself but also of a protein complex or composition, which the glycosylated polypeptide is a part of, such as the complex of factor VIII (FVIII) and von-Willebrand-factor (vWF).

Thus, according to a third aspect the invention provides a protein composition comprising a first and a second polypeptide, wherein the first polypeptide is a glycosylated polypeptide containing one or more sialylated O-glycans and the second polypeptide contains an amino acid sequence homologous or identical to a second mammalian, in particular human protein, wherein—compared to the second polypeptide—the composition has an increased binding affinity to one or more SIGLECs selected from SIG-5, SIG-7, SIG-8, and SIG-9. The first and second polypeptide of the composition according to the third aspect preferably form a protein complex.

According to a fourth aspect, the invention provides an isolated polynucleotide that comprises a nucleic acid sequence encoding a glycosylated polypeptide according to the first aspect of the invention. In a fifth aspect the invention also relates to expression vector comprising a polynucleotide according to the fourth aspect of the invention.

The glycosylated polypeptide according to the first aspect, in particular vWF or FVIII and the composition according to the third aspect, in particular a complex of FVIII and vWF, are—due to the reduced immune response—particularly useful in medical treatment.

Thus, according to a fourth aspect, the invention provides a glycosylated polypeptide defined according to the first aspect or a composition defined according to the third aspect for use in the treatment of prevention of a bleeding disorder.

FIGURES

FIG. 1 shows the results of a binding test of vWF to different SIGLECs. The absorbance at 492 nm is proportional to the vWF bound to the respectively identified SIGLEC or the controls. SIG-2, SIG-5, SIG-7, SIG-F, SIG-9 and SIG-10 were immobilized via protein A on a microtiter plate at 500 ng/well. Biotinylated vWF was added at a concentration of 0 to 0.8 µg/mL and after washing, binding was visualized with HRP-conjugated streptavidin and absorbance measured at 492 nm. Anti-vWF and Anti-Chicken IgY was used for control.

FIG. 2 shows a schematic representation of vWF domain structure including N- and O-glycosylation, V8 protease cleavage sites and fragments resulting after V8 protease cleavage.

FIG. 3 shows the results of a binding test of an N-terminal and a C-terminal fragment of vWF to SIGLECs SIG-5, SIG-7, SIG-F and SIG-9. The absorbance at 492 nm is proportional to the vWF fragment bound to the respectively identified SIGLEC or the control. SIG-5, SIG-7, SIG-F and SIG-9 were immobilized via protein A on a microtiter plate at 500 ng/well. Biotinylated N-terminal VWF fragment (dark grey bars) and C-terminal vWF fragment (light grey bars) was added at a concentration of 1 µg/mL and after washing, binding was visualized with HRP-conjugated streptavidin and absorbance measured at 492 nm. Anti-Chicken IgY was used as negative control.

FIG. 4 shows the results of a binding test of the vWF N-terminal fragment, in desialylated, de-N-glycosylated and untreated form. The absorbance at 492 nm is proportional to the vWF N-terminal fragment bound to the respectively identified SIGLEC or the control. The N-terminal VWF fragment prior to digestion is represented by white bars, the PNGaseF de-N-glycosylated fragment by grey bars and the desialylated fragment by black bars. SIG-5, SIG-7, SIG-F and SIG-9 were immobilized via protein A on a microtiter plate at 500 ng/well. The biotinylated N-terminal vWF fragments (prior to digestion, digested with PNGaseF or SialidaseA) were added at a concentration of 8 µg/mL and after washing, binding was visualized with HRP-conjugated streptavidin and absorbance was measured at 492 nm. Anti-Chicken IgY was used for control.

FIG. 5 shows the results of a binding test of the O-glycosylation Cluster I and Cluster II to SIGLECs. The absorbance at 492 nm is proportional to the Cluster I fragment (light grey bars) or Cluster II fragment (dark grey bars) bound to the respectively identified SIGLEC or the control. SIG-5, SIG-7, SIG-F, SIG-9 and SIG-10 were immobilized via protein A on a microtiter plate at 500 ng/well. Biotinylated Cluster I and Cluster II were added at a concentration of 4 µg/mL and after washing, binding was visualized with HRP-conjugated streptavidin and absorbance measured at 492 nm. Anti-Chicken IgY was used as a negative control.

FIG. 6 shows the results of a binding test of the O-glycosylation Cluster II to SIGLECs before and after treatment with Sialidase A. The absorbance at 492 nm is proportional to the untreated Cluster II fragment (light grey bars) or the Cluster II fragment digested with Sialidase A (dark grey bars) bound to the respectively identified SIGLEC or the control. SIG-5, SIG-7, SIG-F and SIG-9 were immobilized via protein A on a microtiter plate at 500 ng/well. Biotinylated Cluster II prior to digestion (light grey bars) and digested with Sialidase A was added at a concentration of 2 µg/mL and after washing, binding was visualized with HRP-conjugated streptavidin and absorbance measured at 492 nm. Anti-Chicken IgY was used as a negative control.

FIG. 7 shows a schematic representation of recombinantly expressed vWF fragments Seq11 and Seq12.

FIG. 8 shows MALDI MS spectra of the O-glycopeptide isolated from Seq11 after tryptic/chymotryptic digestion; sialidaseA digestion and lectin enrichment. The identified peptide sequence is KVTLNPSDPEHCQICHCDVVNLT-CEACQEPGGLWPPTDAPVSPTTLYVEDI SEPPLH GSAW (SEQ ID NO: 6), the last four amino acids (underlined) correspond to the tag attached to the C-terminus of the sequence. Upper spectrum shows the fully O-glycosylated glycopeptide, bottom spectrum shows the same glycopeptide after O-glycosidase digestion.

FIG. 9 shows MALDI MS spectra of the O-glycopeptide isolated from Seq12 after tryptic/chymotryptic digestion; sialidaseA digestion and lectin enrichment. The identified peptide sequence is [KVTLNPSDPEHCQICHCDVVNLT- CEACQEPGGLVVPPTDAPVSPTTLYVEDI SEPPLHQEPGGLWPPTDAPVSPTTLYVEDISEPPLHQEPGGLWPPTDAPV SPTTLYVEDISEPPLHGSAW (SEQ ID NO: 7), the last four amino acids (underlined) correspond to the tag attached to the C-terminus of the sequence. Upper spectrum shows the fully O-glycosylated glycopeptide, bottom spectrum shows the same glycopeptide after O-glycosidase digestion.

FIG. 10 shows the results of a binding test of recombinant polypeptides Seq11 and Seq12 to SIGLECs. The absorbance at 492 nm is proportional to Seq11 (dark grey bars) or Seq12 (light grey bars) bound to the respectively identified SIGLEC or the control. SIG-5, SIG-7, SIG-F and SIG-9 were immobilized via protein A on a microtiter plate at 500 ng/well. Strep-Tag bearing sequences were applied on the plate at equal molar concentrations of 42 nM and after washing, binding was visualized with HRP-conjugated Streptactin and absorbance measured at 492 nm. Anti-Chicken IgY was used as a negative control and anti vWF pAb as a positive control.

FIG. 11 shows the results of a binding test of recombinant polypeptides Seq11 and Seq12 after Sialidase A treatment to SIGLECs. The absorbance at 492 nm is proportional to Seq11 (dark grey bars) or Seq12 (light grey bars) bound to the respectively identified SIGLEC or the control. SIG-5, SIG-7, SIG-F and SIG-9 were immobilized via protein A on a microtiter plate at 500 ng/well. Strep-Tag bearing sequences were enzymatically desialylated and applied on the plate at equal molar concentrations of 42 nM and after washing, binding was visualized with HRP-conjugated Streptactin and absorbance measured at 492 nm. Anti-Chicken IgY was used as a negative control and anti vWF pAb as a positive control.

FIG. 14 shows the summary of the $K_D$ values obtained from the Scachard analysis performed for curves presented in FIG. 12 and FIG. 13.

Figure 16:
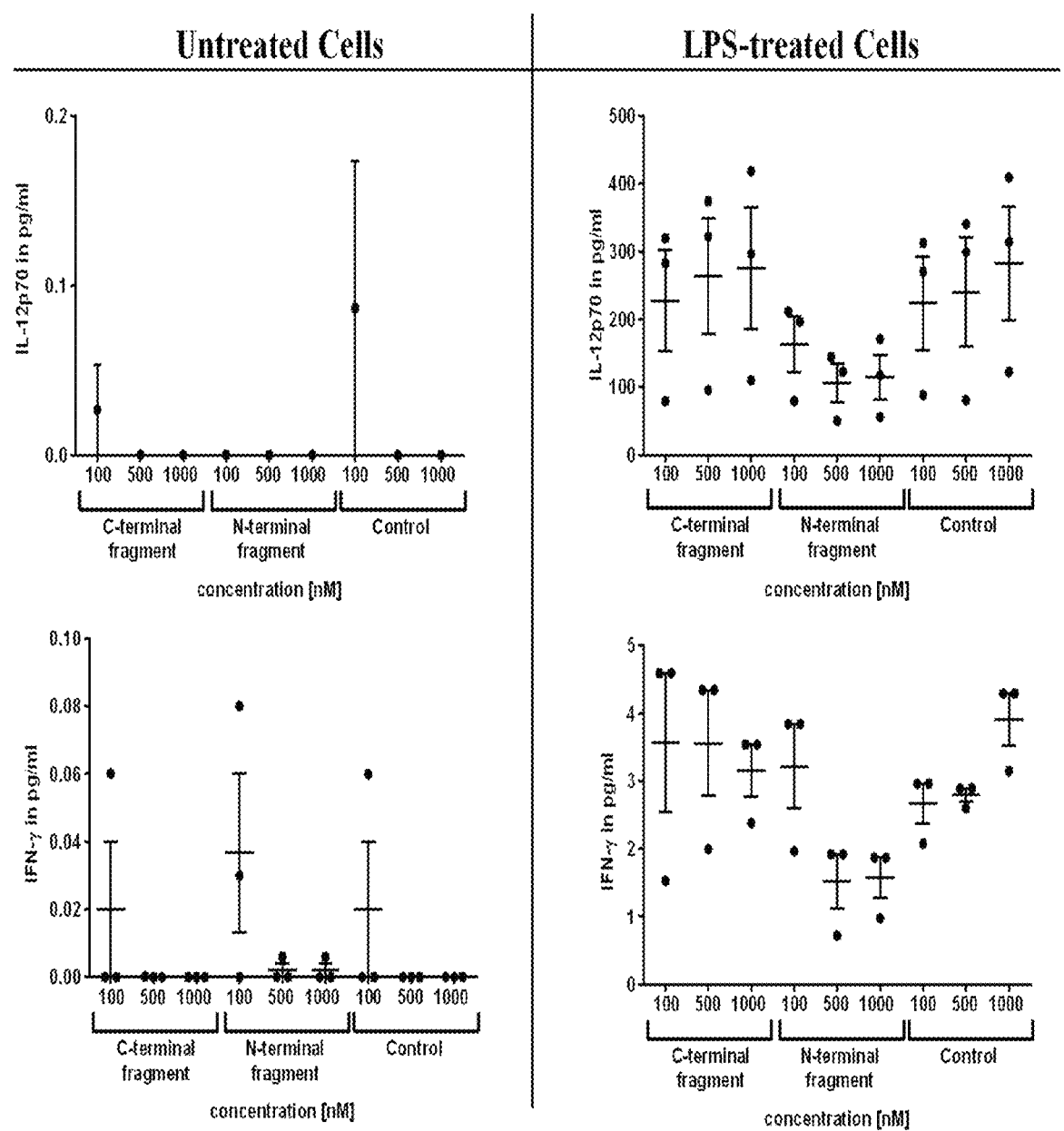

FIG. 16 Effect of N- and C-terminal VWF fragments on IL-12p70 and IFN-γ. moDC were cultivated with various concentrations of the VWF-fragments either without (left column) or with (right column) the addition of 0.1 μg/ml LPS. Extracellular levels of the cytokines was determined simultaneously via a cytometric bead array. IL-12p70 and IFN-γ levels of the unstimulated cells were for most donors below the detection limit (bd, 0.6 pg/ml for IL-12p70 and 1.8 pg/ml for IFN-γ). Data are presented as mean±SEM with each dot representing one donor.

Figure 17:
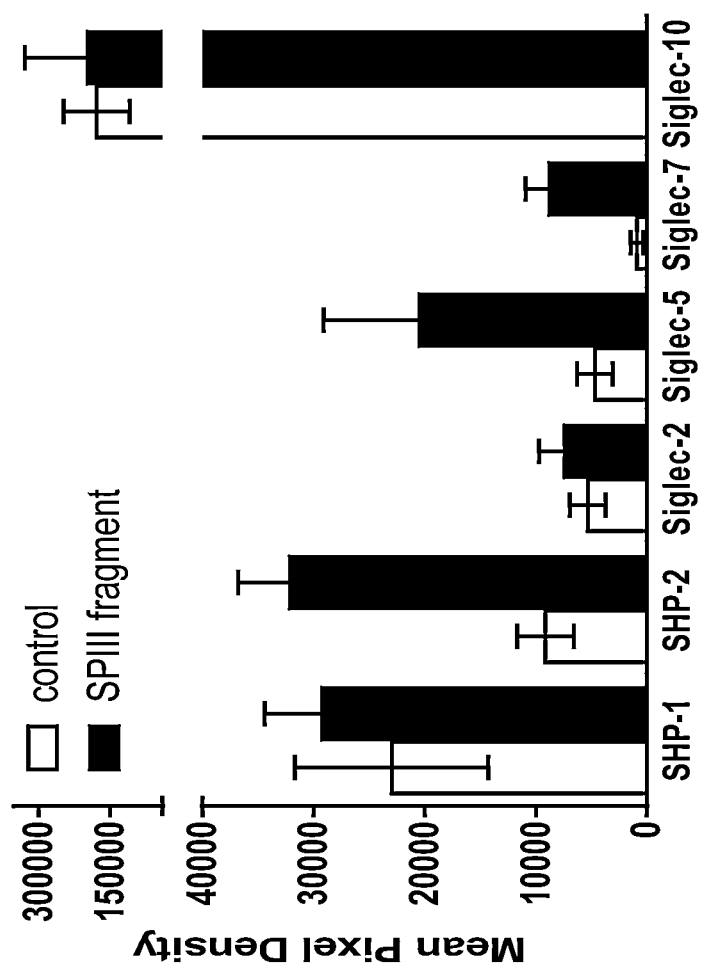

FIG. 17 shows the results of phosphorylation of SIGLECs and adaptor molecules SHP-1 and SHP-2 involved in SIGLEC-signaling following stimulation of moDC for 10 minutes with 500 nM of the N-terminal fragment of VWF. Cells stimulated with the same volume of 100 mM NaCl served as a control. Analysis of immunoreceptor-phosphorylation in the cell lysates was carried out with the Proteome Profiler Human Phospho-Immunoreceptor Array Kit. Results are shown as mean pixel density±SEM of 2-4 individual experiments.

DETAILED DESCRIPTION OF THE INVENTION

In order to provide a clear and consistent understanding of the specification and claims, and the scope to be given such terms, the following definitions are provided.

Definitions

A "peptide" as used herein may be composed of any number of amino acids of any type, preferably naturally occurring amino acids, which, preferably, are linked by peptide bonds. In particular, a peptide comprises at least 3 amino acids, preferably at least 5, at least 7, at least 9, at least 12, or at least 15 amino acids. Furthermore, there is no upper limit for the length of a peptide. However, preferably, a peptide according to the invention does not exceed a length of 500 amino acids, more preferably it does not exceed a length of 300 amino acids; even more preferably it is not longer than 250 amino acids.

Thus, the term "peptide" includes "oligopeptides", which usually refer to peptides with a length of 2 to 10 amino acids, and "polypeptides" which usually refer to peptides with a length of more than 10 amino acids.

The term "protein" as used herein refers to a peptide with at least 60, at least 80, preferably at least 100 amino acids. The terms "polypeptide" and "protein" are used interchangeably. The polypeptides and proteins as used herein include chemically synthesised proteins as well as naturally synthesised proteins which are encoded by genes. The polypeptides or proteins may be obtained from a natural source, such as human blood or produced in cell culture as recombinant proteins.

As used herein the term "mammalian protein" relates to the naturally occurring mammalian protein, i.e. a protein naturally expressed by a mammalian organism. Therefore, the mammalian protein has a naturally occurring amino acid sequence and naturally occurring post-translational modifications, such as glycosylation. According to the invention, the terms mammalian protein and naturally occurring mammalian protein may be used interchangeably.

As used herein the term "human protein" relates to the naturally occurring human protein, i.e. a protein naturally expressed by a human organism. Therefore, the human protein has a naturally occurring amino acid sequence and naturally occurring post-translational modifications, such as glycosylation. According to the invention, the terms human protein and naturally occurring human protein are used interchangeably.

"Recombinant proteins" or "recombinant polypeptides" as used herein are those which are encoded by transgenes introduced into the cells by molecular biology techniques. Proteins can be modified by chemical methods or by enzymes in post translational processes.

The term "fusion protein" according to the invention relates to proteins created through the joining of two or more genes, cDNAs or sequences that originally coded for separate proteins/peptides. The genes may be naturally occurring in the same organism or different organisms or may be synthetic polynucleotides.

The term "therapeutic protein" as used herein relates to proteins or polypeptides with a therapeutic effect, i.e. proteins used as active pharmaceutical ingredient.

The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the no brief option) is used as the percent identity and is calculated as follows:

(Identical Residues×100)/(Length of Alignment−
Total Number of Gaps in Alignment)

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim, except for impurities ordinarily associated therewith. When the phrase "consists of" appears in a clause of the body of a claim, rather than immediately following the preamble, it limits only the element set forth in that clause; other elements are not excluded from the claim as a whole. The transitional phrase "consisting essentially of" limits the scope of a claim to the specified materials or steps "and those that do not materially affect the basic and novel characteristic(s)" of the claimed invention. "A 'consisting essentially of' claim occupies a middle ground between closed claims that are written in a 'consisting of' format and fully open claims that are drafted in a 'comprising' format."

"Homologous" as used herein means that the respective amino acid sequence nucleotide sequence has a specified degree of identity with a reference amino acid sequence and the subject nucleotide sequences. A homologous sequence is taken to include an amino acid sequence that is at least 75%, 80%, 85%, 86%, 87%, 88%, 89%, 90%, 91%, 92%, 93%, 94%, 95%, 96%, 97%, 98% or even 99% identical to the subject sequence, using the conventional sequence alignment tool Clustal V with default parameters. Typically, homologues will include the same active site residues as the subject amino acid sequence, though may include any number of conservative amino acid substitutions. "Identical" as used herein refers to an amino acid or nucleotide sequence identity to a reference sequence of 100%.

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes at different levels or under different conditions than found in nature.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations The term "fragment" as used herein refers to a polypeptide that has an amino-terminal and/or carboxy terminal deletion of one or more amino acids as compared to the native or wild-type protein but where the remaining amino acid sequence is identical to the corresponding positions in the amino acid sequence deduced from a full-length cDNA. Fragments are typically at least 50 amino acids in length.

The term "glycosylation" as used herein refers to the attachment of glycans to molecules, for example to proteins. Glycosylation may be an enzymatic reaction. The attachment formed may be through covalent bonds. Accordingly, a glycosylated polypeptide as used herein is a polypeptide to which a glycans is attached. The phrase "highly glycosylated" refers to a molecule such as an enzyme which is glycosylated at all or nearly all of the available glycosylation sites, for instance O-linked or N-linked glycosylation sites.

The term "glycan" as used herein refers to a polysaccharide or oligosaccharide, or the carbohydrate section of a glycoprotein or glycosylated polypeptide. Glycans may be homo- or heteropolymers of monosaccharide residues. They may be linear or branched molecules. Glycans but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc.).

The term "O-glycans" as used herein refers to glycans that are generally found covalently linked to serine and threonine residues of mammalian glycoproteins. O-glycans may be α-linked via an N-acetylgalactosamine (GalNAc) moiety to the —OH of serine or threonine by an O-glycosidic bond. Other linkages include α-linked O-fucose, β-linked O-xylose, α-linked O-mannose, β-linked O-GlcNAc (N-acetylglucosamine), α- or β-linked O-galactose, and α- or β-linked O-glucose glycans.

The term "sialylated" as used herein refers to molecules in particular glycans that have been reacted with sialic acid or its derivatives.

The terms "binding affinity" or "affinity" as used herein indicate the strength of the binding between two molecules in particular a ligand and protein target. Binding affinities are influenced by non-covalent intermolecular interactions between the two molecules such as hydrogen bonding, electrostatic interactions, hydrophobic interactions, and van der Waals forces.

An immune response as used herein relates to adaptive or innate immune response. The innate immune response refers to nonspecific defense mechanisms that are activated immediately or within hours of an antigen's appearance in the body. These mechanisms include physical barriers such as skin, chemicals in the blood, and immune system cells that attack foreign cells in the body. The innate immune response is activated by chemical properties of the antigen. The adaptive immune response refers to antigen-specific immune response. For this, the antigen first must be processed and recognized. Once an antigen has been recognized, the adaptive immune system creates a large number of immune cells specifically designed to attack that antigen.

As used herein, "immune tolerance" (or simply "tolerance") is the process by which the immune system does not attack an antigen. It occurs in three forms: central tolerance, peripheral tolerance and acquired tolerance. Tolerance can be either "natural" or "self tolerance," where the body does not mount an immune response to self antigens, or "induced tolerance", where tolerance to antigens can be created by manipulating the immune system.

Glycosylated Polypeptide

According to a first aspect the invention provides a glycosylated polypeptide comprising an amino acid sequence being identical or homologous to at least a fragment of a mammalian, preferably a human protein, wherein said glycosylated polypeptide contains one or more sialylated O-glycans and wherein the polypeptide has an increased binding affinity to one or more SIGLECs compared to the mammalian protein or fragment thereof.

The glycosylated polypeptide according to the invention is based on a mammalian protein, i.e. contains an amino acid sequence identical or homologous to a mammalian protein. The mammalian protein is in particular a human protein. The human protein to which the amino acid sequence of the glycosylated peptide is homologous or identical to is preferably a glycosylated protein.

The human protein is more preferably a human blood protein. The human blood protein may be a human blood clotting factor, a transport protein, a protease inhibitor, an immunoglobulin, a cell related plasma protein, an apolipoproteins, a complement factor, a growth factor, an antiangionetic protein, a highly glycosylated protein, blood factors or another human blood protein.

The human blood clotting factor is in particular selected from the group consisting of fibrinogen, fibrin monomer, prothrombin, thrombin, FV, FX, FIX, FVII, FVIII, FXI, FXII, and FXIII, von Willebrand factor, and ADAMTS13.

It is appreciated that the clotting factors FV, FX, FIX, FVII, FVIII, FXI, FXII, and FXIII an inactivated an activated form. Thus, in the context of the invention, a reference to FV, FX, FIX, FVII, FVIII, FXI, FXII, and FXIII includes the activated forms FVa, FXa, FIXa, FVIIa, FVIIIa, FXIa, FXIIa, and FXIIIa, respectively unless explicitly stated otherwise or from the context the activated form can logically not be included. Thus, e.g. in this context FV, FX, FIX, FVII, FVIII, FXI, FXII, and FXIII may be read as FV/FVa, FX/FXa, FIX/FIXa, FVII/FVIIa, FVIII/FVIIIa, FXI/FXIa, FXII/FXIIa, FXIII/FXIIIa, The transport protein may be selected from albumin, transferrin, ceruloplasmin, haptoglobin, hemoglobin, and hemopexin.

Possible protease inhibitors are, e.g., ß-antithrombin, α-antithrombin, oxidized-antithrombin, 2-macroglobulin, CI-inhibitor, tissue factor pathway inhibitor (TFPI), heparin cofactor II, protein C inhibitor (PAI-3), Protein C, Protein S, and Protein Z.

Examples of immunoglobulin's such as polyclonal antibodies (IgG), monoclonal antibodies, IgG1, IgG2, IgG3, IgG4, IgA, IgA1, IgA2, IgM, IgE, IgD, and Bence Jones protein.

The cell related plasma protein may be for example, fibronectin, thromboglobulin, platelet factor 4. Examples of apolipoproteins are apo A-I, apo A-II, and apo E.

Complement factors according to the invention are e.g. Factor B, Factor D, Factor H, Factor I, C3b-Inactivator, properdin, C4-binding protein etc.

Examples of growth factors include Platelet derived growth factor (PDGF), Epidermal growth factor (EGF), Transforming growth factor alfa (TGF-α), Transforming growth factor beta (TGF-α), Fibroblast growth factor (FGF) and Hepatocyte growth factor.

Antiangionetic proteins include latent-antithrombin, prelatent-antithrombin, oxidized-antithrombin and plasminogen.

Examples of highly glycosylated proteins are alfa-1-acid glycoprotein, antichymotrypsin, inter-α-trypsin inhibitor, α-2-HS glycoprotein, C-reactive protein, Blood factors may be, e.g., such as erythropoeitin, interferon, tumor factors, tPA, gCSF.

Other human blood proteins include histidine-rich glycoprotein, mannan binding lectin, C4-binding protein, fibronectin, GC-globulin, plasminogen/plasmin, α-1 microglobulin, C-reactive protein.

The human protein is in particular selected from vWF, FVIII, FVII, FIX, ADAMTS13.

Factor VIII in humans is coded by the F8 gene which comprises 187.000 base pairs in six exons. The transcribed mRNA has a length of 9.029 base pairs and is translated to a protein with 2.351 amino acids from which by a posttranslational modification 19 amino acids are removed. The FVIII molecule in humans is glycosylated on a 31 amino acid side chain (25×N-glycosylation, 6×O-glycosylation).

After translation the amino acid chain is cleaved by specific proteases onto positions leading to the formation of a heavy chain with about 200 kDa and a light chain with about 80 kDa. The domain organization is typically characterized as A1-A2-B-A3-C1-C2. The light chain is a made-up of domains A3-C1-C2. The heavy chain is in principal composed of the domains A1-A2-B. Heavy chains found in plasma have a heterogeneous composition with molecular weights varying from 90 to 200 kDa. The reason for this are the heterogeneity in its glycosylation, the existence of splice variants and existence of proteolytic products such the B domain depleted heavy chain $A_1$ $A_2$. The amino acid sequence of the full length FVIII is identified by amino acids 20 to 2.351 of P00451 of SwissProt, Jul. 21, 1986.

The human protein is preferably full length FVIII identified by amino acids 20 to 2.351 of P00451 of SwissProt, Jul. 21, 1986, a B-domain deleted FVIII or a FVIII protein in which a part of the B-domain has been replaced by a linker.

vWF is a multimeric adhesive glycoprotein present in the plasma of mammals, which has multiple physiological functions. During primary hemostasis, vWF acts as a mediator between specific receptors on the platelet surface and components of the extracellular matrix such as collagen. Moreover, vWF serves as a carrier and stabilizing protein for procoagulant Factor VIII. VWF is synthesized in endothelial cells and megakaryocytes as a 2813 amino acid precursor molecule. The precursor polypeptide, pre-pro-vWF, consists of a 22-residue signal peptide, a 741-residue pro-peptide and the 2050-residue polypeptide found in mature plasma Von Willebrand Factor (Fischer et al., 1994). Full length vWF is identified by Uniprot entry P04275.

Upon secretion into plasma, vWF circulates in the form of various species with different molecular sizes. These vWF molecules consist of oligo- and multimers of the mature subunit of 2050 amino acid residues. vWF can be usually found in plasma as multimers ranging in size approximately from 500 to 20.000 kDa (Furlan et al. 1996). The vWF in particular has an amino acid sequence any of the sequences of Uniprot entry P04275. More preferably the vWF protein is identified by SEQ ID NO: 1.

LSCRPPMVKLVCPADNLRAEGLECTKTCQNY-DLECMSMGCVSGCLCPPGMVRHENRCVALER-CPCFHQG KEYAPGETVKIGCNTCVCQDRKWNCTD-HVCDATCSTIGMAHYLTFDGLKYLFPGECQYVL-VQDYCGSNPG TFRILVGNKGCSHPSVKCKKRVTIL-VEGGEIELFDGEVNVKRPMKDETHFEVVESGRY-IILLLGKALSVV WDRHLSISVVLKQTYQEKVCG-LCGNFDGIQNNDLTSSNLQVEEDPVDFGNSWKVSS-QCADTRKVPLDSSP ATCHNNIMKQTMVDSSCRILT-SDVFQDCNKLVDPEPYLDVCIYDTCSCESIGDCAC-FCDTIAAYAHVCAQ HGKVVTWRTATLCPQSCEERN-LRENGYECEWRYNSCAPACQVTCQHPEPLACPVQC-VEGCHAHCPPGKIL DELLQTCVDPEDCPVCEVAGRR-

FASGKKVTLNPSDPEHCQICHCDVVNLTCEACQEPG-
GLVVPPTDAPVS PTTLYVEDISEPPLHDFYCSRLLD-
LVFLLDGSSRLSEAEFEVLKAFVVDMMERLRISQKW-
VRVAVVEYHD GSHAYIGLKDRKRPSELRRIASQK-
YAGSQVASTSEVLKYTLFQIFSKIDRPEASRITLLL-
MASQEPQRM SRNFVRYVQGLKKKKVIVIPV-
GIGPHANLKQIRLIEKQAPENKAFVLSSVDELEQQR-
DEIVSYLCDLAPE APPPTLPPDMAQVTVGPGLL-
GVSTLGPKRNSMVLDVAFVLEGSDKIGEADFNR-
SKEFMEEVIQRMDVGQD sIHVTVLQYSYMVTVEY-
PFSEAQSKGDILQRVREIRYQGGNRTNTGLALRYL-
SDHSFLVSQGDREQAPNL VYMVTGNPASDEIKRLP-
GDIQVVPIGVGPNANVQELERIGWPNAPILIQDFETL-
PREAPDLVLQRCCSGE GLQIPTLSPAPDCSQPLD-
VILLLDGSSSFPASYFDEMKSFAKAFISKANIGPRL-
TQVSVLQYGSITTIDV PWNVVPEKAHLLSLVDV-
MQREGGPSQIGDALGFAVRYLTSEMHGARPGASKAV-
VILVTDVSVDSVDAAAD AARSNRVTVFPIGIGDRY-
DAAQLRILAGPAGDSNVVKLQRIEDLPTMVTLGNS-
FLHKLCSGFVRICMDED GNEKRPGDVWTLPDQCHT-
VTCQPDGQTLLKSHRVNCDRGLRPSCPNSQSPVK-
VEETCGCRWTCPCVCTGS STRHIVTFDGQNFKLTG-
SCSYVLFQNKEQDLEVILHNGACSPGARQGCMKSI-
EVKHSALSVELHSDMEVT VNGRLVSVPYVGGN-
MEVNVYGAIMHEVRFNHLGHIFTFTPQNNEFQLQL-
SPKTFASKTYGLCGICDENGA NDFMLRDGTVTTD-
WKTLVQEWTVQRPGQTCQPILEEQCLVPDSSHC-
QVLLLPLFAECHKVLAPATFYAIC QQDSCHQEQVCE-
VIASYAHLCRTNGVCVDWRTPDFCAMSCPPSLVY-
NHCEHGCPRHCDGNVSSCGDHPSE GCFCPPDKVM-
LEGSCVPEEACTQCIGEDGVQHQFLEAWVPDHQP-
CQICTCLSGRKVNCTTQPCPTAKAPT CGLCE-
VARLRQNADQCCPEYECVCDPVSCDLPPVPHCER-
GLQPTLTNPGECRPNFTCACRKEECKRVSPP SCPPH-
RLPTLRKTQCCDEYECACNCVNSTVSCPLGY-
LASTATNDCGCTTTTCLPDKVCVHRSTIYPVGQF
WEEGCDVCTCTDMEDAVMGLRVAQCSQKPCED-
SCRSGFTYVLHEGECCGRCLPSACEVVTGSPRGDS-
QSS WKSVGSQWASPENPCLINECVRVKEEVFIQ-
QRNVSCPQLEVPVCPSGFQLSCKTSACCPSCRCER-
MEACM LNGTVIGPGKTVMIDVCTTCRCMVQV-
GVISGFKLECRKTTCNPCPLGYKEENNTGECCGR-
CLPTACTIQL RGGQIMTLKRDETLQDGCDTHFCKV-
NERGEYFWEKRVTGCPPFDEHKCLAEGGKIM-
KIPGTCCDTCEEPE CNDITARLQYVKVGSCKSEVEV-
DIHYCQGKCASKAMYSIDINDVQDQCSCCSP-
TRTEPMQVALHCTNGSV VYHEVLNAMECKCSP-
RKCSK (SEQ ID NO: 1)

The glycosylated polypeptide may for example contain a fragment of vWF as defined in WO 2015/185758 A2. As shown in WO 2015/185758 A2, the complex of FVIII and the vWF fragments as defined therein exhibit a reduced binding to phospholipids membranes compared to FVIII alone as well as a reduced binding to collagen III and heparin compared to the complex of FVIII and full length vWF.

In this regard the fragment of vWF is in particular a fragment starting with amino acid 1 of SEQ ID No. 1. Amino acids 1 to 272 of SEQ ID NO:1 comprise the FVIII binding domain of vWF.

The fragment of vWF preferably starting with amino acid 1 of SEQ ID No. 1 preferably ends with an amino acid of SEQ ID NO: 1 in the range from 1142 to 1390. The fragment more preferably ends with an amino acid of vWF fragment in the range from 1267 to 1390. More preferably, the vWF fragment ends with an amino acid of SEQ ID NO: 1 in the range from 1337 to 1390.

It is to be understood that the glycosylated polypeptide has an increased binding affinity compared to the mammalian protein or fragment defined by the amino acid sequence contained in the glycosylated peptide. Thus, if the glycosylated polypeptide comprises the amino acid sequence of full length mammalian protein the glycosylated polypeptide has a higher affinity to SIGLECs compared to the full length mammalian protein.

On the other hand if the glycosylated polypeptide comprises a fragment of a mammalian protein defined by a subsequence of the mammalian protein the glycosylated polypeptide has an increased binding affinity as compared to the identical fragment derived from the naturally occurring protein. For example, if the amino acid sequence in the glycosylated polypeptide is identical or homologous to a fragment of vWF the glycosylated polypeptide according to the first aspect has an increased binding affinity to one or more SIGLECs as compared to the same fragment obtained from the fragmentation of plasma derived vWF.

As shown in the examples, a glycan structure of vWF was determined that specifically binds to at least the SIGLECs SIG-5, SIG-7, SIG-8 and SIG-9 (see example 1). Thus, according to one embodiment of the first aspect the one or more SIGLECs are selected from the group SIG-5, SIG-7, SIG-8 and SIG-9.

The inventors have surprisingly found that in human vWF the O-glycans are responsible for binding to SIG-5, SIG-7, SIG-8 and SIG-9. In contrast, the N-glycans do not show any binding to these SIGLECs (see example 2). This is particularly surprising, because so far it was rather the N-glycans that were shown to interact with SIGLECs (Lai et al, 2015).

The inventors further determined, that the O-glycans not only have to be sialylated for binding to SIG-5, SIG-7, SIG-8, SIG-9, but also minimal percentage of core 2 glycans has to be present (see example 4).

Therefore, the SIGLEC binding and consequently, the reduced immune response is based on an increased number or percentage of sialylated core 2 O-glycans in the glycosylated protein as compared to the number of sialylated core 2 O-glycans of the mammalian protein or fragment thereof.

Due to structural similarities it is assumed that sialylated extended core 1 O-glycans have the same effect as sialylated core 2 glycans. Thus, to increase the binding affinity to the SIGLECs defined above preferably the combined number or percentage of sialylated core 2 and extended core 1 O-Glycans is increased.

Thus, according to one embodiment the number of sialylated core 2 and/or extended core 1 O-glycans of the glycosylated polypeptide is higher than the number of sialylated core 2 and/or extended core 1 O-glycans of the mammalian protein or fragment thereof. In this regard also the percentage of sialylated core 2 and/or extended core 1 O-glycans is increased as compared the percentage of core 2 and/or extended core 1 O-glycans of the mammalian protein.

This means that the combined number of sialylated core 2 O-glycans and sialylated extended core 1 O-glycans of the glycosylated polypeptide is higher than the combined number of sialylated core 2 O-glycans and sialylated extended core 1 O-glycans of the mammalian protein or fragment thereof.

Alternatively only the number of sialylated core 2 O-glycans may be increased. In this regard also the percentage of sialylated core 2 O-glycans is increased as compared the percentage of core 2 O-glycans of the mammalian protein.

The SIGLECs for which a binding was shown are involved in the immune response of humans and mice.

SIGLECs have in common an N-terminal V-set Ig domain that binds sialic acid containing ligands, and a variable number of C2-set Ig domains that extend the ligand-binding side away from surface of the membrane.

In addition, many SIGLECs have cytoplasmic tyrosine motifs, including immunoreceptor tyrosine-based inhibitory motif (ITIM) and ITIM-like motifs, commonly found in co-receptors involved in regulation of cell signalling. Other SIGLECs do not contain tyrosine-motifs but contain positively charged trans-membrane spanning region that permits association with the adapter proteins. SIGLECs do not recognize danger associated molecular patterns (DAMPS) but instead determinants of "self".

SIGLECs bind to such sialylated self ligands on the same cell in "cis" and on adjacent cells in "trans". The human SIGLECs are usually referred to as SIG-1 to SIG-14. The mouse SIGLECs SIG-E, SIG-F and SIG-G are orthologs of the human SIGLECs SIG-9, SIG-8 and SIG-10, respectively.

SIG-1 to SIG-4 are also referred to by the names Sialoatesin, CD22, CD33 and MAG, respectively. CD22 and SIG-10 are located an B-cells, SIG-5 on neutrophils and monocytes, SIG-7 on NK-cells, SIG-8 on eosinophils, SIG-9 on monocytes, neutrophils and dendritic cells (Paulsen et al 2012).

SIGLECs bind to a variety of different glycans structures. Each of the SIGLECS SIG-2, SIG-5, SIG-7, SIG-8, SIG-9 and SIG-10 has a different glycan preference (Paulson et al., 2012). SIGLECs play a role in innate and adaptive immunity. In particular SIG-2 and SIG-10 that are located on B-cells of humans and mice.

According to Paulsen et al., SIG-2 and SIG-10 appear to synergistically contribute to peripheral B-cell tolerance. Additionally SIGLECs appear to act as inhibitory co-receptors for toll-like receptors (TRLs). In this regard, it was shown that cross-linking SIG-7 or SIG-9 to activation receptors results in inhibition of the cytolytic activity of NK-cells against tumor cells and release of chemical mediators from mast cells respectively.

Moreover, cross-linking of SIG-E (SIG-9) and SIG-11 by an immobilized anti-body results in inhibition of cytokine production in response to LPS in macrophages.

Of note, a topic expression of SIG-5 and SIG-9 in a macrophage cell line has been shown to inhibit the TNF-alpha production and enhance IL-10 production in response to peptide glycan, ATLR2 ligand, LPS and CpG. In addition, LPS induced SIG-E (SIG-9) expression in macrophages appears the effect that effect the TRL signalling. Also, sialylated pathogens dampen the immune response via SIGLECs. As an example group B *streptococcus* expresses the Neu-Acα-1 Galβ-1 4GlcNAc residue on the capsular polysaccharides and recruits SIGLEC-9 on neutrophils, resulting in suppression of microbicidal function of neutrophils.

Accordingly, without wanting to be bound to theory it is believed that the binding to SIGLECS on antigen presenting cells (like e.g. dendritic cells) lead to down-regulation of pro-inflammatory and up regulation of immunosuppressive receptors expression on the cell surface. Also, the binding leads to an enhanced production of anti-inflammatory cytokines, lower the production of pro-inflammatory cytokines, and in consequence lead to the inhibition on T-cell proliferation and antibody production. Thus, binding of the SIGLECs SIG-5, SIG-7, SIG-8 and SIG-9 leads to a reduced immune response or increased immune tolerance when the glycosylated polypeptide is administered to a patient.

Thus, the glycosylated polypeptide according to the first aspect can also be defined as a glycosylated polypeptide comprising an amino acid sequence being identical or homologous to at least a fragment of a mammalian, preferably a human protein, wherein said glycosylated polypeptide contains one or more sialylated O-glycans and wherein in comparison to the mammalian protein or fragment thereof:
the immune response of a human to the glycosylated polypeptide is reduced; and/or
the immune tolerance of human to the glycosylated polypeptide is increased.

On the other hand a more structural definition of a first aspect of the invention is a glycosylated polypeptide comprising an amino acid sequence being identical or homologous to at least a fragment of a mammalian, preferably a human protein, wherein said glycosylated polypeptide contains one or more sialylated O-glycans and wherein the combined number of sialylated core 2 O-glycans and sialylated extended core 1 O-glycans of the glycosylated polypeptide is higher than the combined number of sialylated core 2 O-glycans and sialylated extended core 1 O-glycans of the mammalian protein or fragment thereof.

Preferably the glycosylated polypeptide comprising an amino acid sequence being identical or homologous to at least a fragment of a mammalian, preferably a human protein, wherein said glycosylated polypeptide contains one or more sialylated O-glycans and wherein the number of sialylated core 2 O-glycans of the glycosylated polypeptide is higher than the combined number of sialylated core 2 O-glycans of the mammalian protein or fragment thereof.

In order to couple the O-glycans to the amino acid sequence of the glycosylated polypeptide it contained one or more O-glycosylation sites. O-glycosylation sites of the glycosylated polypeptide can be the standard O-glycosylation sites serine (Ser), and threonine (Thr). However, also the binding of O-glycans to tyrosine (Tyr), hydroxlysine (Hydroxy-Lys) or hydroxyproline (Hydroxy-Pro) has been described is possible in the context of the invention. Thus, the one or more O-glycosylation sites in the glycosylated polypeptide may be selected from Ser, Thr, Tyr, Hydroxy-Lys and Hydroxy-Pro in any further possible O-glycosylation site. Preferably, the O-glycosylation sites are selected from Ser and Thr.

The standard glycosylation sites Ser and Thr generally show the highest occupation with O-glycans. Thus, according to one embodiment the one or more glycosylation sites are selected from Ser and Thr.

In the context of the invention for practical reasons the term "glycosylated polypeptide" is used in the singular form. Generally the glycosylated polypeptide will occur in form of a composition of polypeptides of the same type. In this regard glycosylated polypeptides in early form are a composition of glycosylated polypeptides having the same amino acid sequence, however, variances in the glycosylation. For example, not all of the individual molecules of the composition may be glycosylated to 100 percent. Moreover, differences in the glycans bound to a specific O-glycosylation site may arise. Accordingly, the present invention also relates to a composition comprising at least glycosylated polypeptide molecules of a first type, wherein the amino acid sequence of the protein molecules of the first type is identical or homologous to at least a fragment of a mammalian, preferably human protein and the protein molecules contain one or more glycosylation sites.

Preferably, the polypeptide contains one or more clusters of glycosylation sites. Although a single glycosylation site may be sufficient of SIGLEC binding, this assumed the formation of a cluster of O-glycosylation sites leads to an improved binding to SIGLECs. Cluster formation of glycosylation sites is often observed in mammalian proteins, examples are human IgA containing clustered O-glycans in the hinge region (cf. Franc et al. 2013) and human mucin (cf. Guzman-Aranguez and Argüeso 2010).

In this regard already two O-glycosylation sites in close proximities are considered in an O-glycosylation cluster. Thus, the one or more cluster of O-glycosylation sites contain at least two O-glycosylation sites. The clusters of O-glycosylation sites may have different numbers of O-glycosylation sites. For example, the glycosylated polypeptide may contain one cluster with two and second a cluster with three of glycosylation sites. Between the O-glycosylation sites of a cluster also N-glycosylation sites may be present. Preferably there are no N-glycosylations sites in the O-glycosylation cluster.

Furthermore, one cluster may contain three O-glycosylation sites and the other four O-glycosylation sites. A number of three O-glycosylation sites results in three neighboring O-glycans that all may interact with the SIGLECs and therefore lead to an increased effect. According to one embodiment the one or more clusters of O-glycosylation sites preferably contain at least three O-glycosylation sites.

In vWF, two clusters are present with each four O-glycosylation sites. Thus, preferably a polypeptide contains one or more clusters with at least four O-glycosylation sites. Presently, it is assumed that the higher the number of O-glycosylations sites the higher is the binding affinity.

A cluster of O-glycosylation sites may be defined by two or more O-glycosylation sites within a short distance in the amino acid sequence. Those clusters are also referred to as "sequence clusters". However, due to the three-dimensionally assembly of the glycosylated polypeptide an O-glycosylation cluster may also include O-glycosylation sites that are in a further distance within the amino acid sequence but after folding are located in close proximity. This latter type of clusters is also referred to as "folding cluster". The vWF O-glycosylation cluster 2 contains 4 O-glycosylation sites within 20 amino acids, which are arranged as a beta turn. Accordingly, the distance of the O-glycans or O-glycosylation sites are 27.2 Å to 34.0 Å, leading to a mean distance of 6.8 Å to 8.5 Å. Thus the mean distance of two O-glycosylation sites in a cluster may be in the range from 4.0 Å to 15.0 Å. Below 4.0 Å there may a sterical hinderance of the O-glycans, in particular it may not be possible to glycosylate both O-glycosylation sites. Above the mean distance of two amino acids of more than 15.0 Å it is likely that there is no collaborative effect of the O-glycans. The collaborative effect is, e.g., an interaction with SIGLECs on the same cell. Preferably the mean distance of two O-glycosylation sites in a cluster is in the range from 5.0 Å to 12.0 Å. More preferably the mean distance of two O-glycosylation sites in a cluster is in the range from 6.0 Å to 9.0 Å.

Folding clusters may span amino acid sequences of over 100 amino acids. However, it is preferred that the spatial arrangement of the cluster does not exceed 80 Å. If the O-glycosylation sites are spaced apart more than 80 Å it is assumed that the O-glycans do not exhibit a combined effect. The combined effect of the O-glycans in a cluster are the strongest if the O-glycans are located within an area with a diameter of 50 Å. Thus, more preferably the spatial arrangement cluster does not exceed 50 Å.

According to one embodiment the one or more clusters, i.e. sequence clusters, contain at least one O-glycosylation site in ten amino acids. If the O-glycosylation sites are spread out further it is believed that O-glycans bound to the O-glycosylation site cannot probably act together on the same cell containing the SIGLECs.

Preferably, the one or more clusters contain at least one O-glycosylation site in four amino acids. With an average distance of the O-glycosylation sites of four amino acids there is a high chance that the O-glycosylation sites are also in close proximity after folding. The spatial proximity allows for a collaborative interaction of the glycans in the cluster with SIGLECs on the same cell.

More preferably, the one or more clusters contain at least one O-glycosylation sited in three amino acids. As shown in the examples the tested vWF peptide contains clusters with one O-glycosylation site in two amino acids. Thus, according to a preferred embodiment the one or more clusters contain at least one glycosylation site in two amino acids.

As shown in the examples, already one of such O-glycosylation clusters is enough for strong interaction with SIGLECs. Moreover, it is also shown by comparison of two vWF polypeptides a higher number of clusters of O-glycosylation sites leads to an increased binding affinity of the peptide to SIGLECs, in particular SIG-5, SIG-7, SIG-8 and SIG-9. Thus the glycosylated polypeptide preferably comprises at least two glycosylation clusters, more preferably at least three glycosylation clusters.

Without wanting to be bound to theory, the binding affinity of the glycosylated polypeptide to the SIGLECs is higher the closer the clusters are located. In this regard, if two clusters are present they are preferably separated by less than 100 amino acids. A distance of less than 100 amino acids allows a collaborative effect of the clusters of glycans in SIGLEC binding. More preferably, two clusters are separated by less than 50 amino acids. Most preferably two clusters are separated by less than 30 amino acids.

According to one embodiment the distance between any two neighboring clusters is less than 100 amino acids, preferably the distance between any two clusters within the glycosylated polypeptide is less than 50 amino acids. More preferably, the distance between any two neighboring clusters is less than 30 amino acids.

The glycosylated polypeptide preferably contains at least one additional cluster of O-glycosylation sites as compared to the human protein to which the sequence is homologous or identical.

As defined above, like all glycosylated polypeptides the glycosylated polypeptide according to the invention represents a composition of glycosylated polypeptide molecules. These molecules exhibit a certain degree of heterogeneity within the glycosylation pattern, in particular not all of the glycosylation sites are necessarily occupied by O-glycans. The occupation by O-glycans is in particular dependent on the host cell in which the recommended glycosylated polypeptide is produced. Preferably, the host cell, i.e. expression system is chosen such that the percentage of occupation of the O-glycosylation sites is above 70%. An occupation below 70% not enough O-glycans may be present for SIGLEC binding. Preferably, more than 80% of the O-glycosylation sites are occupied by O-glycans. More preferably, more than 90% of the O-glycosylation sites are occupied with O-glycans. According to a preferred embodiment more than 95% of the O-glycosylation sites are occupied by O-glycans.

The composition of glycans attached to the glycosylated polypeptide depends on the method of production. The O-glycans may be natural of synthetic glycans. Natural O-glycans are for example glycans with the following core structure:

Core 1 O-glycan: Galβ1→3GalNAcα1→Ser/Thr

Extended Core 1: O-glycan: Galβ1→4GlcNAcβ1→3Galβ1→3GalNAcα1→Ser/Thr

Core 2 O-glycan: Galβ1→3(Galβ1→3GlcNAcβ1→6)GalNAc α1→Ser/Thr

SIGLECs are known to bind to sialic acid. In conformity with this it is shown in the examples that desialylation abolished binding to the SIGLECs (see Example 3). Thus, it is confirmed that sialylation of the O-glycans is a prerequisite for binding. Accordingly, a high percentage of sialylation of the O-glycans in the glycosylated polypeptide is preferred.

Accordingly, the O-glycans of the glycosylated polypeptide are preferably sialylated, i.e. contain at least one sialic acid as part of the glycan molecule.

Preferably, the sialylated O-glycans contain at least two sialic acids in alpha 2-3 glycosidic linkage. Alternatively, the sialylated O-glycans may contain two sialic acids in alpha 2-8 glycosidic linkage. The sialylated O-glycans may also comprise alpha 2-3 and alpha 2-8 glycosidic linkage. According to one embodiment the sialylated O-glycans contain at least three sialic acids in 2-3 and/or 2-8 glycosidic linkage. The sialylated O-glycans in the glycosylated polypeptide are in particular core 1 or core 2 O-glycans. An overview of the structures of core 1, extended core 1 and core 2 O-glycans is given below:

Sialylated Core 1: O-glycan: NeuNAcα2→3Galβ1→3GalNAcα1→Ser/Thr

Sialylated extended Core 1 O-glycan: NeuNAcα2→3Galβ1→4GlcNAcβ1→3Galβ1→3GalNAcα1→Ser/Thr Sialylated Core 2 O-glycan: NeuNAcα2→3Galβ1→4GlcNAcβ1→6(NeuNAcα2→3Galβ1→3)GalNAcα1→Ser/Thr It is possible that both core 1 and core 2 and/or extended core 1 O-glycans need to be present on the glycosylated polypeptide. According to one embodiment the glycosylated polypeptide comprises sialylated core 1 O-glycans as well as sialylated core 2 and/or extended core 1 O-glycans. As shown in example 4 the percentage of core 2 glycans of 2.5% based on the total number of O-glycans is not enough for SIGLEC interaction. Thus, according to one embodiment of the glycosylated polypeptide the percentage of core 2 O-glycans based on the number of O-glycans is at least 5%. In the same example it is shown that cluster 2 with a core 2 O-glycan percentage based on a number of O-glycans of 10.78% leads to a strong interaction with the SIGLECs. Thus, according to a preferred embodiment the percentage of core 2 O-glycans based on the number of O-glycans in the glycosylated polypeptide is at least 8%. More preferably, the percentage of core 2 O-glycans based on the number of O-glycans is at least 10%.

In example 7 it was determined that about 80% of the glycopeptide molecules of the recombinantly produced vWF peptides contain either a core 2 O-glycan or a an extended core 1 glycan. Accordingly the percentage of sialylated core 2 and/or extended core 1 O-glycans based on the total number of O-glycans is at least 20%. Thus, according to one embodiment the concentration of core 2 and/or extended core 1 O-glycans based on the number of O-glycans in the glycosylated polypeptide is at least 15%, more preferably at least 18% and most preferably at least 20%.

The number or percentage of core 2 O-glycans in the glycosylated polypeptide, in particular the number or percentage of individual molecules of the glycosylated polypeptide bearing a core 2 O-glycan may be increased by any of the following strategies:

One strategy is using the enzyme β 1,6-N-acetylglucosaminyltransferase. This enzyme is involved in the formation of core 2 O-glycan. Thus an increase in core 2 bearing molecules and/or the number of core 2 O-glycan per polypeptide molecule can be obtained by expression of the glycosylated polypeptide in a cell line that overexpresses an enzyme β 1,6-N-acetylglucosaminyltransferase.

Another option is the expression of the glycosylated polypeptide in an expression cell line derived from a cancer cell line. Cancer cell lines are frequently shown to produces glycosylated proteins with a higher amount of core 2 O-glycans.

One strategy to increase the percentage of extended core 1 is using the enzyme β 1,3-N-acetylglucosaminyltransferase. This enzyme is involved in the formation of extended core 1 O-glycans. Thus an increase in extended core 1 bearing molecules and/or the number of extended core 1 O-glycan per polypeptide molecule can be obtained by expression of the glycosylated polypeptide in a cell line that overexpresses an enzyme β 1,6-N-acetylglucosaminyltransferase.

The concentration of core 2 and/or extended core 1 sialylated O-glycans can be increased by chemical synthesis of glycans.

Accordingly, based on the teaching of the invention the skilled person can adapt the glycans to determine synthetic glycans with high binding affinity. According to a preferred embodiment the O-glycans are natural glycans.

According to one embodiment at least a part of the sialylated core 2 O-glycans in the glycosylated polypeptide contains a sulfate group attached to galactose (Gal) or N-acetylglucosaminidase (GlcNAc) or fucose attached to GlcNAc in the core 2 type O-glycan, which represents high affinity binding ligand for SIGLECs 7, 8 and 8 (Paulson et al. 2012).

There are different ways known to the skilled person how to produce additional O-glycosylation sites. The glycosylated polypeptide may have an increased number of sialylated core 2 O-glycans due to an increased number of O-glycosylation sites as compared to the human protein or a fragment thereof.

In this regard the glycosylated polypeptide may be a fusion protein, wherein a second amino acid sequence containing one or more O-glycosylation sites is covalently linked to the amino acid sequence identical or homologous to the human protein or fragment thereof (first amino acid sequence). The second amino acid sequence may be located N-terminal with respect to the first amino acid sequence Alternatively, the second amino acid sequence may be located C-terminal with respect to the first amino acid sequence. The glycosylated polypeptide may contain additional amino acid sequences both N- and C-terminal to the first amino acid sequence Accordingly, in such a fusion protein a second amino acid sequence and optionally further amino acid sequences may be present that mainly contain O-glycosylation sites, in particular O-glycosylation clusters. The cluster of O-glycosylation sites may be based on an amino acid sequence of a known mammalian, in particular human protein glycosylated protein.

The second amino acid sequence may be comprise one or more of the following O-glycosylation clusters:

VVPPTXAPVXPTTXYVXXXSXPP, (SEQ ID NO: 8)

VVPPTDAPVSPTTLYVEDISEPP, (SEQ ID NO: 9)

PPPTXPPXXAXVTVXPXXXXVSTXXP, (SEQ ID NO: 10)

PPPTLPPDMAQVTVGPGLLGVSTLGP, (SEQ ID NO: 11)

VSSTSXXXXSTXPSXXXAAXTXXTSSXXPPSXPVXXXSXXXTTXXXX, (SEQ ID NO: 12)

VSSTSNNLISTIPSDNLAAGTDDTSSLGPPSMPVHYDSQLDTTLFGK, (SEQ ID NO: 13)

XXXATTXPXXXXXXTXPXXX, (SEQ ID NO: 14)

QFNATTIPENDIEKTDPWFA, (SEQ ID NO: 15)

XXTTAATXXX, (SEQ ID NO: 16)

LGTTAATELK, (SEQ ID NO: 17)

XXPTPXXXSXSXXXEAX, (SEQ ID NO: 18)

QSPTPHGLSLSDLQEAK; (SEQ ID NO: 19)

VXXXXXXXXXTXTSXXSPXXXXXVXXSXXXXTXXAXX, (SEQ ID NO: 20)
and

VHIYQKDLFFTETSDGSPGHLDLVEGSLLQGTEGAIK. (SEQ ID NO: 21)

In the sequences SEQ ID NO: 8, 10, 12, 14, 16, 18 and 20, X stands for any of the natural amino acids.

SEQ ID NO: 9 and 11 are found in vWF and SEQ ID NO: 13, 15, 17, 19 and 21 are derived from the B-domain of FVIII.

The second amino acid sequence may comprise one or more of the sequences selected from SEQ ID NO: 8, 10, 12, 14, 16, 18 and 20. The second amino acid sequence may contain combinations of the sequences. The second amino acid sequence preferably comprises multiple copies of one of the sequences SEQ ID NO: 8, 10, 12, 14, 16, 18 and 20. The second amino acid sequence may further comprise combinations of multiple copies of SEQ ID NO: 8, 10, 12, 14, 16, 18 and 20.

The second amino acid sequence may comprise one or more of the sequences selected from SEQ ID NO: 9, 11, 13, 15, 17, 19 and 21. The second amino acid sequence may contain combinations of the sequences. The second amino acid sequence preferably comprises multiple copies of one of the sequences SEQ ID NO: 9, 11, 13, 15, 17, 19 and 21. The second amino acid sequence may further comprise combinations of multiple copies of SEQ ID NO: 9, 11, 13, 15, 17, 19 and 21.

According to a preferred embodiment the second amino acid sequence contains one or more of copies of SEQ ID NO: 8.

Moreover, the second amino acid sequence may have a certain percentage of identity to the sequence of a naturally occurring glycosylated protein. The level of identity to a naturally occurring protein is preferable 80%, more preferably at least 90%.

Alternatively, the amino acid sequence of O-glycosylation sites in the second amino acid sequence may be fully synthetic. A fully synthetic amino acid sequence as used herein is a sequence not based on a known protein in particular mammalian protein.

According to one embodiment the covalent linker connecting the second amino acid sequence to the amino acid sequence identical or homologous to the human protein or fragment thereof in the glycosylated polypeptide is selected from a peptide bond, a chemical linker, or a glycosidic bond. Chemical linkers eligible in this regard are:
  amine to amine linkers such as bismaleimidoethane, 1,8-bismaleimido-diethyleneglycol,
  amine to sulfhydryl linkers such as succinimidyl iodoacetate, N-α-maleimidoacet-oxysuccinimide ester,
  carboxyl to amine linkers dicyclohexylcarbodiimide, 1-ethyl-3-(3-dimethylaminopropyl)carbodiimide hydrochloride and
  sulfhydryl to carbohydrate linkers such as N-β-maleimidopropionic acid hydrazide, N-ε-maleimidocaproic acid hydrazide.

The linker of the fusion protein according to the invention may be formed by a spacer peptide sequence that separates the first and second amino acid sequence which define the fusion protein. The spacer peptide sequence may facilitate the correct folding of the individual protein or peptide parts and may make it more likely for the individual protein or peptide parts to retain their individual functional properties. Spacer peptide sequences may be inserted into fusion protein DNA sequences during the in frame assembly of the individual DNA fragments that make up the complete fusion protein DNA sequence i.e. during overlapping PCR or DNA ligation.

A peptide bond has the advantage that the full glycosylated polypeptide can be expressed at once as fusion protein.

The second amino acid sequence may be added to the first amino acid sequence by a chemical linker and therefore after expression of the protein.

As shown in the examples, in particular vWF and fragments therefore containing the O-glycosylation clusters 1 and/or 2 bind to SIGLECs.

Thus, according to one embodiment the human protein is FVIII or a fragment thereof. Accordingly, the sequence identity to FVIII in the glycosylated polypeptide is at least 90%, more preferably at least 95% and most preferably at least 98%. According to a preferred embodiment the first amino acid sequence is identical or homologous to amino acids 1 to 505 of SEQ ID No: 1.

The length of the second amino acid sequence is preferably in the range from 5 to 100 amino acids, more preferably from 10 to 80 amino acids, most preferably from 20 to 70 amino acids.

According to one embodiment the second amino acid is at least 98% homologous to amino acids 475 to 505 of SEQ ID NO: 1. Preferably, the second amino acids sequence is identical to amino acids 475 to 505 of SEQ ID NO: 1. According to a more preferred embodiment a second amino acid sequence is at least 98% homologous to two consecutive copies of amino acids 475 to 505 of SEQ ID NO: 1. Preferably, the second amino acid sequence is identical to two consecutive copies of amino acids 475 to 505 of SEQ ID NO: 1.

A representative fusion protein according to the invention is Seq12. Seq12 has the following amino acids sequence (SEQ ID NO: 2):

```
SLSCRPPMVKLVCPADNLRAEGLECTKTCQNYDLECMSMGCVSGCLCPPG
MVRHENRCVALERCPCFHQGKEYAPGETVKIGCNTCVCQDRKWNCTDHVC
DATCSTIGMAHYLTFDGLKYLFPGECQYVLVQDYCGSNPGTFRILVGNKG
CSHPSVKCKKRVTILVEGGEIELFDGEVNVKRPMKDETHFEVVESGRYII
LLLGKALSVVWDRHLSISVVLKQTYQEKVCGLCGNFDGIQNNDLTSSNLQ
VEEDPVDFGNSWKVSSQCADTRKVPLDSSPATCHNNIMKQTMVDSSCRIL
TSDVFQDCNKLVDPEPYLDVCIYDTCSCESIGDCACFCDTIAAYAHVCAQ
HGKVVTWRTATLCPQSCEERNLRENGYECEWRYNSCAPACQVTCQHPEPL
ACPVQCVEGCHAHCPPGKILDELLQTCVDPEDCPVCVAGRRFASGKKVTL
NPSDPEHCQICHCDVVNLTCEACQEPGGLVVPPTDAPVSPTTLYVEDISE
PPLHQEPGGLVVPPTDAPVSPTTLYVEDISEPPLHQEPGGLVVPPTDAPV
SPTTLYVEDISEPPLH
```

The following sequence (SEQ ID NO: 3) represents Seq12 with an additional 22 amino acid signal peptide (bold and underlined). An expression of this peptide provides a monomeric form of Seq12. The signal peptide is enzymatically cleaved off.

(SEQ ID NO: 3)
<u>MIPARFAGVLLALALILPGTLC</u>SLSCRPPMVKLVCPADNLRAEGLECTKT
CQNYDLECMSMGCVSGCLCPPGMVRHENRCVALERCPCFHQGKEYAPGET
VKIGCNTCVCQDRKWNCTDHVCDATCSTIGMAHYLTFDGLKYLFPGECQY
VLVQDYCGSNPGTFRILVGNKGCSHPSVKCKKRVTILVEGGEIELFDGEV
NVKRPMKDETHFEVVESGRYIILLLGKALSVVWDRHLSISVVLKQTYQEK
VCGLCGNFDGIQNNDLTSSNLQVEEDPVDFGNSWKVSSQCADTRKVPLDS
SPATCHNNIMKQTMVDSSCRILTSDVFQDCNKLVDPEPYLDVCIYDTCSC
ESIGDCACFCDTIAAYAHVCAQHGKVVTWRTATLCPQSCEERNLRENGYE
CEWRYNSCAPACQVTCQHPEPLACPVQCVEGCHAHCPPGKILDELLQTCV
DPEDCPVCVAGRRFASGKKVTLNPSDPEHCQICHCDVVNLTCEACQEPGG
LVVPPTDAPVSPTTLYVEDISEPPLHQEPGGLVVPPTDAPVSPTTLYVED
ISEPPLHQEPGGLVVPPTDAPVSPTTLYVEDISEPPLH

A further representative fusion protein according to the invention is Pro-Seq12 including Seq12 and a propeptide (bold) with a signal peptide (bold and underlined). Pro-Seq12 is identified by SEQ ID NO: 4:

(SEQ ID NO: 4)
**<u>MIPARFAGVLLALALILPGTLC</u>AEGTRGRSSTARCSLEGSDEVNTFDGSM
YSFAGYCSYLLAGGCQKRSFSIIGDFQNGKRVSLSVYLGEFFDIHLFVNG
TVTQGDQRVSMPYASKGLYLETEAGYYKLSGEAYGFVARIDGSGNFQVLL
SDRYFNKTCGLCGNENIFAEDDFMTQEGTLTSDPYDFANSWALSSGEQWC
ERASPPSSSCNISSGEMQKGLWEQCQLLKSTSVFARCHPLVDPEPFVALC
EKTLCECAGGLECACPALLEYARTCAQEGMVLYGWTDHSACSPVCPAGME
YRQCVSPCARTCQSLHINEMCQERCVDGCSCPEGQLLDEGLCVESTECPC
VHSGKRYPPGTSLSRDCNTCICRNSQWICSNEECPGECLVTGQSHFKSFD
NRYFTFSGICQYLLARDCQDHSFSIVIETVQCADDRDAVCTRSVTVRLPG
LHNSLVKLKHGAGVAMDGQDVQLPLLKGDLRIQHTVTASVRLSYGEDLQM
DWDGRGRLLVKLSPVYAGKTCGLCGNYNGNQGDDFLTPSGLAEPRVEDFG
NAWKLHGDCQDLQKQHSDPCALNPRMTRFSEEACAVLTSPTFEACHRAVS
PLPYLRNCRYDVCSCSDGRECLCGALASYAAACAGRGVRVAWREPGRCEL
NCPKGQVYLQCGTPCNLTCRSLSYPDEECNEACLEGCFCPPGLYMDERGD
CVPKAQCPCYYDGEIFQPEDIFSDHHTMCYCEDGFMHCTMSGVPGSLLPD
AVLSSPLSHRSKR**SLSCRPPMVKLVCPADNLRAEGLECTKTCQNYDLECM
SMGCVSGCLCPPGMVRHENRCVALERCPCFHQGKEYAPGETVKIGCNTCV
CQDRKWNCTDHVCDATCSTIGMAHYLTFDGLKYLFPGECQYVLVQDYCGS
NPGTFRILVGNKGCSHPSVKCKKRVTILVEGGEIELFDGEVNVKRPMKDE
THFEVVESGRYIILLLGKALSVVWDRHLSISVVLKQTYQEKVCGLCGNFD
GIQNNDLTSSNLQVEEDPVDFGNSWKVSSQCADTRKVPLDSSPATCHNNI
MKQTMVDSSCRILTSDVFQDCNKLVDPEPYLDVCIYDTCSCESIGDCACF
CDTIAAYAHVCAQHGKVVTWRTATLCPQSCEERNLRENGYECEWRYNSCA
PACQVTCQHPEPLACPVQCVEGCHAHCPPGKILDELLQTCVDPEDCPVCE
VAGRRFASGKKVTLNPSDPEHCQICHCDVVNLTCEACQEPGGLVVPPTDA
PVSPTTLYVEDISEPPLHQEPGGLVVPPTDAPVSPTTLYVEDISEPPLHQ
EPGGLVVPPTDAPVSPTTLYVEDISEPPLH

Expression of Pro-Seq12 results in the formation of dimers. The peptide dimers remain also after cleavage of the propeptide.

According to one embodiment the glycosylated polypeptides contains a first amino acid sequence that is at least 98% identical to amino acids 1 to 505 of SEQ ID NO: 1. The second amino acid sequence is at least 98% homologous to two consecutive copies of amino acids 475 to 505 of SEQ ID NO: 1.

According to one embodiment the glycosylated polypeptide is produced by expression in a human cell-line. Generally any human cell-line is suitable for expression of the glycosylated polypeptide. A favourable glycosylation peptide is particularly obtained with HEK cell-lines.

Examples of HEK cell-lines for production of the glycosylated polypeptide are HEK 293 F, Flp-In™-293 (Invitrogen, R75007), 293 (ATCC® CRL-1573), 293 EBNA, 293 H (ThermoScientific 11631017), 293S, 293T (ATCC® CRL-3216™), 293T/17 (ATCC® CRL11268™, 293T/17 SF (ATCC® ACS4500™), HEK 293 STF (ATCC® CRL 3249™), HEK-293.2sus (ATCC® CRL-1573™). A preferred cell line for production of the polypeptide is the HEK 293 F as cell line.

Other cell lines suitable as host cells for expression include cell lines derived from human myeloid leukaemia cells. Specific examples of host cells are K562, NM-F9, NM-D4, NM-H9D8, NM-H9D8-E6, NM H9D8-E6Q12, GT-2X, GT-5s and cells derived from anyone of said host cells. K562 is a human myeloid leukemia cell line present in the American Type Culture Collection (ATCC CCL-243).

The remaining cell lines are derived from K562 cells and have been selected for specific glycosylation features.

According to an alternative embodiment the one or more glycosylation sites are located within the amino acid sequence homologous or identical to the mammalian protein or fragment thereof. This is to be understood that O-glycosylation sites that are not present in the amino acid sequence of the mammalian protein or fragment are found within the homologous or identical amino acid sequence within the glycosylated polypeptide.

The one or more O-glycosylation sites within the amino acid sequence homologous or identical to the mammalian protein or fragment thereof may be inserted within the sequence. Alternatively the one or more O-glycosylation sites may replace amino acids of the mammalian protein. An amino acid replacement is preferred as it does not change the size of the polypeptide chain and therefore is less likely to influence the three-dimensional structure of the protein.

The one or more O-glycosylation sites within the amino acid sequence are preferably in parts of the sequence that do not form binding sites or active centers of the protein. Moreover, the one or more O-glycosylation sites are preferably added in an amino acid position that will be exposed to the surface of the folded protein. In order to achieve the least influence on the activity or integrity of the protein, the one or more O-glycosylation sites may be added to a flexible loop of the protein.

In case of FVIII proteins, the one or more O-glycosylation sites are preferably added in the position of or replacing the B-domain.

In one embodiment, the glycosylated polypeptide is modified by attachment with one or more biocompatible polymers to improve, e.g., half-life or stability. Suitable biocompatible polymers include polyalkylene oxides such as, without limitation, polyethylene glycol (PEG), dextrans, colominic acids or other carbohydrate based polymers, polymers of amino acids, biotin derivatives, polyvinyl alcohol (PVA), polycarboxylates, polyvinylpyrrolidone, polyethylene-co-maleic acid anhydride, polystyrene-co-malic acid anhydride, polyoxazoline, polyacryloylmorpholine, heparin, albumin, celluloses, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates, other bio-polymers and any equivalents thereof. In one embodiment, the polymer is polyethylene glycol (PEG). In another embodiment, the polymer is methoxypolyethylene glycol (mPEG). Other useful polyalkylene glycol compounds are polypropylene glycols (PPG), polybutylene glycols (PBG), PEG-glycidyl ethers (Epox-PEG), PEG-oxycarbonylimidazole (CDI-PEG), branched polyethylene glycols, linear polyethylene glycols, forked polyethylene glycols and multi-armed or "super branched" polyethylene glycols (star-PEG). The biocompatible polymer is preferably connected to the polypeptide by one of the following residues —SH, OH, —COOH.

According to one embodiment the glycosylated polypeptide is able to form dimers or multimers. The formation of dimers and in particular multimers increases the number of O-glycans or O-glycan clusters in close proximity. Thus, more O-glycan may interact with SIGLECs on one cell. Moreover, the O-glycans can interact with several SIGLEC expressing cells that are located closely together, thereby increasing the immune tolerance.

Multimerization may be the result of a multimerization domain in in the amino acid sequence of the mammalian protein on which the glycosylated polypeptide is based. Alternatively, multimers of the glycosylated polypeptide can be formed by introducing multimerization domains into amino acid sequence of the glycosylated polypeptide.

An example of a fusion protein according to the invention that forms multimers is the Pro-Seq12-Mult including Seq12 and a propeptide (bold) with a signal peptide (bold and underlined) as well as a multimerization sequence, the "cystein knot domain" of vWF (underlined). Pro-Seq12-Mult is identified by SEQ ID NO: 5:

MIPARFAGVLLALALILPGTLCAEGTRGRSSTARCSLEGSDEVNTFDGSM

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNENIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHEKSED

NRYFTESGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDFG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGFMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CQDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNFD

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHQEPGGLVVPPTDAPVSPTTLYVEDISEPPLHQ

EPGGLVVPPTDAPVPTTLYVEDISEPPLHEEPECNDITARLQYVKVGSCK

SEVEVDTHYCQGKCASKAMYSIDINDVQDQCSCCSPTRTEPMQVALHCTN

GSVVYHEVLNAMECKCSPRKCSK

Alternatively multimerization of the glycosylated polypeptide may be obtained by binding to a polymer or a liposome.

Use of a Glycosylated Polypeptide

As defined above the inventors have found that a protein with a glycan composition including sialylated core 2 O-glycans and/or sialylated extended core 1 O-glycans interacts with defined SIGLECs and therefore influences cells of the immune system of mammals. In particular a glycosylated polypeptide has exhibits a reduced immune response. Therefore such glycosylated polypeptide if administered with a second protein can influence the immune response of a patient to the second protein. Therefore a glycosylated polypeptide with sialylated core 2 O-glycans and/or sialylated extended core 1 O-glycans can be used to modify, in particular reduce the immune response of a patient to a protein in particular a therapeutic protein in combined administration.

Thus, according to a second aspect the invention relates to the use of a glycosylated polypeptide containing one or more sialylated O-glycans and exhibiting binding to one or more SIGLECs, selected from SIG-5, SIG-7, SIG-8, and SIG-9 for reducing the immune response of a therapeutic protein.

Preferably the glycosylated polypeptide used for reducing the immune response comprises sialylated core 2 O-glycans and/or sialylated extended core 1 O-glycans. More preferably the glycosylated polypeptide is defined as the glycosylated polypeptide according to the first aspect.

The use can also be described as a method of treating a patient with a therapeutic protein, wherein the method comprises administering the glycosylated polypeptide containing one or more sialylated O-glycans and exhibiting binding to one or more SIGLECs, selected from SIG-5, SIG-7, SIG-8, and SIG-9 for reducing the immune response of therapeutic protein.

Composition and Protein Complex

Accordingly, the concept according to the invention, namely the reduced immune response of a human protein by e.g. addition of one or more sialylated core 2 O-glycans cannot only be achieved by the preparation of a fusion protein or by insertion or replacement of amino acids by O-glycosylation sites but also by adding an additional polypeptide as described in the use according to the second aspect. This leads to the formation of a composition of the glycosylated polypeptide and a second polypeptide the immune response of which is to be reduced.

Accordingly, in a third aspect the present invention also relates to a composition comprising a first and a second polypeptide, wherein the first polypeptide is a glycosylated polypeptide containing one or more sialylated O-glycans and the second polypeptide contains an amino acid sequence homologous or identical to a second mammalian, in particular human protein, wherein compared to the second polypeptide the composition has an increased binding affinity to a SIGLEC selected from to one or more SIGLECs, selected from SIG-5, SIG-7, SIG-8, and SIG-9.

It is also possible to provide a binding partner a polypeptide which has increased binding affinity to a SIGLEC, so that the complex of the two polypeptides has an increased binding affinity to the SIGLEC as compared to the polypeptide.

Thus, according to a third aspect the invention provides a composition comprising a first and a second polypeptide, wherein the first polypeptide is a glycosylated polypeptide containing one or more sialylated O-glycans and the second polypeptide contains an amino acid sequence homologous or identical to a second mammalian, in particular human protein, wherein compared to the second polypeptide:

- the composition has an increased binding affinity to a SIGLEC selected from; and/or
- the immune response of a human to the complex is reduced; and/or
- the immune tolerance of a human to the complex is increased.

The second human protein is preferably a human blood protein. The human blood protein may be a human blood clotting factor, a transport protein, a protease inhibitor, an immunoglobulin, a cell related plasma protein, an apolipoproteins, a complement factor, a growth factor, an antiangionetic protein, a highly glycosylated protein, blood factors or another human blood protein.

The human blood clotting factor is in particular selected from the group consisting of fibrinogen, fibrin monomer, prothrombin, thrombin, FV/FVa, FX/FXa, FIX/FIXa, FVII/FVIIa, FVIII/FVIIIa, FXI/FXIa, FXII/FXIIa, FXIII/FXIIIa, von Willebrand factor, and ADAMTS13.

The transport protein may be selected from albumin, transferrin, ceruloplasmin, haptoglobin, hemoglobin, and hemopexin.

Possible protease inhibitors are, e.g., ß-antithrombin, α-antithrombin, oxidized-antithrombin, 2-macroglobulin, CI-inhibitor, tissue factor pathway inhibitor (TFPI), heparin cofactor II, protein C inhibitor (PAI-3), Protein C, Protein S, and Protein Z.

Examples of immunoglobulin's such as polyclonal antibodies (IgG), monoclonal antibodies, IgG1, IgG2, IgG3, IgG4, IgA, IgA1, IgA2, IgM, IgE, IgD, and Bence Jones protein.

The cell related plasma protein may be for example, fibronectin, thromboglobulin, platelet factor 4. Examples of apolipoproteins are apo A-I, apo A-II, and apo E.

Complement factors according to the invention are e.g. Factor B, Factor D, Factor H, Factor I, C3b-Inactivator, properdin, C4-binding protein etc.

Examples of growth factors include Platelet derived growth factor (PDGF), Epidermal growth factor (EGF), Transforming growth factor alfa (TGF-α), Transforming growth factor beta (TGF-α), Fibroblast growth factor (FGF) and Hepatocyte growth factor.

Antiangionetic proteins include latent-antithrombin, prelatent-antithrombin, oxidized-antithrombin and plasminogen.

Examples of highly glycosylated proteins are alfa-1-acid glycoprotein, antichymotrypsin, inter-α-trypsin inhibitor, α-2-HS glycoprotein, C-reactive protein, Blood factors may be, e.g., such as erythropoeitin, interferon, tumor factors, tPA, gCSF.

Other human blood proteins include histidine-rich glycoprotein, mannan binding lectin, C4-binding protein, fibronectin, GC-globulin, plasminogen/plasmin, α-1 microglobulin, C-reactive protein.

The second human protein is in particular selected from vWF, FVIII, FVII/FVIIa, FIX, ADAMTS13.

The composition according to the third aspect is in particular a protein complex of the first and second polypeptide.

The first polypeptide is preferably glycosylated and contains one or more sialylated O-glycans. The second polypeptide contains an amino acid sequence identical to a mammalian, in particular human protein. In order to reduce the immune response of a human to the second polypeptide a first polypeptide forms a complex with the second polypeptide.

For protein complex formation, the first polypeptide in particular comprises a binding domain, that allows a binding to the second polypeptide and a glycosylation domain. The glycosylation domain in particular comprises one or more O-glycosylation sites, preferably an O-glycosylation cluster.

According to one embodiment, the second polypeptide is a FVIII protein and the first polypeptide comprises the FVIII binding domain of vWF and one or more O-glycosylation sites to which sialylated core 2 O-glycans are bound.

A preferred example of the composition is a protein complex of a FVIII protein with an amino acid sequence 95% identical to the sequence identified by amino acids 20 to 2.351 of P00451 and a first polypeptide as a binding partner comprising amino acid sequence at least 95% identical to amino acids 1 to 172 of SEQ ID NO: 1.

According to one embodiment of the protein complex of the third aspect the first polypeptide is a polypeptide according to the first aspect.

According to a further embodiment, the second polypeptide may for example be selected from FVIII, FVII, FIX and ADAMTS13.

In one embodiment of the third aspect, the first polypeptide comprises at least a fragment of human vWF and a second polypeptide is a FVIII protein, in particular a full length FVIII protein, a B-domain deleted FVIII protein or a FVIII protein in which part of the B-domain has been replaced by a linker. According to one embodiment the first polypeptide is defined by amino acids 1 to 505 of SEQ ID NO: 1, which was produced in HEK-cells, in particular HEK 293F-cells.

According to a further embodiment the first polypeptide is defined by amino acid 1 to 505 of SEQ ID NO: 1 and one copy of amino acids 475 to 505 of SEQ ID NO: 1. Moreover, the first polypeptide may be defined by an amino acid sequence selected from SEQ ID NO: 2, SEQ ID NO: 3, SEQ ID NO: 4, and SEQ ID NO: 5.

As shown in the examples, a protein with an improved binding affinity to SIGLECs, in particular SIG-5, SIG-7, SIG-8 and/or SIG-9 can be produced with the cell-line HEK 293F. Thus, according to a further embodiment of the protein complex the first and second polypeptides are produced by recommended expression in a human cell-line, preferably a HEK cell-line. Examples of HEK cell-lines for production of the glycosylated polypeptide are HEK 293 F, Flp-In™-293, 293, 293 EBNA, 293 H, 293S, 293T, 293T/17, 293T/17 SF, HEK 293 STF, and HEK-293.2sus. A preferred cell line for production of the polypeptide is the HEK 293 F as cell line.

The first and second polypeptide can be produced by separate recombinant expression and joined afterwards. Alternatively, the first and second polypeptide are recombinantly expressed in the same cell. For this, the first and second polypeptide may be encoded of the same vector or on two different vectors.

Polynucleotide

According to a fourth aspect, the invention provides an isolated polynucleotide that comprises a nucleic acid sequence encoding a glycosylated polypeptide according to the first aspect of the invention.

The isolated polynucleotide may be a DNA molecule or an RNA molecule. The isolated polynucleotide is preferably a DNA molecule, in particular a cDNA molecule. The techniques used to isolate or clone a polynucleotide encoding a peptide are known in the art and include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shared structural features (see, e.g., Innis et al, 1990) PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

The isolated polynucleotide may be a DNA molecule encoding a glycosylated polypeptide with an amino acid sequence similar or identical to a sequence selected from the group consisting of SEQ ID NO: 2, SEQ ID NO: 3, SEQ ID NO: 4, SEQ ID NO: 5.

In particular, the isolated polynucleotide may be a DNA molecule encoding a glycosylated polypeptide having an amino acid sequence with an identity of at least 90%, preferably at least 95%, more preferably at least 98%, most preferably 100% to SEQ ID NO: 2.

Moreover, the isolated polynucleotide may be a DNA molecule encoding a glycosylated polypeptide having an amino acid sequence with an identity of at least 90%, preferably at least 95%, more preferably at least 98%, most preferably 100% to SEQ ID NO: 3. According to one embodiment the isolated polynucleotide is a DNA molecule encoding a glycosylated polypeptide having an amino acid sequence with an identity of at least 90%, preferably at least 95%, more preferably at least 98%, most preferably 100% to SEQ ID NO: 4. According to one embodiment, the isolated polynucleotide is a DNA molecule encoding a glycosylated polypeptide having an amino acid sequence with an identity of at least 90%, preferably at least 95%, more preferably at least 98%, most preferably 100% to SEQ ID NO: 5.

Expression Vector

In a fifth aspect the invention also relates to a expression vector comprising a polynucleotide according to the fourth aspect of the invention.

The expression vector further preferably comprises control elements such as a promoter, and transcriptional and translational stop signals. The polynucleotide according to the fourth aspect and of the control elements may be joined together to produce a recombinant expression vector that may include one or more restriction sites to allow for insertion or substitution of the polynucleotide encoding the polypeptide at such sites. The polynucleotide may be inserted into an appropriate expression vector for expression. In creating the expression vector, the coding sequence is located in the expression vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide of the fourth aspect of the invention. The choice of the expression vector will typically depend on the compatibility of the expression vector with the host cell into which the expression vector is to be introduced. The expression vectors may be a linear or closed circular plasmid.

The expression vector is preferably adapted to expression in mammalian cells. The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. For autonomous replication, the vector may further comprise an origin of replication enabling the vector to replicate autonomously in the host cell in question. The origin of replication may be any plasmid replicator mediating autonomous replication that functions in a cell. The term “origin of replication” or “plasmid replicator” means a polynucleotide that enables a plasmid or vector to replicate in vivo.

The vector is preferably one that, when introduced into the host cell, is integrated into the genome and replicated together with the chromosome(s) into which it has been integrated. For integration into the host cell genome, the expression vector may rely on any other element of the expression vector for integration into the genome by homologous or non-homologous recombination. Alternatively, the vector may contain additional polynucleotides for directing integration by homologous recombination into the genome of the host cell at a precise location in the chromosome.

The vectors of the present invention preferably contain one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

The procedures used to ligate the elements described above to construct the recombinant expression vectors of the present invention are well known to one skilled in the art (see, e.g., Sambrook et al., 1989, supra).

According to one embodiment the vector backbone of the vector according to the fifth aspect is selected from pCDNA3, pCDNA3.1, pCDNA4, pCDNA5, pCDNA6, pCEP4, pCEP-puro, pCET1019, pCMV, pEF1, pEF4, pEF5, pEF6, pExchange, pEXPR, pIRES, and pSCAS.

The vector according to the fifth aspect may be transiently or intransiently transformed into an host cell. The host cell may any of the cells listed above. Preferably the host cell is HEK 293F.

Medical Use and Method of Treatment

As described above, the glycosylated polypeptide and the composition, in particular protein complex according to the invention have the advantage of a reduced immune response in patients, in particular human patients. Thus, a glycosylated polypeptide and a protein complex are in particular useful as active ingredients for medical treatment.

According to a sixth aspect the invention provides a glycosylated polypeptide defined according to the first aspect for use in medical treatment. As an alternative, according to the sixth aspect the invention provides a composition defined according to the third aspect for use medical treatment. Preferably, the treatment or prevention of a bleeding disorder.

Thus, the sixth aspect of the invention also relates to a method of treatment or prevention of a bleeding disorder of a patient, said method comprising administering to said patient a glycosylated polypeptide according to the first aspect or a composition, in particular protein complex according to the third aspect.

As used herein "bleeding disorder" refers to a disease or condition that impairs normal hemostasis. The bleeding disorder can be, for example, Hemophilia A, Hemophilia B, Factor VIII deficiency, Factor XI deficiency, von Willebrand Disease, Glanzmann's Thrombasthenia, Bernard Soulier Syndrome, idiopathic thrombocytopenic purpura, intracerebral hemorrhage, trauma, traumatic brain injury, and the like.

As used herein, "hemophilia" refers to a group of bleeding disorders associated with increased blood clot formation time as compared to blood clot formation time in healthy individuals without hemophilia. "Hemophilia" refers to both Hemophilia A, which is a disorder that leads to the production of defective Factor VIII, and Hemophilia B, which is a disorder that leads to the production of defective Factor IX.

The bleeding disorder is preferably haemophilia. The treatment may for example be the haemophilia treatment of PUPS (Previously untreated patients) or an immune tolerance induction (ITI) treatment.

According to an alternative embodiment of the third aspect the invention provides a protein complex defined according to the second aspect for use in the treatment or prevention of a bleeding disorder.

The treatment preferably comprises administering to a patient an effective amount of the glycosylated polypeptide or composition, in particular protein complex.

The glycosylated polypeptide or composition, in particular protein complex, described herein can be administered alone or in the form of pharmaceutical compositions.

Pharmaceutical compositions according to the invention may comprise an effective amount of the conjugates formulated with at least one pharmaceutically acceptable carrier. Pharmaceutical compositions of the embodiments can be prepared and administered to a subject by any methods well known in the art of pharmacy. See, e.g, Goodman & Gilman's The Pharmacological Basis of Therapeutics, Hardman et al., eds., McGraw-Hill Professional (10th ed., 2001); Remington: The Science and Practice of Pharmacy, Gennaro, ed., Lippincott Williams & Wilkins (20th ed., 2003); and Pharmaceutical Dosage Forms and Drug Delivery Systems, Ansel et al. (eds), Lippincott Williams & Wilkins (7th ed., 1999). In addition, the pharmaceutical compositions of the embodiments may also be formulated to include other medically useful drugs or biological agents. The pharmaceutical composition typically comprise a therapeutically effective amount of the glycosylated polypeptide or protein complex combined with a pharmaceutically acceptable carrier. The pharmaceutically acceptable carrier is any carrier known or established in the art. Exemplary pharmaceutically acceptable carriers include sterile pyrogen-free water and sterile pyrogen-free saline solution. Other forms of pharmaceutically acceptable carriers that can be utilized for the present embodiments include binders, disintegrants, surfactants, absorption accelerators, moisture retention agents, absorbers, lubricants, fillers, extenders, moisture imparting agents, preservatives, stabilizers, emulsifiers, solubilising agents, salts which control osmotic pressure, diluting agents such as buffers and excipients usually used depending on the use form of the formulation. These are optionally selected and used depending on the unit dosage of the resulting formulation.

For in vivo applications, the glycosylated polypeptide, protein complex or pharmaceutical composition can be administered to the patient by any customary administration route, e.g., orally, parenterally or by inhalation. Parenteral administration includes intravenous injection, subcutaneous injection, intraperitoneal injection, intramuscular injection and intraperitoneal injection, liquid agents, suspensions, emulsions and dripping agents. For parenteral administration the glycosylated polypeptide, protein complex or pharmaceutical composition should be an injectable agent such as a liquid agent or a suspension.

In other embodiments, the glycosylated polypeptide, protein complex or pharmaceutical composition is administered orally to a patient. In these embodiments, a form of the drug includes solid formulations such as tablets, coated tablets, powdered agents, granules, capsules and pills, liquid formulations such as liquid agents (e.g., eye drops, nose drops), suspension, emulsion and syrup, inhales such as aerosol agents, atomizers and nebulizers, and liposome inclusion agents. In still some other embodiments, the glycosylated polypeptide, protein complex or pharmaceutical composition is administered by inhalation to the respiratory tract of a patient to target the trachea and/or the lung of a subject. In these embodiments, a commercially available According to one embodiment of the sixth aspect the glycosylated polypeptide or composition, in particular protein complex for use, the use comprises an intravenous or non-intravenous injection. The non-intravenous injection preferably is a subcutaneous injection.

The invention will further be described by the following non-limiting examples.

EXAMPLES

Example 1—Binding Von Full Length Willebrand Factor (vWF) to SIGLECs 1.1. Experimental Procedure Recombinant SIG-2, SIG-5, SIG-7, SIG-F (mouse equivalent of human SIG-8), SIG-9 and SIG-10 were obtained as Fc-fusion proteins from R&D Systems. First, Protein A (SERVA Feinbiochemica GmbH & Co) was coated on a plate in a concentration 0.5 µg/well, at 4° C., over night (0/N). After blocking and washing steps with washing buffer (20 mM HEPES, 125 mM NaCl, 1 mM EDTA, 1% BSA), Fc-fusion SIGLECs or control antibodies, were bound to protein A by 1 h incubation at 37° C. at 5 µg/ml concentration. Anti vWF-pAb (Dako, #A0082) was immobilized as a positive control and Anti-Chicken IgY (Sigma Aldrich, #C2288) as a negative control via antibody Fc part.

Plasma derived VWF (pdVWF), was biotinylated using EZ-Link™ Sulfo-NHS-Biotin biotinilation kit (Thermo Fisher Scientific). Concentration series of biotinylated, vWF was applied into the wells at concentrations of 0 to 0.8 µg/mL. After five washing steps with washing buffer, the HRP-coupled streptavidin (Thermo Fisher Scientific, #31001) was added to the wells and incubated 1 h at 37° C. with subsequent five washing steps.

For visualization of the bound biotinylated pdvWF the well were incubated with o-Phenylenediamine dihydrochloride substrate (SIGMAFAST™ OPD, #P9187, Sigma Aldrich). Subsequently the absorbance at 492 nm was measured.

1.2 Results

Figure 1:
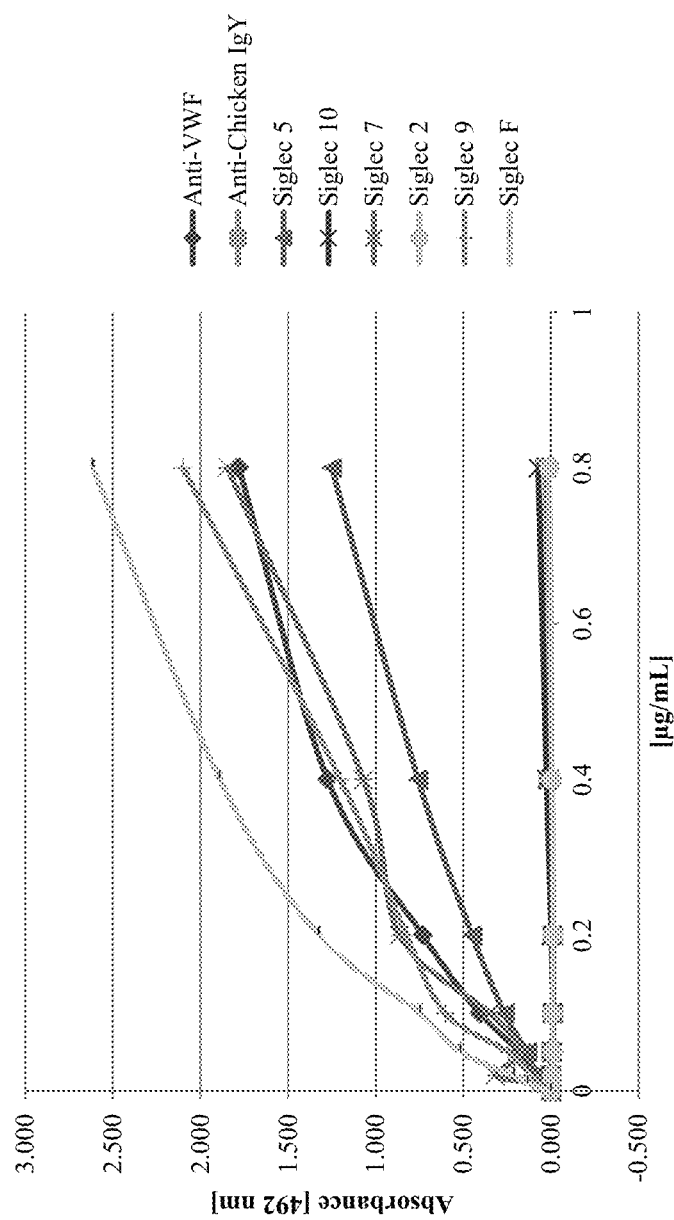

As shown in FIG. 1 the absorbance at 492 nm increases with the starting concentration of vWF in the binding experiments with SIG-5, SIG-7, SIG-F, and SIG-9. The values are slightly above (SIG-F and SIG-9) or below (SIG-5 and SIG-7) the positive control (anti-vWF). In contrast, the absorbance in the binding experiments with SIG-2, SIG-10 and the negative control Anti-Chicken IgY was around 0 independent of the concentration.

Accordingly, vWF binds to SIG-5, SIG-7, SIG-F, and SIG-9 in a concentration-dependent manner. On the other hand vWF does not bind to SIG-2 and SIG-10.

Example 2—Binding of vWF Fragments to SIGLECs 2.1 Experimental Procedure

C- and N-terminal fragments of vWF were prepared by V8 protease (Thermo Fisher Scietific, #201959)] digestion performed for 3 h, 37° C., 300 rpm, using 1:100 enzyme to protein w/w ratio in a 50 mM Tris-HCl, 150 mM NaCl pH 7.8 buffer and purified by anion exchange chromatography on a MonoQ 5/50 GL column (GE Healthcare #17-5166-01). The running buffer was 20 mM Tris-HCl pH 7.4, and the elution buffer 20 mM Tris-HCl, 500 mM NaCl pH 7.4. Fragments were further purified and desalted by size exclusion chromatography on a Superose 6 10/300 GL column (GE Healthcare #17-5172-01) using 100 mM NaCl as a running buffer.

Figure 2:
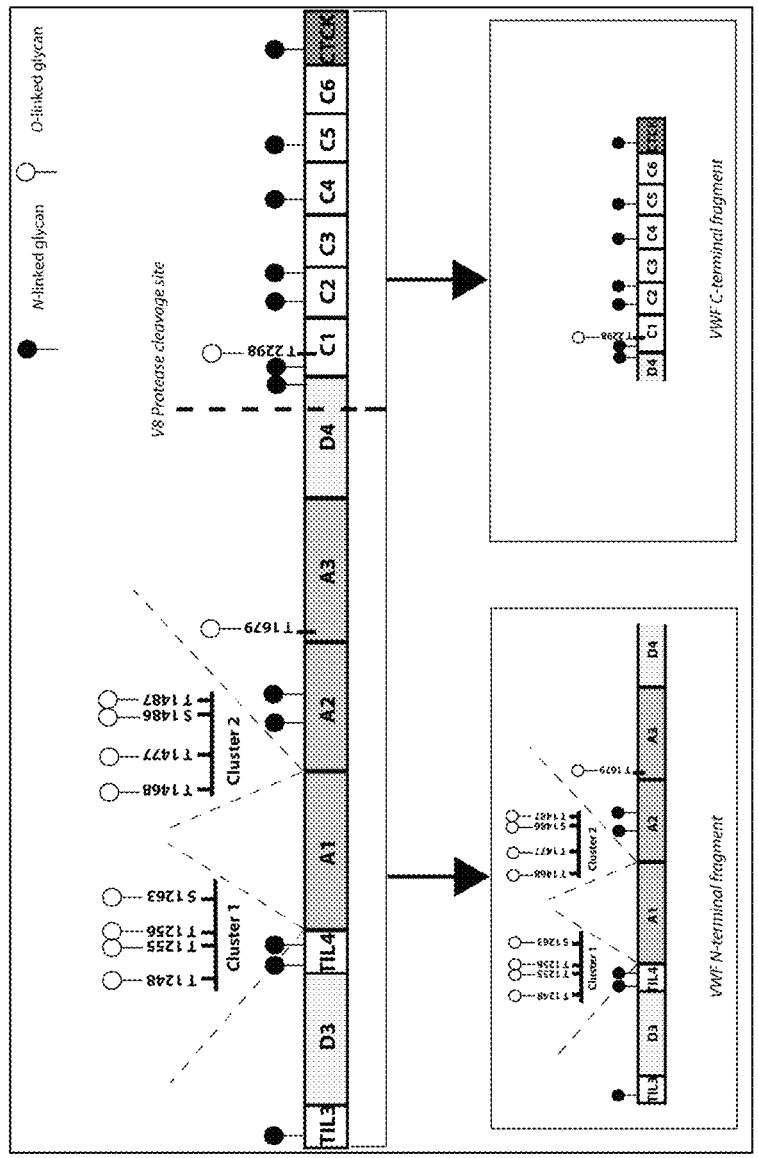

The obtained fragments (C-terminal and N-terminal) are schematically depicted in FIG. 2 with an identification of domains and glycosylation sites.

The purified vWF C-terminal fragment and vWF N-terminal fragment were biotinylated using EZ-Link™ Sulfo-NHS-Biotin biotinilation kit (Thermo Fisher Scientific) and the binding to SIGLECs was measured as described in example 1 with a concentration of the vWF C-terminal fragment and vWF N-terminal fragment of 1 µg/mL.

2.2 Results

Figure 3:
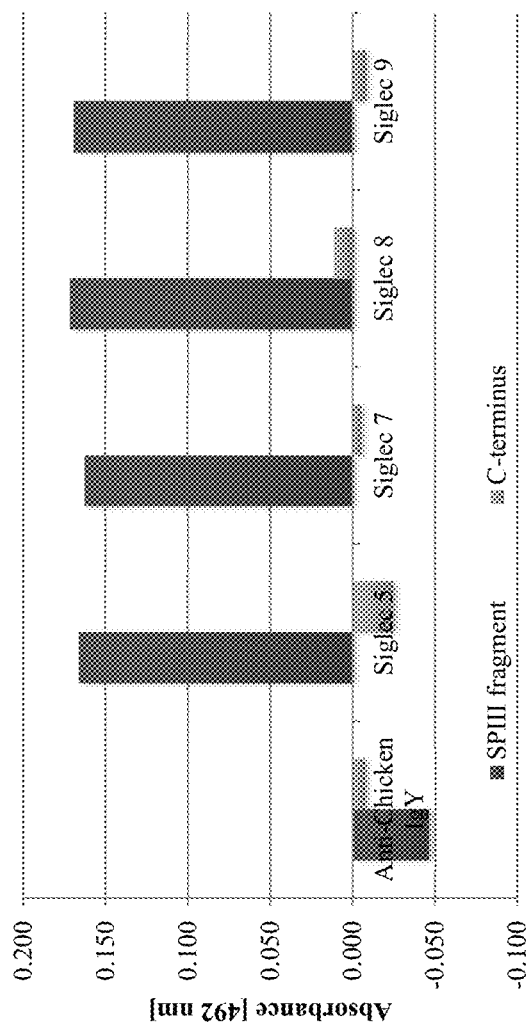

Based on the absorbance values shown in FIG. 3, the vWF N-terminal fragment which contains the majority of the O-glycosylation sites and 2 O-glycan clusters (Cluster 1 and Cluster 2) binds to SIG-5, SIG-7, SIG-F and SIG-9. In contrast, little or no absorbance was measured for the vWF C-terminal fragment. Accordingly the latter fragment does not bind to the SIGLECs.

Example 3—Binding of N-Terminal Part of vWF to SIGLECs 3.1. Experimental Procedure One portion of the N-terminal vWF fragment obtained in example 2 was enzymatically desialylated using SialidaseA. The incubation was performed at 37° C. for 3 h in 50 mM sodium phosphate, pH 6.0 using 2 µl enzyme for 100 µg VWF fragment (Sialidase A™ #GK80040 was obtained from Prozyme).

A second portion of the N-terminal vWF fragments was de-N-glycosylated. The incubation was performed over night at 37° C. in 50 mM Sodium Phosphate pH 7.5 buffer using 1 µl enzyme for 20 µg VWF fragment (PNGaseF #P0704 was obtained from New England Biolabs).

Samples of the desialylated, the de-N-glycosylated and the untreated N-terminal vWF fragment were tested for binding to SIG-5, SIG-7, SIG-8, and SIG-9. The binding experiment was carried out as described in Example 1 with a concentration of the N-terminal vWF fragments of 8 µg/mL.

Figure 4:
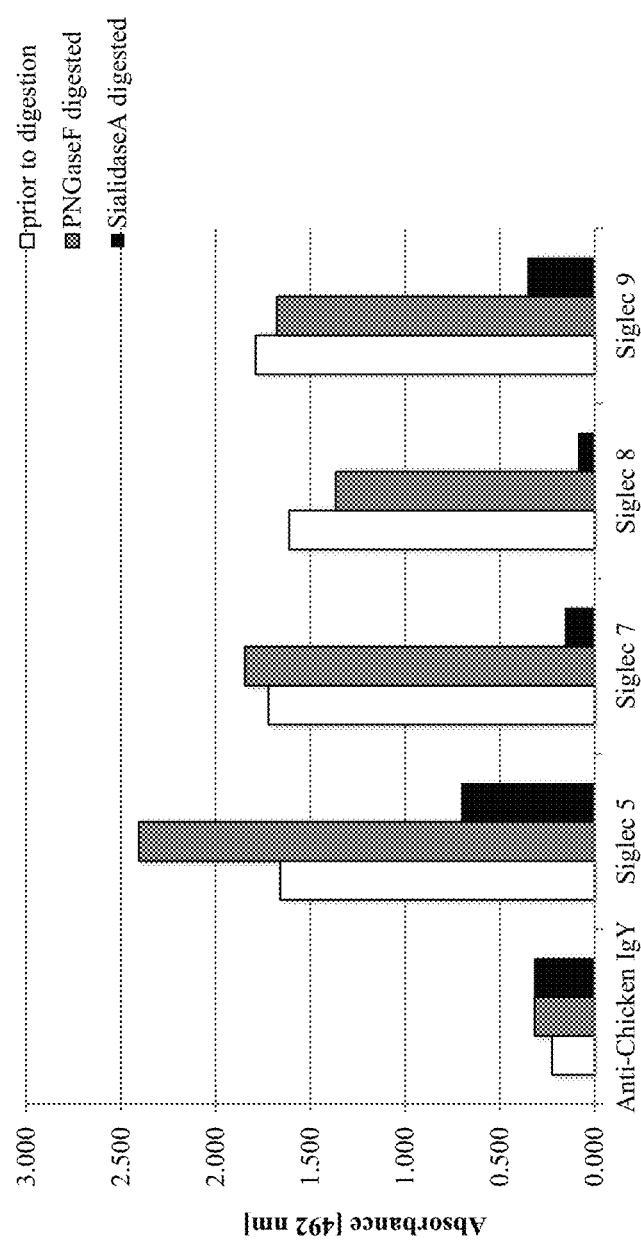

3.2 Results:

As shown in FIG. 4 the absorbance values determined for the de-N-glycosylated vWF N-terminal fragment and the untreated vWF N-terminal fragment differs only slightly. Thus, de-N-glycosylation does not influence the binding showing that the binding is mediated via O-glycans.

Desialylation of O-glycans strongly reduces or abolishes the binding of the vWF N-terminal fragment to SIGLECs as shown in FIG. 4. Thus, the binding of the vWF N-terminal fragment is mediated by the sialic acid attached to O-glycan chains.

Example 4—SIGLEC Binding of Peptides Containing O-Glycan Clusters 1 and 2

4.1 Experimental Procedure vWF contains two clusters of fully occupied O-glycosylation sites (cf. Solecka et. al 2016), schematically depicted in FIG. 2. Both clusters differ in the relative amount of core 2 structures. Only 4.9% of the glycopeptide molecules contain core 2 structures in Cluster 1. Accordingly, the percentage of sialylated core 2 O-glycans based on the total number of O-glycans in cluster 1 is 1.25%.

On the other hand 34.86% of the glycopeptide molecules contain core 2 structures in Cluster 2 (cf. Solecka et al, 2016). Accordingly, the percentage of sialylated core 2 O-glycans based on the total number of O-glycans in cluster 2 is 10.78%.

To measure the binding of the two clusters independently the vWF N-terminal fragment was treated with Trypsin, producing the following fragment: Cluster 1 fragment encompassing AA 449 to 511 and Cluster 2 fragment encompassing AA 674 to 728/729 of VWF of SEQ ID NO: 1. The fragments were purified by reverse-phase HPLC. Briefly, pdVWF was reduced and free cysteines were blocked with Maleimide-PEG2-Biotin according to manufacturer's instruction (EZ-Link™ Maleimide-PEG2-Biotin, #21901BID) was obtained from Thermo Fisher Scientific). After digestion with trypsin at 37° C. over night, high molecular weight peptides were concentrated using 10 kDa cut off centrifugal filter device (Millipore). Subsequently peptides were separated on a Jupiter 5μ 300 Å C18 column (Phenomenex). The mobile phase was: A—0.1% trifluoroacetic acid (TFA) in H2O; B—0.085% TFA in acetonitrile and the flow rate was 0.3 mL/min. Eluting peptides/glycopeptides were detected by ultraviolet absorption at 215 nm wavelength. Fractions of interest were collected, freeze-dried and subsequently reconstituted in 10 μL H$_2$O. Since both clusters contain cysteines, both were supplied with a biotin.

A binding experiment was carried out as described in Example 1 with the SIGLECs SIG-5, SIG-7, SIG-F, SIG-9 and SIG-10 and a concentration of the cluster 1 and cluster 2 fragments of 4 μg/mL.

Additionally, a sample of the cluster 1 and cluster 2 fragments were treated by desialysation and subsequently tested in a binding experiment as described in Example 1 with a concentration of the desialylated cluster 1 and cluster 2 fragments of 2 μg/mL.

Figure 5:
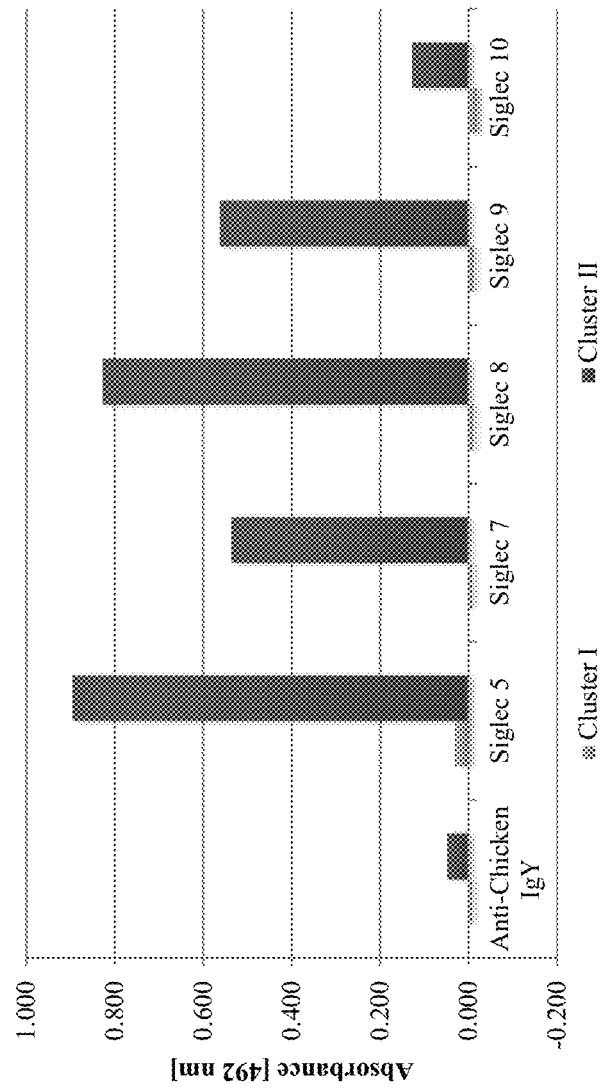

4.2 Results:

The cluster 2 fragment bound to SIGLECs SIG-5, SIG-7, SIG-F, SIG-9 based on the absorbance values shown in FIG. 5. No or little absorbance was detected with SIG-10, confirming the results from the other examples.

Consequently a high percentage of core 2 structures on O-glycan clusters is a requirement for binding SIG-5, SIG-7, SIG-F, SIG-9.

Example 5—Sialic Acid Dependency of Cluster 2 SIGLEC Binding 5.1 Experimental Procedure A sample of the cluster 2 fragment obtained as described in Example 4 was desialylated. The desialylated cluster 2 fragments and the untreated cluster 2 fragments were subsequently tested in a binding experiment as described in Example 1 with the SIGLECs SIG-5, SIG-7, SIG-F, and SIG-9 and a concentration of the desialylated Cluster 1 and Cluster 2 fragments of 2 μg/mL.

5.2 Results

Figure 6:
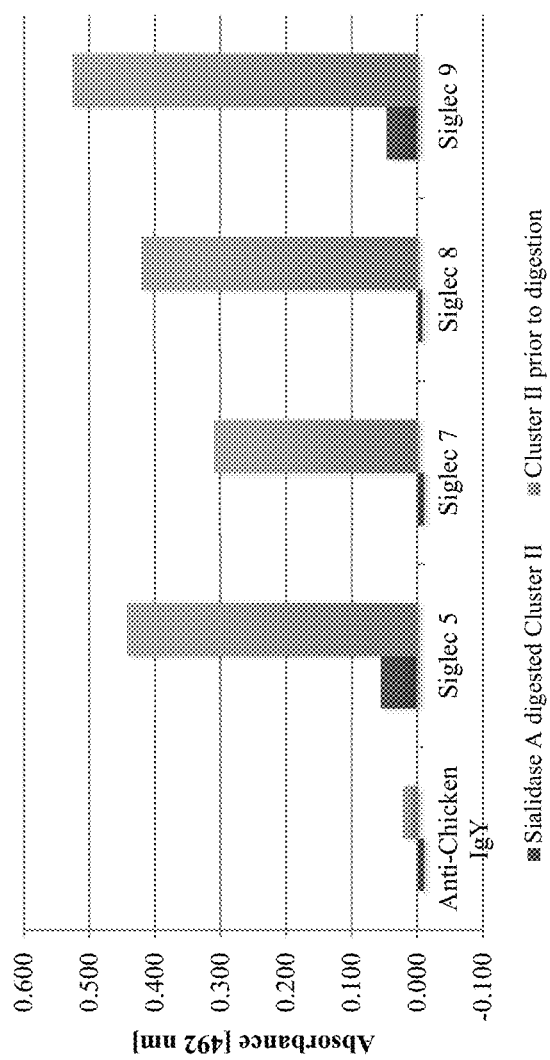

The absorbance values detected for the untreated cluster 2 fragment confirmed the results found in Example 4 (see FIG. 6). De-sialylated cluster 2 fragment exhibits no or only little binding. Thus, sialylation of the core 2 structures on O-glycan clusters is a requirement for binding to SIG-5, SIG-7, SIG-F, SIG-9.

Example 6—Recombinant Expression of VWF Fragments with or without O-Linked Glycan Repeats Containing FVIII Binding Site Two recombinant vWF fragments were expressed in HEK cell line 293 F. The first fragment, Seq11 encompasses AA 1-505 of SEQ ID NO: 1 and contains Cluster 1 with the O-glycosylation sites 485, 492, 493, 500).

The second fragment Seq12 encompasses AA 1 to 505 of SEQ ID NO: 1 and 2 additional repetitions of the AAs 475-505 (AA1-505+2× 475-505) and thus two additional copies of Cluster 1 O-glycan cluster repeats.

Seq11 and Seq12 were transiently expressed in HEK293 cell line with a C-terminal Strep-Tag and purified by Strep-tactin affinity chromatography (IBA GmbH). Therefore, the genes encoding Seq11 and 12, were synthesized by GeneArt (Thermo Fisher Scientific) and cloned in the pDSG-expression vector (IBA GmbH), containing a Twin-Strep-tag. TOP10 *E. coli* (IBA gmbH) were transformed with the constructs and single clones were selected following an overnight incubation at 37° C. on ampicillin-containing LB-agar plates. Plasmid DNA preparations were performed using the QIAamp DNA-Mini or Maxi kit (Qiagen) according to the manufacturer's recommendations. The correct orientation and integrity of the cloned constructs was verified by sequencing. For eukaryotic expression of both vWF fragments, MEXi-293 cells (IBA GmbH) grown in MEXi transfection-medium (IBA GmbH), were transfected with 1.5 mg/l of the constructs using 4.5 mg/ml 25 kDa linear polyethylenimine. After 2-4 hour incubation at 37° C., 5% CO$_2$ and 100-150 rpm, the culture was diluted 1:2 with MEXi transfection-medium and cultivation was continued until cell viability reached 75%. Subsequently, the supernatant was separated from cells by centrifugation at 4° C. and 300×g. In order to minimize the inhibitory effect of biotin in the cell culture medium and to adjust the pH, 0.1 volumes of buffer (1M Tris-HCl, 1.5 mM NaCl, 10 mM EDTA, pH 8.0) and 0.09% (v/v) BioLock solution (IBA GmbH) was added to the supernatant and incubated for 20 min at 4° C. After centrifugation, the supernatant was applied on the Strep-Tactin XT column (IBA GmbH), washed five times with washing buffer (100 mM Tris-HCl, 150 mM NaCl, 1 mM EDTA, pH 8.0) and bound Strep-tag containing proteins were eluted with elution buffer (100 mM Tris-HCl, 150 mM NaCl, 1 mM EDTA, 10 mM desthiobiotin, pH 8.0).

Figure 7:
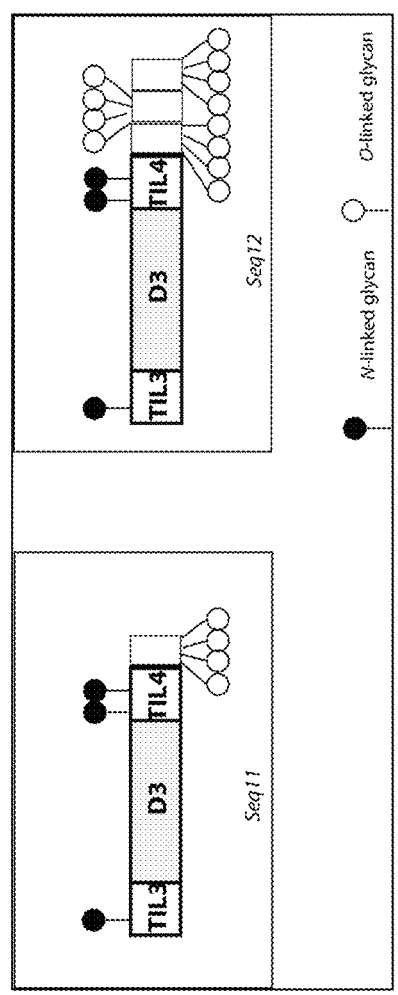

Both fragments Seq11 and Seq12 are schematically depicted in FIG. 7.

Example 7—Analysis of the O-Glycosylation of vWF Fragments Seq11 and Seq12

7.1 Experimental Procedure

O-glycosylation of the fragments Seq11 and Seq12 produced according to Example 6 was analyzed by mass spectrometry.

For this, Seq11 and Seq12 were first reduced and alkylated by incubation with 50 mM dithiothreitol at 60° C. and subsequently 20 min with 100 mM iodoacetamide. After digestion with tryptsin and chymotrypsin obtained peptides were re-buffered in SialidaseA digestion buffer and desialylated over night using conditions described in Example 3. The O-glycopeptides were specifically enriched by Jacalin (*Artocarpus integrifolia* lectin) affinity chromatography using agarose immobilized lectin (Vector Laboratories). Jacalin-agarose was packed into a gravity-driven column and the chromatography was performed according to the manufacturer's instructions. Eluted O-glycopeptides were purified for a MALDI MS measurement using C4 Ziptip pipette tips (Millipore) and subjected to a measurement in a linear positive ion mode using 25 mg/ml super DHB matrix dissolved in 50% Acetonitril/0.1% trifluoroacetic acid.

An aliquot of enriched glycopeptides was additionally treated with O-glycosidase (Endo-α-N-Acetylgalactosaminidase, #P0733. New England Biolabs). Briefly, peptides were incubated with the enzyme for 2 h at 37° C. using 1 μl enzyme for 10 μl glycoprotein. Since the O-glycosidase is specific for core 1 O-glycans only (Galβ1→3 GalNAcα1→Ser/Thr disaccharide) it leaves core 2 glycans and/or extended core 1 O-glycans attached to the peptide backbone.

7.2 Results

Figure 8:
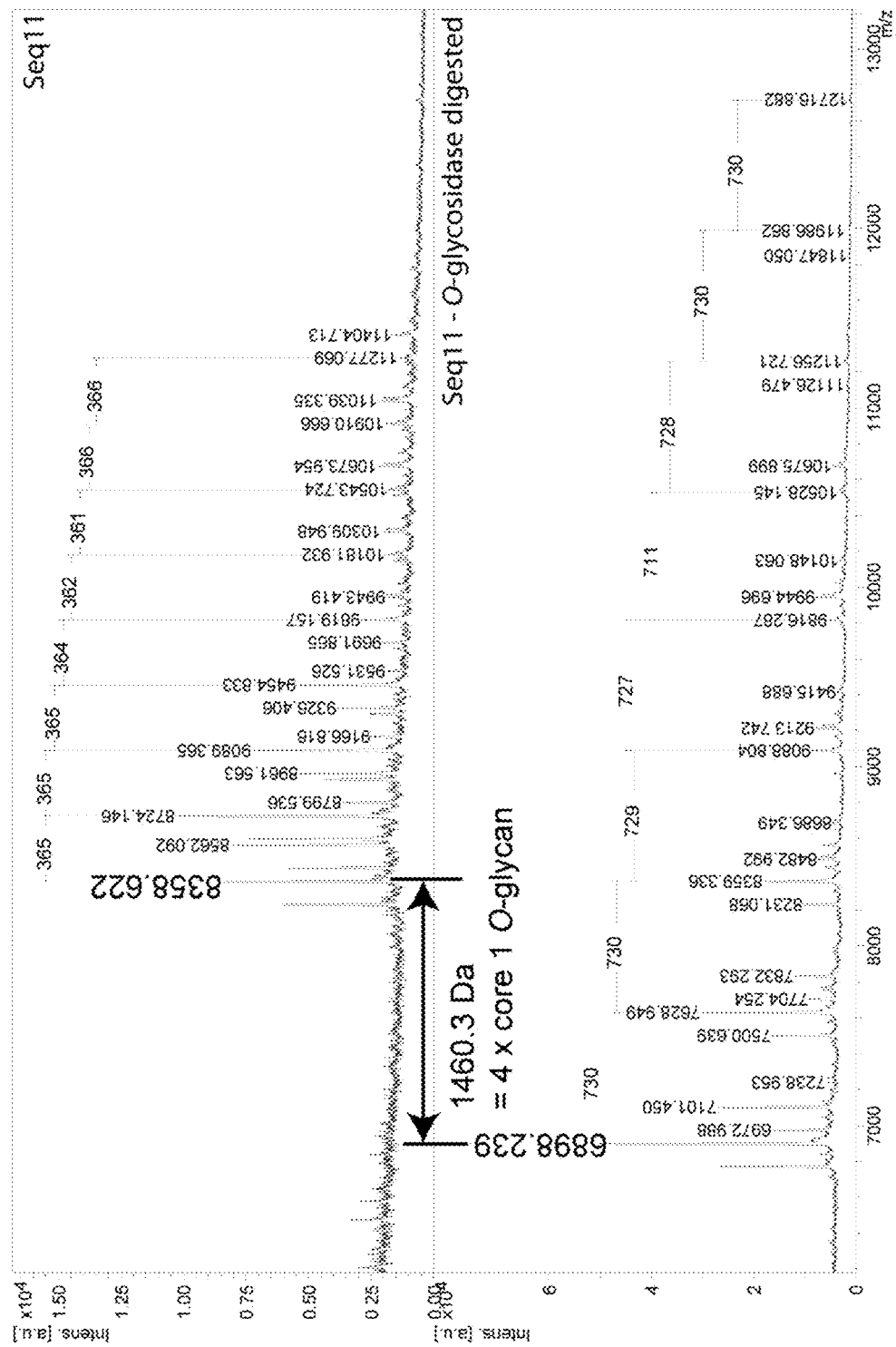
Figure 9:
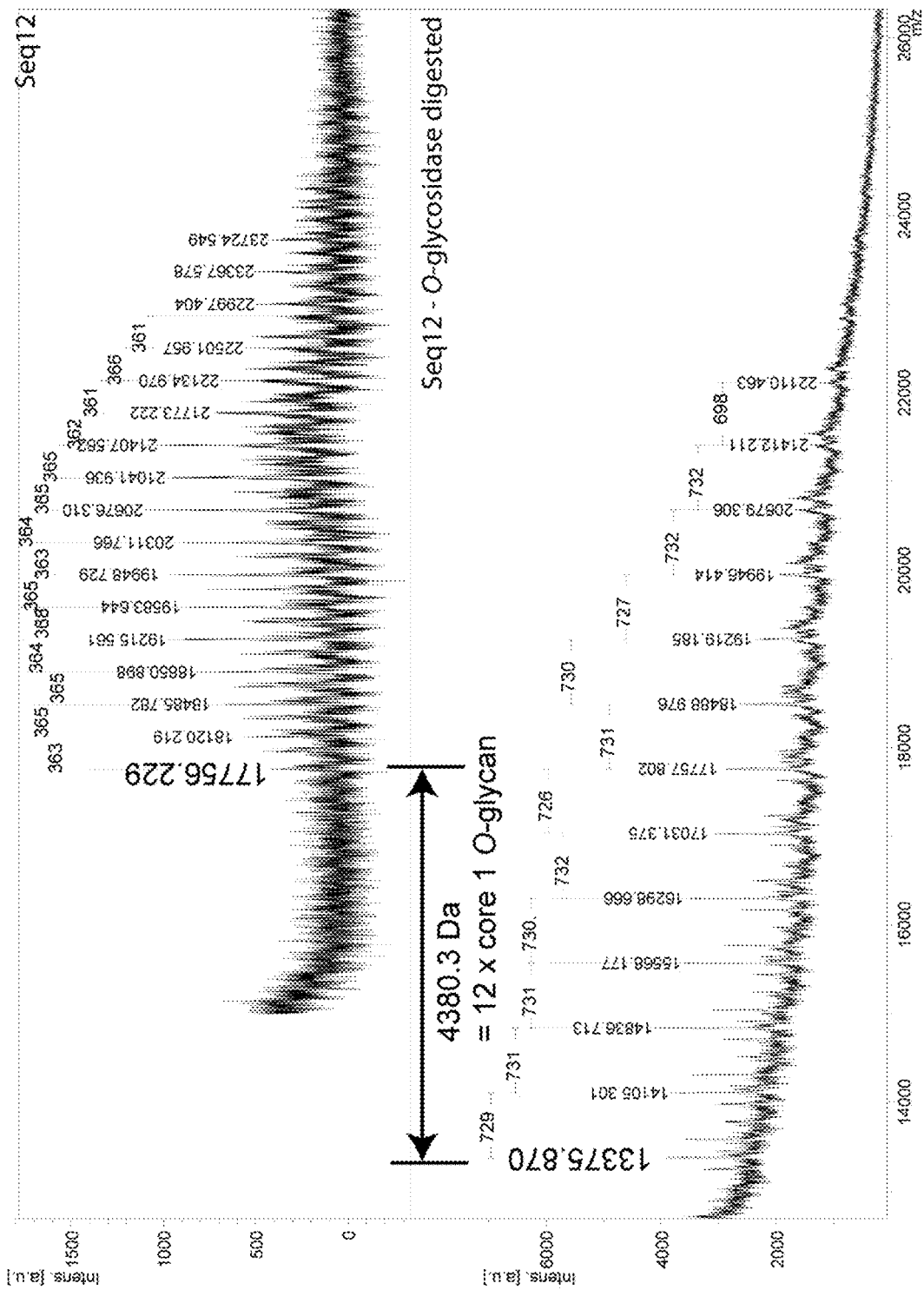

The results are summarized in FIGS. 8 and 9.

The O-glycopeptides were identified by a post source decay (PSD) MALDI. The peptide sequence of the identified Seq11 fragment is KVTLNPSDPEHCQICHCDWNLTCEACQEPGGLVVPPTDAPVSPTTLYVEDISEPPLH GSAW (SEQ ID NO: 6). The last four amino acids (underlined) correspond to the C-terminal Strep-Tag. This peptide contains four O-glycosylation sites.

The upper spectrum of FIG. 8 shows the fully O-glycosylated glycopeptide, the lower spectrum of FIG. 8 shows the same glycopeptide after O-glycosidase digestion. The 1460.3 Da mass shift after O-glycosidase digestion (marked by an arrow), corresponds to four core 1 O-glycans each with a mass of 365 Da. 365 Da mass distances, observed in the upper spectrum, correspond to different glycoforms of the same paptide, whereas each additional 365 Da mass adduct corresponds to a Galβ1→4GlcNAc disaccharide forming core 2 structure. After O-glycosidase treatment, completely deglycosylated form o the peptide (8358.6 Da) and glycoforms containing core 2 structures (Galβ1→4GlcNAcβ1→6(Galβ1→3)GalNAc, 730 Da) and/or extended core 1 structures (Galβ1→4GlcNAcβ1→3Galβ1→3GalNAc, 730 Da) are observed.

The identified peptide sequence of the Seq12 fragment is KVTLNPSDPEHCQICHCDWNLTCEACQEPGGLVVPPTDAPVSPTTLYVEDISEPPLH QEPGGLWPPTDAPVSPTTLYVEDISEPPLHQEPGGLWPPTDAPVSPTTLYVEDISEP PLHGSAW (SEQ ID NO: 7). The last four amino acids (underlined) correspond to the C-terminal Strep-Tag.

The upper spectrum of FIG. 9 shows the fully O-glycosylated glycopeptide, the lower spectrum of FIG. 9 shows the same glycopeptide after O-glycosidase digestion. The 4380.3 Da mass shift after O-glycosidase digestion, corresponds to twelve core 1 O-glycans each with a mass of 365 Da, which confirms, that all twelve O-glycosylation sites in Seq12 are occupied by O-glycans. Similarly as observed for Seq11, 365 Da and 730 Da distances observed in the spectra correspond to the Galβ1→4GlcNAc disaccharide or core 2 and/or extended core 1 structures respectively.

Quantitation of core 1 and core 2 type O-glycans is based on the relative quantity of the glycopeptides with the respective O-glycan attached. The quantitation of the different glycoforms of a given peptide is done by evaluation of the signal intensity in the MALDI spectrum.

For the glycopeptide Seq11 the quantitation is done based on the MALDI Signal intensity of the different glycoforms of the same peptide. The total peak intensity of all glycoforms of this peptide (8358 Da, 8724 Da, 9089 Da, 9454 Da, 9819 Da, 10181 Da, 10543 Da, 10910 Da, 11277 Da) equals 41275 a.u., which represents 100%.

The glycoform containing only core 1 glycans with a mass 8358 Da exhibits an intensity of 8410 a.u., which corresponds to 20% of the total. Thus, all other glycoforms (80%) contain at least one core 2 and/or extended core 1 glycan type glycan attached. In this measurement core 2 and extended core 1 are not distinguishable. Accordingly, the percentage of core 2 and/or extended core 1 O-glycans based on the total number of O-glycans is at least 20%.

Accordingly the four O-glycosylation sites in Seq11 and all twelve O-glycosylation sites in Seq12 recombinantly produced in a HEK cell line, are occupied with core 1 O-glycans and to a high percentage also with core 2 O-glycans and/or extended core 1 O-glycans. Considering high amount of core 2 O-glycans both sequences can be good ligands for SIGLEC binding. The addition of two additional sequence repeats, containing four O-glycosylation sites, resulted successfully in a protein with twelve clustered and fully occupied O-glycans.

Example 8—Analysis SIGLEC Binding of Seq11 and Seq12

8.1 Experimental Procedure

Strep-Tag bearing recombinant proteins Seq11 and Seq12 were tested in the SIGLEC binding ELISA as described in Example 1 except for the detection strategy; instead of the Streptavidin-HRP, Strep-Tactin-HRP (#2-1502-001, IBA GmbH) conjugate was used for detection of the Strep-tagged proteins. The concentration of the applied Strep-Tactin-HRP was 0.25 μg/ml. Both prots, Seq11 and Seq12 were tested in equal molar concentration of 42 nM.

8.2 Results

Figure 10:
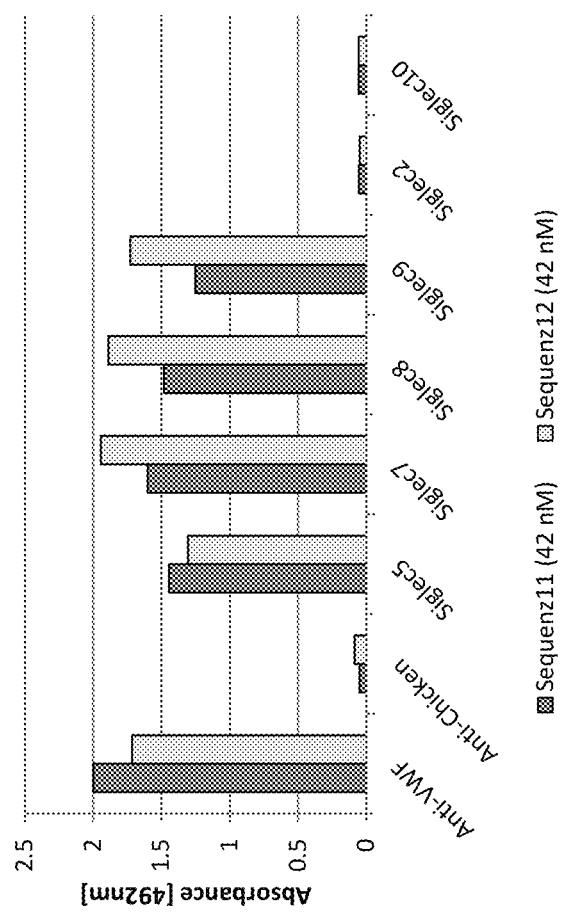

As shown in FIG. 10, both polypeptides Seq11 and Seq12 exhibited a binding to SIG-5, SIG-7, SIG-F and SIG-9. The measured absorbance for both polypeptides Seq11 and Seq12 to all four SIGLECs was in the same as range as the binding of Seq11 and Seq12 to anti-vWF.

In contrast, the absorbance of Seq11 and Seq12 in the experiment with SIG-2 and SIG10 was in the same range in the negative control experiment with anti-chicken antibody. Thus, neither did Seq11 nor Seq12 bind to SIG-2 or to SIG-10 (see FIG. 10).

Example 9—Sialic Acid Dependency of SIGLEC Binding of Seq11 and Seq12

9.1 Experimental Procedure

The experimental protocol according to example 8 was repeated with the addition of a SialidaseA digestion of the strep-tagged polypeptides Seq11 and Seq12. The desialylation was carried out as described in Example 3.

9.2 Results

Figure 11:
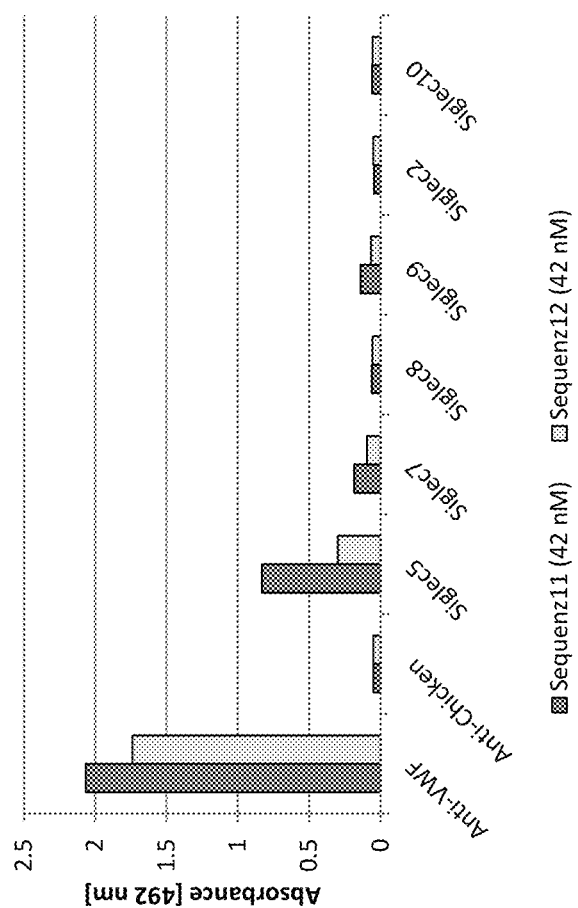

The results of the binding experiments with desialylated Seq11 and Seq12 are shown in FIG. 11. According to the measured absorbances the binding of desialylated Seq11 and Seq12 to SIG-5 is strongly reduced in comparison to the untreated polypeptides. The binding to SIG-7, SIG-F and SIG-9 is completely abolished, i.e. the absorbance is at the same level as determined for binding to SIG-2 and SIG10. Thus, binding of both polypeptides Seq11 and Seq12 to SIG-5, SIG-7, SIG-F and SIG-9 is a sialic acid dependent.

Example 10—Comparison of SIGLEC Binding of Seq11 and Seq12

10.1 Experimental Procedure

In order to measure and compare the apparent biding affinities of Seq11 and Seq12, SIGLEC ELISA with Scatchard analysis of the binding curves was applied. The ELISA was performed as described in Examples 8 and 9. Scachard analysis was done using Graph Pad Prism software.

10.2 Results

Figure 12:
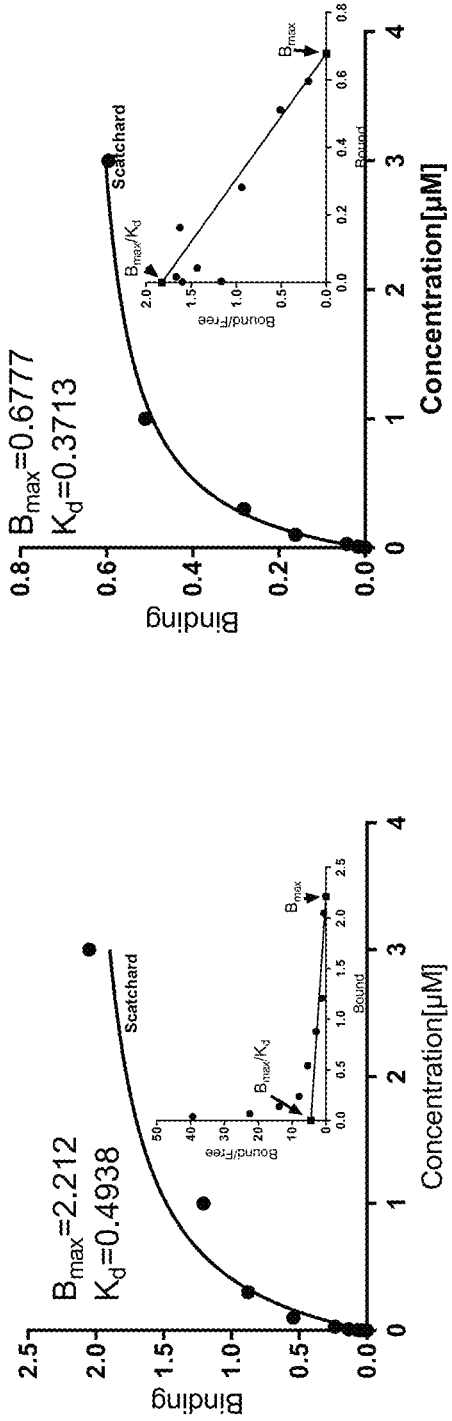
FIG. 12 shows the results of a concentration dependent binding of recombinant polypeptide Seq11 to SIGLECs and Scachard analysis of the specific binding curves.
Figure 12:
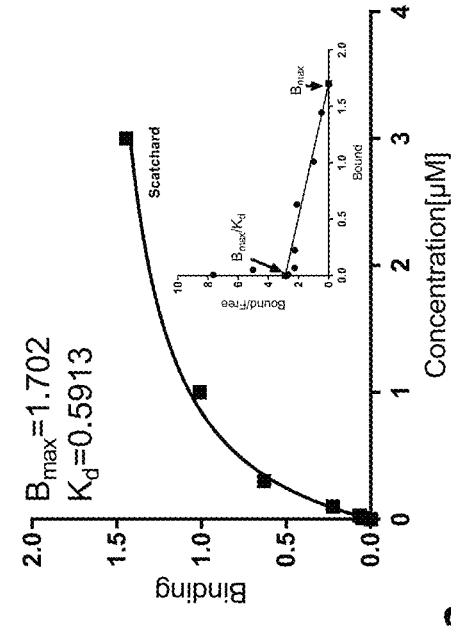
Figure 12:
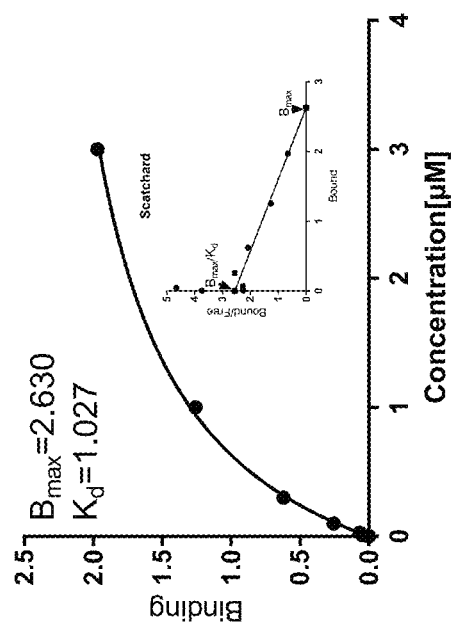
Figure 13:
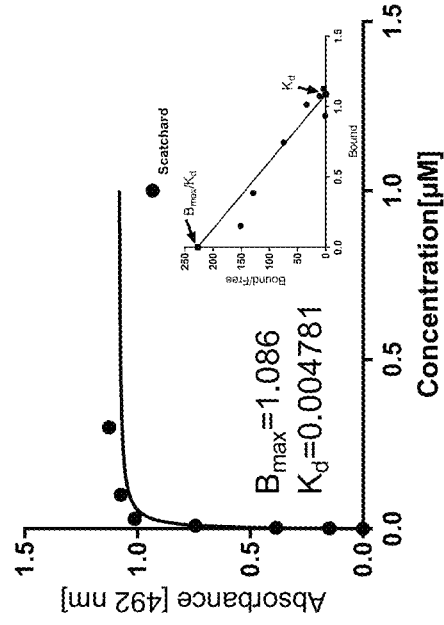
FIG. 13 shows the results of a concentration dependent binding of recombinant polypeptide Seq12 to SIGLECs and Scachard analysis of the specific binding curves.
Figure 13:
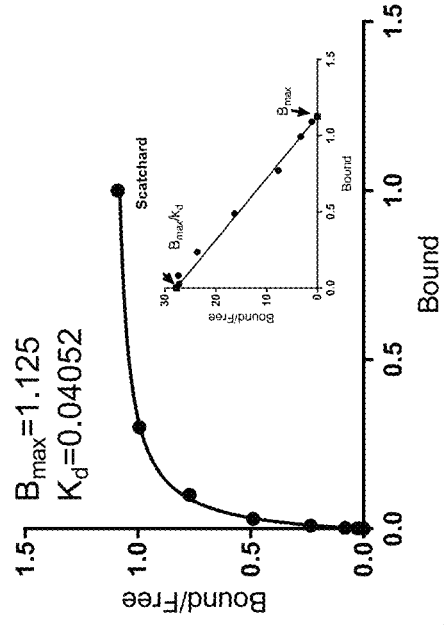
Figure 13:
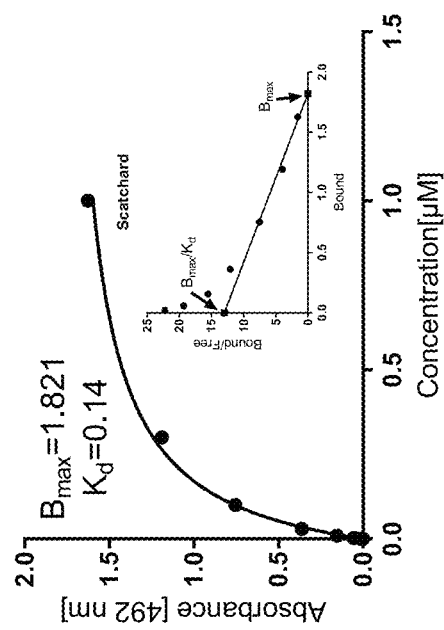
Figure 13:
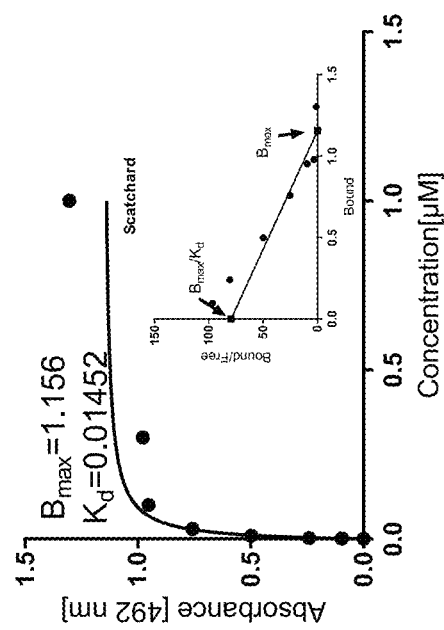
Figure 15:
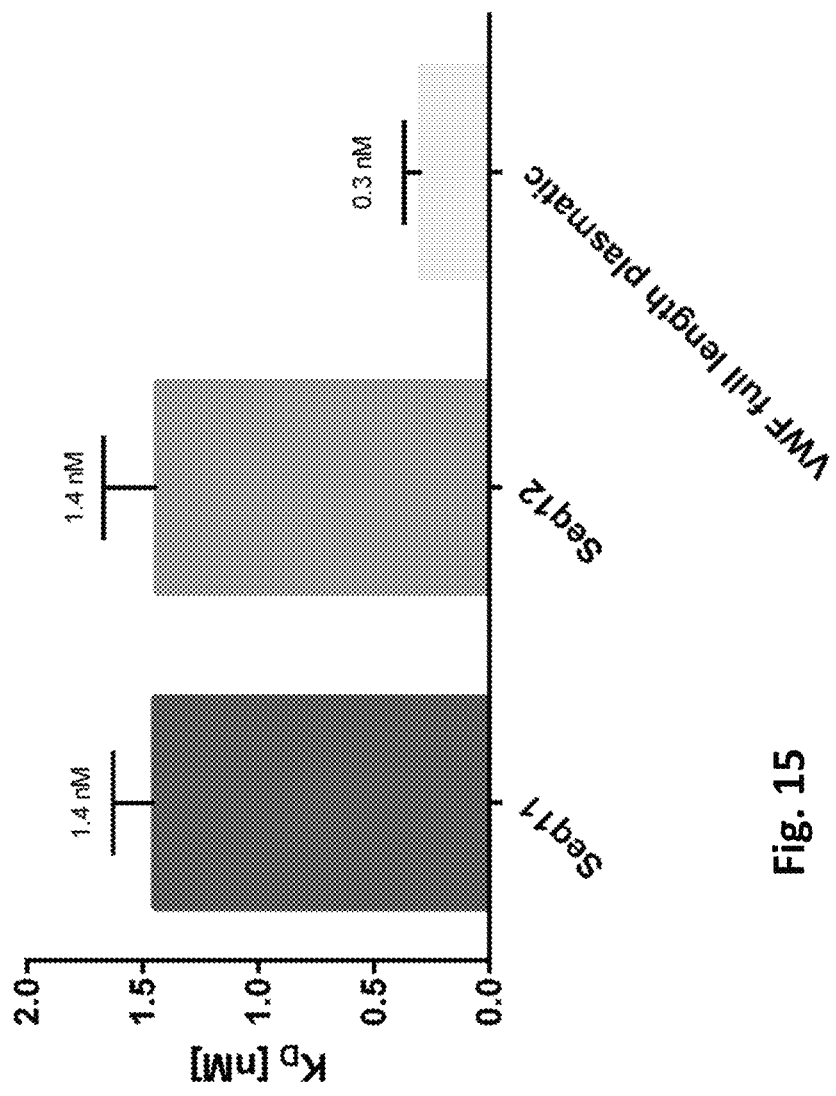
FIG. 15 shows the dissociation affinity constants (KD) values calculated for the binding of Seq11, Seq12 and full length plasmatic VWF to recombinant FVIII. Data was obtained by SPR.

The biding curves of the Sequences 11 and 12 and the corresponding Scachard plots are depicted in FIGS. 12 and 13. The apparent binding affinities ($K_D$) derived from the Schachard plots are summarized in FIG. 14. The increase in O-glycan repeats in Seq12 had a significant effect on SIGLEC binding affinity. The affinity for SIGLEC 5 could be increased from 0.494 µM for Seq11 to 0.14 µM for Seq12. The affinity for SIGLEC 7 could be increased from 0.371 µM for Seq11 to 0.005 µM for Seq12. The affinity for SIGLEC 8 could be increased from 1.027 µM for Seq11 to 0.015 µM for Seq12. Finally, the affinity for SIGLEC 9 could be increased from 0.591 µM for Seq11 to 0.041 µM for Seq12. Statement in the text: "from this ELISA experiment dissociation affinity constants will be calculated for all Seq11 and 12-SIGLEC interactions".

Example 11—Determination of the FVIII Binding Affinity Seq11 and Seq12

11.1 Experimental Procedure

FVIII binding of both sequences was evaluated by surface plasmon resonance (SPR). The analysis was carried out using Biacore 3000 (GE Healthcare) instrument. The Sequence 11 and 12 polypeptides were immobilized on a CM5 chip using amine coupling kit (GE Healthcare). As a positive control full length plasmatic VWF (Wilate, Octapharma) was immobilized. Subsequently, FVIII (Nuwiq, Octapharma) concentration series (0.2 nM, 0.6 nM, 1.7 nM, 5.0 nM, 15 nM, 45 nM) was injected over the sensor chip surface. The running buffer was 150 mM HEPES, 150 mM NaCl, 5 mM $CaCl_2$), 0.05%.

11.2 Results

SPR measurement revealed, that FVIII binding affinity (KD) of both sequences equals 1.4 nM, the additional O-glycan repeats have therefore no impact on the binding affinity to FVIII.

Example 12—the N-Terminal, but not the C-Terminal VWF Fragment Reduce the Extracellular Level of IL-12p70 and IFN-γ

12.1 Background

SIGLECs are expressed on various cells of the immune system, including monocytes and dendritic cells, and exhibit a role in cell adhesion, endocytosis and modulating signaling pathways of the adaptive and innate immunity (Macauley et al. 2014). Most SIGLECs contain an immunoreceptor tyrosine-based inhibitory motif (ITIM) or ITIM-like motif in their cytoplasmic domain which has been shown to function in attenuation of inflammatory response by inhibiting cellular proliferation and activation (Vitale et al. 1999; Ikehara et al. 2004), inducing apoptosis (Nutku et al. 2003) and suppressing cytokine production (Erdmann et al. 2009; Chen et al. 2013).

In order to see if the levels of inflammatory cytokines produced by moDC are altered in the presence of SIGLEC-engaging vWF-fragment, amounts of IL-12p70 and IFN-γ in the supernatant of stimulated immature monocyte derived dendritic cells (moDC) were analyzed simultaneously by flow cytometry.

12.2 Experimental Design

Monocytes from healthy donors were enriched via Ficoll gradient and subsequently CD14+ monocytes were purified by magnetic cell sorting. To obtain moDC, CD14+ monocytes were cultivated for 5 to 6 days in RPMI medium supplemented with 10% fetal calf serum, 1000 U/ml interleukin 4 and 1000 U/ml granulocyte-macrophage colony-stimulating factor. The cytokine profile secreted by the moDC was analyzed 24 h post stimulation with the respective vWF fragments via the cytometric bead array CBA Flex (BD) detecting IL-12p70 and IFN-γ according to the manufacturer's recommendation. Cells treated with the same volume of 100 mM NaCl served as control. Samples were analyzed with the flow cytometer FACSVerse. Final analysis and calculation of the cytokine concentration was carried out using FCAP Array software (BD).

12.3 Results

FIG. 16 shows the cytokine concentration after incubation of the moDCs with the two vWF fragments with and without LPS stimulation. According to these results, the N-terminal but not the C-terminal part of vWF lowers the production of pro-inflammatory cytokines synthesized in response to LPS stimulation. Without LPS stimulation, no effect of the vWF fragments on secretion of the pro-inflammatory cytokines could be detected.

Example 13—Analysis of Phosphorylation of SIGLECs and their Adaptor Molecules 13.1 Background Upon sialic acid-containing ligand binding, the ITIM and ITIM-like motifs of SIGLECs become phosphorylated by SRC-family tyrosine kinases which leads to the recruitment of SRC homology 2 (SH2)-domain containing protein tyrosine phosphatase (SHP)-1 and SHP-2. Once activated, these phosphatases can dephosphorylate cellular substrates, thereby controlling the activation of various signaling pathways (Crocker et al., 2007). While SHP-1 has been ascribed a role in inhibitory signaling, SHP-2 enhances signal transduction in most signaling pathways, but has also been reported to be involved in negatively regulating intracellular signaling processes (An et al., 2006; Avril et al., 2004; Boyd et al., 2009; Qu, 2000; Salmond and Alexander, 2006).

13.2 Experimental Procedure

MoDCs were prepared as described in example 12. In order to determine the influence of the N-terminal vWF-fragment on tyrosine phosphorylation of SIGLECs and their adaptor molecules SHP-1 and SHP-2, $6*10^6$ moDC were incubated for 10 minutes with 500 nM of the N-terminal vWF fragment. Cells stimulated with the same volume of 100 mM NaCl served as a control. Analysis of immunoreceptor-phosphorylation was carried out with the Proteome Profiler Human Phospho-Immunoreceptor Array Kit (R&D systems) according to the manufacturer's recommendations using 500 µg cell lysate.

13.3 Results

The results of the Phospho-Immunoreceptor Array are shown in FIG. 17. According to the measured pixel density, the N-terminal vWF fragment specifically alters the phosphorylation of SHP-1, SHP-2, SIG-5 and SIG-7 as compared to control. The phosphorylation of SIG-2 and SIG-10 could not be observed, which is in close accordance with the lack of binding of vWF N-terminal fragment to these SIGLECs.

Many modifications and other embodiments of the invention set forth herein will come to mind to the one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

REFERENCES

An, H., Zhao, W., Hou, J., Zhang, Y., Xie, Y., Zheng, Y., Xu, H., Qian, C., Zhou, J., Yu, Y., Liu, S., Feng, G., and Cao, X. (2006). SHP-2 phosphatase negatively regulates the TRIF adaptor protein-dependent type I interferon and proinflammatory cytokine production. Immunity. 25, 919-928.

Avril, T., Floyd, H., Lopez, F., Vivier, E., and Crocker, P. R. (2004). The membrane-proximal immunoreceptor tyrosine-based inhibitory motif is critical for the inhibitory signaling mediated by Siglecs-7 and -9, CD33-related Siglecs expressed on human monocytes and NK cells. J. Immunol. 173, 6841-6849.

Boyd, C. R., Orr, S. J., Spence, S., Burrows, J. F., Elliott, J., Carroll, H. P., Brennan, K., Ni, G. J., Coulter, W. A., Jones, C., Crocker, P. R., Johnston, J. A., and Jefferies, C. A. (2009). Siglec-E is up-regulated and phosphorylated following lipopolysaccharide stimulation in order to limit TLR-driven cytokine production. J. Immunol. 183, 7703-7709.

Chen, Weilin; Han, Chaofeng; Xie, Bin; Hu, Xiang; Yu, Qian; Shi, Liyun et al. (2013): Induction of Siglec-G by RNA viruses inhibits the innate immune response by promoting RIG-I degradation. In: Cell 152 (3), S. 467-478. DOI: 10.1016/j.cell.2013.01.011.

Crocker, P. R., Paulson, J. C., and Varki, A. (2007). Siglecs and their roles in the immune system. Nat. Rev. Immunol. 7, 255-266.

Ewenstein B M, Collins P, Tarantino M D, Negrier C, Blanchette V, Shapiro A D, Baker D, Spotts G, Sensel M, Yi S E, Gomperts E D. Hemophilia therapy innovation development of an advanced category recombinant factor VIII by a plasma/albumin-free method Proceedings of a Special Symposium at the XIXth Congress of the International Society on Thrombosis and Haemostasis; 2004, vol. 41, pg. 1-16.

Erdmann, Hanna; Steeg, Christiane; Koch-Nolte, Friedrich; Fleischer, Bernhard; Jacobs, Thomas (2009): Sialylated ligands on pathogenic *Trypanosoma cruzi* interact with Siglec-E (sialic acid-binding Ig-like lectin-E). In: Cellular microbiology 11 (11), S. 1600-1611. DOI: 10.1111/j.1462-5822.2009.01350.x.

Franc V, Rehulka P, Raus M, Stulik J, Novak J, Renfrow M B, Sebela M. Elucidating heterogeneity of IgA1 hinge-region O-glycosylation by use of MALDI-TOF/TOF mass spectrometry: role of cysteine alkylation during sample processing. Journal of Proteomics, 2013, Oct. 30; vol. 92, pg. 299-312

Guzman-Aranguez A, Argueso P. Structure and Biological Roles of Mucin-type O-glycans at the Ocular Surface. The ocular surface. 2010; vol. 8 (1) pg. 8-17.

Ikehara, Yuzuru; Ikehara, Sanae Kabata; Paulson, James C. (2004): Negative regulation of T cell receptor signaling by Siglec-7 (p70/AIRM) and Siglec-9. In: The Journal of biological chemistry 279 (41), S. 43117-43125. DOI: 10.1074/jbc.M403538200.

Lai J D Georgescu M T, Hough C, Lillicrap D. To clear or to fear: An innate perspective on factor VIII immunity, Cellular Immunology, 2016 March; vol. 301, pg. 82-89.

Nutku, Esra; Aizawa, Hideyuki; Hudson, Sherry A.; Bochner, Bruce S. (2003): Ligation of Siglec-8: a selective mechanism for induction of human eosinophil apoptosis. In: Blood 101 (12), S. 5014-5020. DOI: 10.1182/blood-2002-10-3058.

Pegon J N, Kurdi M, Casari C, Odouard S, Denis C V, Christophe O D, Lenting P J. Factor VIII and von Willebrand factor are ligands for the carbohydrate-receptor Siglec-5, Haematologica. 2012 December; 97(12):1855-63.

Paulson J C, Macauley M S, and Kawasaki N. Siglecs as sensors of self in innate and adaptive immune responses. Ann N Y Acad Sci. 2012 April; 1253(1): 37-48.

Qu, C. K. (2000). The SHP-2 tyrosine phosphatase: signaling mechanisms and biological functions. Cell Res. 10, 279-288.

Salmond, R. J., and Alexander, D. R. (2006). SHP2 forecast for the immune system: fog gradually clearing. Trends Immunol. 27, 154-160.

Solecka B A, Weise C, Laffan M A, Kannicht C, Site-specific analysis of von Willebrand factor O-glycosylation, J Thromb Haemost. 2016 Jan. 19.

Vitale, C.; Romagnani, C.; Falco, M.; Ponte, M.; Vitale, M.; Moretta, A. et al. (1999): Engagement of p75/AIRM1 or CD33 inhibits the proliferation of normal or leukemic myeloid cells. In: Proceedings of the National Academy of Sciences of the United States of America 96 (26), S. 15091-15096.

---

What is claimed is:

1. A recombinant glycosylated polypeptide comprising an amino acid sequence identical to a naturally-occurring human protein or fragment thereof, wherein said recombinant glycosylated polypeptide contains one or more clusters of O-glycosylation sites, wherein a cluster contains at least three O-glycosylation sites and at least one O-glycosylation site in four amino acids; wherein the total number of O-glycosylation sites and the combined number of sialylated core 2 and extended core 1 O-glycans of the recombinant glycosylated polypeptide is higher than the total number of O-glycosylation sites and the combined number of sialylated core 2 and extended core 1 O-glycans of the naturally-occurring human protein or fragment thereof; and wherein the recombinant glycosylated polypeptide shows an increased binding affinity to one or more SIGLECs selected from SIG-5, SIG-7, SIG-8, and SIG-9, compared to the naturally-occurring human protein or fragment thereof.

2. The recombinant glycosylated polypeptide according to claim 1, wherein the recombinant glycosylated polypeptide shows an increased binding to each of SIGLECs SIG-5, SIG-7, SIG-8, and SIG-9.

3. The recombinant glycosylated polypeptide according to claim 1, wherein the number of sialylated core 2 O-glycans of the recombinant glycosylated polypeptide is higher than the number of sialylated core 2 O-glycans of the naturally-occurring human protein or fragment thereof.

4. The recombinant glycosylated polypeptide according to claim 1, wherein the recombinant glycosylated polypeptide comprises at least two clusters of O-glycosylation sites.

5. The recombinant glycosylated polypeptide according to claim 1, wherein the clusters of O-glycosylation sites are separated by less than 100 amino acids.

6. The recombinant glycosylated polypeptide according to claim 1, wherein the sialylated O-glycans contain at least two sialic acids in α2-3 linked and/or α2-8 glycosidic linkage.

7. The recombinant glycosylated polypeptide according to claim 6, wherein the percentage of core 2 O-glycans based on the number of sialylated O-glycans is at least 5%.

8. The recombinant glycosylated polypeptide according to claim 1, further comprising a multimerization domain.

9. The recombinant glycosylated polypeptide according to claim 1, wherein the human protein is selected from the group consisting of FVIII, FVII, FIX, and ADAMTS13.

10. The recombinant glycosylated polypeptide according to claim 1, wherein the recombinant glycosylated polypeptide is a fusion protein, wherein a second amino acid sequence containing one or more O-glycosylation sites is covalently linked to the amino acid sequence identical to the naturally-occurring human protein or fragment thereof.

11. The recombinant glycosylated polypeptide according to claim 10, wherein the covalent linker is selected from a peptide bond, a chemical linker, or a glycosidic bond.

12. The recombinant glycosylated polypeptide according to claim 10, wherein the second amino acid sequence is at least 98% homologous to amino acids 475 to 505 of SEQ ID NO: 1 or to two consecutive copies of amino acids 475 to 505 of SEQ ID NO: 1.

13. The recombinant glycosylated polypeptide according to claim 1 produced by expression in a human cell line.

14. A composition comprising:

a first polypeptide, and a second polypeptide, wherein the first polypeptide comprises an amino acid sequence identical to a naturally-occurring human protein or fragment thereof, wherein said recombinant glycosylated polypeptide contains one or more clusters of O-glycosylation sites, wherein a cluster contains at least three O-glycosylation sites and at least one O-glycosylation site in four amino acids;

wherein the total number of O-glycosylation sites and the combined number of sialylated core 2 O-glycans of the recombinant glycosylated polypeptide is higher than the total number of O-glycosylation sites and the combined number of sialylated core 2 O-glycans of the naturally-occurring human protein or fragment thereof; wherein the recombinant glycosylated polypeptide shows an increased binding affinity to one or more SIGLECs, selected from SIG-5, SIG-7, SIG-8, and SIG-9, compared to the naturally-occurring human protein or fragment thereof, wherein the second polypeptide contains an amino acid sequence homologous or identical to a human protein, and wherein compared to the second polypeptide, the composition has an increased binding affinity to one or more of SIGLECs SIG-5, SIG-7, SIG-8, and SIG-9.

15. The composition according to claim 14, wherein the second polypeptide is a FVIII protein.

16. The recombinant glycosylated polypeptide according to claim 1, wherein the cluster contains at least four O-glycosylation sites.

17. The recombinant glycosylated polypeptide according to claim 1, wherein the one or more clusters contain at least one O-glycosylation site in three amino acids.

18. The recombinant glycosylated polypeptide according to claim 4, containing at least three clusters of O-glycosylation sites.

19. The recombinant glycosylated polypeptide according to claim 5, wherein the clusters of O-glycosylation sites are separated by less than 50 amino acids.

20. The recombinant glycosylated polypeptide according to claim 5, wherein the clusters of O-glycosylation sites are separated by less than 30 amino acids.

21. The recombinant glycosylated polypeptide according to claim 6, wherein the sialylated O-glycans contain at least three sialic acids in α2-3 linked and/or α2-8 glycosidic linkage.

22. The recombinant glycosylated polypeptide according to claim 7, wherein the percentage of core 2 O-glycans based on the number of sialylated O-glycans is at least 10%.

23. The recombinant glycosylated polypeptide according to claim 7, wherein the percentage of core 2 O-glycans based on the number of sialylated O-glycans is at least 50%.

24. The recombinant glycosylated polypeptide according to claim 12, wherein the second amino acid sequence is identical to amino acids 475 to 505 of SEQ ID NO: 1 or to two consecutive copies of amino acids 475 to 505 of SEQ ID NO: 1.

25. The composition according to claim 15, wherein the FVIII protein is a full length FVIII protein, a B-domain deleted FVIII protein, or a FVIII protein in which a part of the B-domain has been replaced by a linker.

* * * * *

SEQUENCE LISTING

```
<160> NUMBER OF SEQ ID NOS: 21

<210> SEQ ID NO 1
<211> LENGTH: 2050
<212> TYPE: PRT
<213> ORGANISM: Homo sapiens

<400> SEQUENCE: 1

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
```

```
                85                  90                  95
Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
                115                 120                 125

Val Leu Val Gln Asp Tyr Cys Gly Ser Asn Pro Gly Thr Phe Arg Ile
                130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Gly Lys Ala Leu Ser
                195                 200                 205

Val Val Trp Asp Arg His Leu Ser Ile Ser Val Val Leu Lys Gln Thr
                210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
                275                 280                 285

Lys Gln Thr Met Val Asp Ser Ser Cys Arg Ile Leu Thr Ser Asp Val
                290                 295                 300

Phe Gln Asp Cys Asn Lys Leu Val Asp Pro Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
                450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
                500                 505                 510
```

```
Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
        530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
        610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
                660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
        690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
                725                 730                 735

Ala Phe Val Leu Glu Gly Ser Asp Lys Ile Gly Glu Ala Asp Phe Asn
                740                 745                 750

Arg Ser Lys Glu Phe Met Glu Glu Val Ile Gln Arg Met Asp Val Gly
        755                 760                 765

Gln Asp Ser Ile His Val Thr Val Leu Gln Tyr Ser Tyr Met Val Thr
        770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
                820                 825                 830

Asp Arg Glu Gln Ala Pro Asn Leu Val Tyr Met Val Thr Gly Asn Pro
        835                 840                 845

Ala Ser Asp Glu Ile Lys Arg Leu Pro Gly Asp Ile Gln Val Val Pro
        850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
                900                 905                 910

Gln Ile Pro Thr Leu Ser Pro Ala Pro Asp Cys Ser Gln Pro Leu Asp
        915                 920                 925
```

-continued

Val Ile Leu Leu Asp Gly Ser Ser Phe Pro Ala Ser Tyr Phe
930             935             940

Asp Glu Met Lys Ser Phe Ala Lys Ala Phe Ile Ser Lys Ala Asn Ile
945             950             955             960

Gly Pro Arg Leu Thr Gln Val Ser Val Leu Gln Tyr Gly Ser Ile Thr
                965             970             975

Thr Ile Asp Val Pro Trp Asn Val Val Pro Glu Lys Ala His Leu Leu
            980             985             990

Ser Leu Val Asp Val Met Gln Arg Glu Gly Gly Pro Ser Gln Ile Gly
        995             1000            1005

Asp Ala Leu Gly Phe Ala Val Arg Tyr Leu Thr Ser Glu Met His
    1010            1015            1020

Gly Ala Arg Pro Gly Ala Ser Lys Ala Val Val Ile Leu Val Thr
    1025            1030            1035

Asp Val Ser Val Asp Ser Val Asp Ala Ala Asp Ala Ala Arg
    1040            1045            1050

Ser Asn Arg Val Thr Val Phe Pro Ile Gly Ile Gly Asp Arg Tyr
    1055            1060            1065

Asp Ala Ala Gln Leu Arg Ile Leu Ala Gly Pro Ala Gly Asp Ser
    1070            1075            1080

Asn Val Val Lys Leu Gln Arg Ile Glu Asp Leu Pro Thr Met Val
    1085            1090            1095

Thr Leu Gly Asn Ser Phe Leu His Lys Leu Cys Ser Gly Phe Val
    1100            1105            1110

Arg Ile Cys Met Asp Glu Asp Gly Asn Glu Lys Arg Pro Gly Asp
    1115            1120            1125

Val Trp Thr Leu Pro Asp Gln Cys His Thr Val Thr Cys Gln Pro
    1130            1135            1140

Asp Gly Gln Thr Leu Leu Lys Ser His Arg Val Asn Cys Asp Arg
    1145            1150            1155

Gly Leu Arg Pro Ser Cys Pro Asn Ser Gln Ser Pro Val Lys Val
    1160            1165            1170

Glu Glu Thr Cys Gly Cys Arg Trp Thr Cys Pro Cys Val Cys Thr
    1175            1180            1185

Gly Ser Ser Thr Arg His Ile Val Thr Phe Asp Gly Gln Asn Phe
    1190            1195            1200

Lys Leu Thr Gly Ser Cys Ser Tyr Val Leu Phe Gln Asn Lys Glu
    1205            1210            1215

Gln Asp Leu Glu Val Ile Leu His Asn Gly Ala Cys Ser Pro Gly
    1220            1225            1230

Ala Arg Gln Gly Cys Met Lys Ser Ile Glu Val Lys His Ser Ala
    1235            1240            1245

Leu Ser Val Glu Leu His Ser Asp Met Glu Val Thr Val Asn Gly
    1250            1255            1260

Arg Leu Val Ser Val Pro Tyr Val Gly Gly Asn Met Glu Val Asn
    1265            1270            1275

Val Tyr Gly Ala Ile Met His Glu Val Arg Phe Asn His Leu Gly
    1280            1285            1290

His Ile Phe Thr Phe Thr Pro Gln Asn Asn Glu Phe Gln Leu Gln
    1295            1300            1305

Leu Ser Pro Lys Thr Phe Ala Ser Lys Thr Tyr Gly Leu Cys Gly
    1310            1315            1320

Ile Cys Asp Glu Asn Gly Ala Asn Asp Phe Met Leu Arg Asp Gly

-continued

```
            1325                1330                1335
Thr Val Thr Thr Asp Trp Lys Thr Leu Val Gln Glu Trp Thr Val
        1340                1345                1350
Gln Arg Pro Gly Gln Thr Cys Gln Pro Ile Leu Glu Glu Gln Cys
        1355                1360                1365
Leu Val Pro Asp Ser Ser His Cys Gln Val Leu Leu Leu Pro Leu
        1370                1375                1380
Phe Ala Glu Cys His Lys Val Leu Ala Pro Ala Thr Phe Tyr Ala
        1385                1390                1395
Ile Cys Gln Gln Asp Ser Cys His Gln Glu Gln Val Cys Glu Val
        1400                1405                1410
Ile Ala Ser Tyr Ala His Leu Cys Arg Thr Asn Gly Val Cys Val
        1415                1420                1425
Asp Trp Arg Thr Pro Asp Phe Cys Ala Met Ser Cys Pro Pro Ser
        1430                1435                1440
Leu Val Tyr Asn His Cys Glu His Gly Cys Pro Arg His Cys Asp
        1445                1450                1455
Gly Asn Val Ser Ser Cys Gly Asp His Pro Ser Glu Gly Cys Phe
        1460                1465                1470
Cys Pro Pro Asp Lys Val Met Leu Glu Gly Ser Cys Val Pro Glu
        1475                1480                1485
Glu Ala Cys Thr Gln Cys Ile Gly Glu Asp Gly Val Gln His Gln
        1490                1495                1500
Phe Leu Glu Ala Trp Val Pro Asp His Gln Pro Cys Gln Ile Cys
        1505                1510                1515
Thr Cys Leu Ser Gly Arg Lys Val Asn Cys Thr Thr Gln Pro Cys
        1520                1525                1530
Pro Thr Ala Lys Ala Pro Thr Cys Gly Leu Cys Glu Val Ala Arg
        1535                1540                1545
Leu Arg Gln Asn Ala Asp Gln Cys Cys Pro Glu Tyr Glu Cys Val
        1550                1555                1560
Cys Asp Pro Val Ser Cys Asp Leu Pro Pro Val Pro His Cys Glu
        1565                1570                1575
Arg Gly Leu Gln Pro Thr Leu Thr Asn Pro Gly Glu Cys Arg Pro
        1580                1585                1590
Asn Phe Thr Cys Ala Cys Arg Lys Glu Glu Cys Lys Arg Val Ser
        1595                1600                1605
Pro Pro Ser Cys Pro Pro His Arg Leu Pro Thr Leu Arg Lys Thr
        1610                1615                1620
Gln Cys Cys Asp Glu Tyr Glu Cys Ala Cys Asn Cys Val Asn Ser
        1625                1630                1635
Thr Val Ser Cys Pro Leu Gly Tyr Leu Ala Ser Thr Ala Thr Asn
        1640                1645                1650
Asp Cys Gly Cys Thr Thr Thr Thr Cys Leu Pro Asp Lys Val Cys
        1655                1660                1665
Val His Arg Ser Thr Ile Tyr Pro Val Gly Gln Phe Trp Glu Glu
        1670                1675                1680
Gly Cys Asp Val Cys Thr Cys Thr Asp Met Glu Asp Ala Val Met
        1685                1690                1695
Gly Leu Arg Val Ala Gln Cys Ser Gln Lys Pro Cys Glu Asp Ser
        1700                1705                1710
Cys Arg Ser Gly Phe Thr Tyr Val Leu His Glu Gly Glu Cys Cys
        1715                1720                1725
```

Gly Arg Cys Leu Pro Ser Ala Cys Glu Val Val Thr Gly Ser Pro
    1730            1735                1740

Arg Gly Asp Ser Gln Ser Ser Trp Lys Ser Val Gly Ser Gln Trp
    1745            1750                1755

Ala Ser Pro Glu Asn Pro Cys Leu Ile Asn Glu Cys Val Arg Val
    1760            1765                1770

Lys Glu Glu Val Phe Ile Gln Gln Arg Asn Val Ser Cys Pro Gln
    1775            1780                1785

Leu Glu Val Pro Val Cys Pro Ser Gly Phe Gln Leu Ser Cys Lys
    1790            1795                1800

Thr Ser Ala Cys Cys Pro Ser Cys Arg Cys Glu Arg Met Glu Ala
    1805            1810                1815

Cys Met Leu Asn Gly Thr Val Ile Gly Pro Gly Lys Thr Val Met
    1820            1825                1830

Ile Asp Val Cys Thr Thr Cys Arg Cys Met Val Gln Val Gly Val
    1835            1840                1845

Ile Ser Gly Phe Lys Leu Glu Cys Arg Lys Thr Thr Cys Asn Pro
    1850            1855                1860

Cys Pro Leu Gly Tyr Lys Glu Asn Asn Thr Gly Glu Cys Cys
    1865            1870                1875

Gly Arg Cys Leu Pro Thr Ala Cys Thr Ile Gln Leu Arg Gly Gly
    1880            1885                1890

Gln Ile Met Thr Leu Lys Arg Asp Glu Thr Leu Gln Asp Gly Cys
    1895            1900                1905

Asp Thr His Phe Cys Lys Val Asn Glu Arg Gly Glu Tyr Phe Trp
    1910            1915                1920

Glu Lys Arg Val Thr Gly Cys Pro Pro Phe Asp Glu His Lys Cys
    1925            1930                1935

Leu Ala Glu Gly Gly Lys Ile Met Lys Ile Pro Gly Thr Cys Cys
    1940            1945                1950

Asp Thr Cys Glu Glu Pro Glu Cys Asn Asp Ile Thr Ala Arg Leu
    1955            1960                1965

Gln Tyr Val Lys Val Gly Ser Cys Lys Ser Glu Val Glu Val Asp
    1970            1975                1980

Ile His Tyr Cys Gln Gly Lys Cys Ala Ser Lys Ala Met Tyr Ser
    1985            1990                1995

Ile Asp Ile Asn Asp Val Gln Asp Gln Cys Ser Cys Cys Ser Pro
    2000            2005                2010

Thr Arg Thr Glu Pro Met Gln Val Ala Leu His Cys Thr Asn Gly
    2015            2020                2025

Ser Val Val Tyr His Glu Val Leu Asn Ala Met Glu Cys Lys Cys
    2030            2035                2040

Ser Pro Arg Lys Cys Ser Lys
    2045            2050

<210> SEQ ID NO 2
<211> LENGTH: 567
<212> TYPE: PRT
<213> ORGANISM: Homo sapiens

<400> SEQUENCE: 2

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr

```
            20                  25                  30
Asp Leu Glu Cys Met Ser Met Gly Cys Val Ser Gly Cys Leu Cys Pro
             35                  40                  45
Pro Gly Met Val Arg His Glu Asn Arg Cys Val Ala Leu Glu Arg Cys
 50                  55                  60
Pro Cys Phe His Gln Gly Lys Glu Tyr Ala Pro Gly Glu Thr Val Lys
 65                  70                  75                  80
Ile Gly Cys Asn Thr Cys Val Cys Gln Asp Arg Lys Trp Asn Cys Thr
                 85                  90                  95
Asp His Val Cys Asp Ala Thr Cys Ser Thr Ile Gly Met Ala His Tyr
                100                 105                 110
Leu Thr Phe Asp Gly Leu Lys Tyr Leu Phe Pro Gly Glu Cys Gln Tyr
                115                 120                 125
Val Leu Val Gln Asp Tyr Cys Gly Ser Asn Pro Gly Thr Phe Arg Ile
            130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                165                 170                 175
Glu Val Asn Val Lys Arg Pro Met Lys Asp Glu Thr His Phe Glu Val
            180                 185                 190
Val Glu Ser Gly Arg Tyr Ile Ile Leu Leu Leu Gly Lys Ala Leu Ser
            195                 200                 205
Val Val Trp Asp Arg His Leu Ser Ile Ser Val Val Leu Lys Gln Thr
        210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
            260                 265                 270
Lys Val Pro Leu Asp Ser Ser Pro Ala Thr Cys His Asn Asn Ile Met
        275                 280                 285
Lys Gln Thr Met Val Asp Ser Ser Cys Arg Ile Leu Thr Ser Asp Val
        290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
            340                 345                 350
Lys Val Val Thr Trp Arg Thr Ala Thr Leu Cys Pro Gln Ser Cys Glu
            355                 360                 365
Glu Arg Asn Leu Arg Glu Asn Gly Tyr Glu Cys Glu Trp Arg Tyr Asn
        370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
            435                 440                 445
```

```
Val Thr Leu Asn Pro Ser Asp Pro Glu His Cys Gln Ile Cys His Cys
        450                 455                 460

Asp Val Val Asn Leu Thr Cys Glu Ala Cys Gln Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Gln Glu Pro Gly Gly Leu Val
            500                 505                 510

Val Pro Pro Thr Asp Ala Pro Val Ser Pro Thr Thr Leu Tyr Val Glu
            515                 520                 525

Asp Ile Ser Glu Pro Pro Leu His Gln Glu Pro Gly Gly Leu Val Val
            530                 535                 540

Pro Pro Thr Asp Ala Pro Val Ser Pro Thr Thr Leu Tyr Val Glu Asp
545                 550                 555                 560

Ile Ser Glu Pro Pro Leu His
                565

<210> SEQ ID NO 3
<211> LENGTH: 589
<212> TYPE: PRT
<213> ORGANISM: Homo sapiens

<400> SEQUENCE: 3

Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
            35                  40                  45

Lys Thr Cys Gln Asn Tyr Asp Leu Glu Cys Met Ser Met Gly Cys Val
        50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Gln Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
```

```
                245                 250                 255
Asn Phe Asp Gly Ile Gln Asn Asn Asp Leu Thr Ser Ser Asn Leu Gln
            260                 265                 270
Val Glu Glu Asp Pro Val Asp Phe Gly Asn Ser Trp Lys Val Ser Ser
        275                 280                 285
Gln Cys Ala Asp Thr Arg Lys Val Pro Leu Asp Ser Ser Pro Ala Thr
    290                 295                 300
Cys His Asn Asn Ile Met Lys Gln Thr Met Val Asp Ser Ser Cys Arg
305                 310                 315                 320
Ile Leu Thr Ser Asp Val Phe Gln Asp Cys Asn Lys Leu Val Asp Pro
                325                 330                 335
Glu Pro Tyr Leu Asp Val Cys Ile Tyr Asp Thr Cys Ser Cys Glu Ser
            340                 345                 350
Ile Gly Asp Cys Ala Cys Phe Cys Asp Thr Ile Ala Ala Tyr Ala His
        355                 360                 365
Val Cys Ala Gln His Gly Lys Val Val Thr Trp Arg Thr Ala Thr Leu
    370                 375                 380
Cys Pro Gln Ser Cys Glu Glu Arg Asn Leu Arg Glu Asn Gly Tyr Glu
385                 390                 395                 400
Cys Glu Trp Arg Tyr Asn Ser Cys Ala Pro Ala Cys Gln Val Thr Cys
                405                 410                 415
Gln His Pro Glu Pro Leu Ala Cys Pro Val Gln Cys Val Glu Gly Cys
            420                 425                 430
His Ala His Cys Pro Pro Gly Lys Ile Leu Asp Glu Leu Leu Gln Thr
        435                 440                 445
Cys Val Asp Pro Glu Asp Cys Pro Val Cys Glu Val Ala Gly Arg Arg
    450                 455                 460
Phe Ala Ser Gly Lys Lys Val Thr Leu Asn Pro Ser Asp Pro Glu His
465                 470                 475                 480
Cys Gln Ile Cys His Cys Asp Val Val Asn Leu Thr Cys Glu Ala Cys
                485                 490                 495
Gln Glu Pro Gly Gly Leu Val Val Pro Pro Thr Asp Ala Pro Val Ser
            500                 505                 510
Pro Thr Thr Leu Tyr Val Glu Asp Ile Ser Glu Pro Pro Leu His Gln
        515                 520                 525
Glu Pro Gly Gly Leu Val Val Pro Pro Thr Asp Ala Pro Val Ser Pro
    530                 535                 540
Thr Thr Leu Tyr Val Glu Asp Ile Ser Glu Pro Pro Leu His Gln Glu
545                 550                 555                 560
Pro Gly Gly Leu Val Val Pro Pro Thr Asp Ala Pro Val Ser Pro Thr
                565                 570                 575
Thr Leu Tyr Val Glu Asp Ile Ser Glu Pro Pro Leu His
            580                 585

<210> SEQ ID NO 4
<211> LENGTH: 1330
<212> TYPE: PRT
<213> ORGANISM: Homo sapiens

<400> SEQUENCE: 4

Met Ile Pro Ala Arg Phe Ala Gly Val Leu Leu Ala Leu Ala Leu Ile
1               5                   10                  15
Leu Pro Gly Thr Leu Cys Ala Glu Gly Thr Arg Gly Arg Ser Ser Thr
            20                  25                  30
```

-continued

Ala Arg Cys Ser Leu Phe Gly Ser Asp Phe Val Asn Thr Phe Asp Gly
         35                  40                  45

Ser Met Tyr Ser Phe Ala Gly Tyr Cys Ser Tyr Leu Leu Ala Gly Gly
     50                  55                  60

Cys Gln Lys Arg Ser Phe Ser Ile Ile Gly Asp Phe Gln Asn Gly Lys
 65              70                  75                  80

Arg Val Ser Leu Ser Val Tyr Leu Gly Glu Phe Phe Asp Ile His Leu
                 85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
    195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
    355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
    435                 440                 445

Pro Gly Leu His Asn Ser Leu Val Lys Leu Lys His Gly Ala Gly Val

```
              450                 455                 460
Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
                515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
                675                 680                 685

Cys Pro Pro Gly Leu Tyr Met Asp Glu Arg Gly Asp Cys Val Pro Lys
                690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
                770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Gln Asp Arg Lys Trp Asn Cys Thr Asp His Val Cys Asp
                850                 855                 860

Ala Thr Cys Ser Thr Ile Gly Met Ala His Tyr Leu Thr Phe Asp Gly
865                 870                 875                 880
```

-continued

```
Leu Lys Tyr Leu Phe Pro Gly Glu Cys Gln Tyr Val Leu Val Gln Asp
            885             890             895

Tyr Cys Gly Ser Asn Pro Gly Thr Phe Arg Ile Leu Val Gly Asn Lys
            900             905             910

Gly Cys Ser His Pro Ser Val Lys Cys Lys Arg Val Thr Ile Leu
            915             920             925

Val Glu Gly Gly Glu Ile Glu Leu Phe Asp Gly Glu Val Asn Val Lys
            930             935             940

Arg Pro Met Lys Asp Glu Thr His Phe Glu Val Val Glu Ser Gly Arg
945             950             955             960

Tyr Ile Ile Leu Leu Leu Gly Lys Ala Leu Ser Val Val Trp Asp Arg
            965             970             975

His Leu Ser Ile Ser Val Val Leu Lys Gln Thr Tyr Gln Glu Lys Val
            980             985             990

Cys Gly Leu Cys Gly Asn Phe Asp  Gly Ile Gln Asn Asn  Asp Leu Thr
            995            1000             1005

Ser Ser  Asn Leu Gln Val Glu  Glu Asp Pro Val Asp  Phe Gly Asn
    1010            1015            1020

Ser Trp  Lys Val Ser Ser Gln  Cys Ala Asp Thr Arg  Lys Val Pro
    1025            1030            1035

Leu Asp  Ser Ser Pro Ala Thr  Cys His Asn Asn Ile  Met Lys Gln
    1040            1045            1050

Thr Met  Val Asp Ser Ser Cys  Arg Ile Leu Thr Ser  Asp Val Phe
    1055            1060            1065

Gln Asp  Cys Asn Lys Leu Val  Asp Pro Glu Pro Tyr  Leu Asp Val
    1070            1075            1080

Cys Ile  Tyr Asp Thr Cys Ser  Cys Glu Ser Ile Gly  Asp Cys Ala
    1085            1090            1095

Cys Phe  Cys Asp Thr Ile Ala  Ala Tyr Ala His Val  Cys Ala Gln
    1100            1105            1110

His Gly  Lys Val Val Thr Trp  Arg Thr Ala Thr Leu  Cys Pro Gln
    1115            1120            1125

Ser Cys  Glu Glu Arg Asn Leu  Arg Glu Asn Gly Tyr  Glu Cys Glu
    1130            1135            1140

Trp Arg  Tyr Asn Ser Cys Ala  Pro Ala Cys Gln Val  Thr Cys Gln
    1145            1150            1155

His Pro  Glu Pro Leu Ala Cys  Pro Val Gln Cys Val  Glu Gly Cys
    1160            1165            1170

His Ala  His Cys Pro Pro Gly  Lys Ile Leu Asp Glu  Leu Leu Gln
    1175            1180            1185

Thr Cys  Val Asp Pro Glu Asp  Cys Pro Val Cys Glu  Val Ala Gly
    1190            1195            1200

Arg Arg  Phe Ala Ser Gly Lys  Lys Val Thr Leu Asn  Pro Ser Asp
    1205            1210            1215

Pro Glu  His Cys Gln Ile Cys  His Cys Asp Val Val  Asn Leu Thr
    1220            1225            1230

Cys Glu  Ala Cys Gln Glu Pro  Gly Gly Leu Val Val  Pro Pro Thr
    1235            1240            1245

Asp Ala  Pro Val Ser Pro Thr  Thr Leu Tyr Val Glu  Asp Ile Ser
    1250            1255            1260

Glu Pro  Pro Leu His Gln Glu  Pro Gly Gly Leu Val  Val Pro Pro
    1265            1270            1275
```

```
Thr Asp Ala Pro Val Ser Pro Thr Thr Leu Tyr Val Glu Asp Ile
    1280            1285                1290

Ser Glu Pro Pro Leu His Gln Glu Pro Gly Gly Leu Val Val Pro
    1295                1300                1305

Pro Thr Asp Ala Pro Val Ser Pro Thr Thr Leu Tyr Val Glu Asp
    1310                1315                1320

Ile Ser Glu Pro Pro Leu His
    1325            1330

<210> SEQ ID NO 5
<211> LENGTH: 1423
<212> TYPE: PRT
<213> ORGANISM: Homo sapiens

<400> SEQUENCE: 5

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65              70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145             150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225             230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305             310                 315                 320
```

```
Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
            370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
            450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
            690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735
```

-continued

```
His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
            770                 775             780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Gln Asp Arg Lys Trp Asn Cys Thr Asp His Val Cys Asp
            850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                  1000                1005

Ser Ser  Asn Leu Gln Val Glu  Glu Asp Pro Val Asp  Phe Gly Asn
            1010                1015                1020

Ser Trp  Lys Val Ser Ser Gln  Cys Ala Asp Thr Arg  Lys Val Pro
            1025                1030                1035

Leu Asp  Ser Ser Pro Ala Thr  Cys His Asn Asn Ile  Met Lys Gln
            1040                1045                1050

Thr Met  Val Asp Ser Ser Cys  Arg Ile Leu Thr Ser  Asp Val Phe
            1055                1060                1065

Gln Asp  Cys Asn Lys Leu Val  Asp Pro Glu Pro Tyr  Leu Asp Val
            1070                1075                1080

Cys Ile  Tyr Asp Thr Cys Ser  Cys Glu Ser Ile Gly  Asp Cys Ala
            1085                1090                1095

Cys Phe  Cys Asp Thr Ile Ala  Ala Tyr Ala His Val  Cys Ala Gln
            1100                1105                1110

His Gly  Lys Val Val Thr Trp  Arg Thr Ala Thr Leu  Cys Pro Gln
            1115                1120                1125

Ser Cys  Glu Glu Arg Asn Leu  Arg Glu Asn Gly Tyr  Glu Cys Glu
            1130                1135                1140

Trp Arg  Tyr Asn Ser Cys Ala  Pro Ala Cys Gln Val  Thr Cys Gln
```

-continued

```
                    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Gln Glu Pro Gly Gly Leu Val Val Pro Pro
    1265                1270                1275

Thr Asp Ala Pro Val Ser Pro Thr Thr Leu Tyr Val Glu Asp Ile
    1280                1285                1290

Ser Glu Pro Pro Leu His Gln Glu Pro Gly Gly Leu Val Val Pro
    1295                1300                1305

Pro Thr Asp Ala Pro Val Pro Thr Thr Leu Tyr Val Glu Asp Ile
    1310                1315                1320

Ser Glu Pro Pro Leu His Glu Pro Glu Cys Asn Asp Ile Thr
    1325                1330                1335

Ala Arg Leu Gln Tyr Val Lys Val Gly Ser Cys Lys Ser Glu Val
    1340                1345                1350

Glu Val Asp Ile His Tyr Cys Gln Gly Lys Cys Ala Ser Lys Ala
    1355                1360                1365

Met Tyr Ser Ile Asp Ile Asn Asp Val Gln Asp Gln Cys Ser Cys
    1370                1375                1380

Cys Ser Pro Thr Arg Thr Glu Pro Met Gln Val Ala Leu His Cys
    1385                1390                1395

Thr Asn Gly Ser Val Val Tyr His Glu Val Leu Asn Ala Met Glu
    1400                1405                1410

Cys Lys Cys Ser Pro Arg Lys Cys Ser Lys
    1415                1420

<210> SEQ ID NO 6
<211> LENGTH: 62
<212> TYPE: PRT
<213> ORGANISM: Homo sapiens

<400> SEQUENCE: 6

Lys Val Thr Leu Asn Pro Ser Asp Pro Glu His Cys Gln Ile Cys His
1               5                  10                  15

Cys Asp Val Val Asn Leu Thr Cys Glu Ala Cys Gln Glu Pro Gly Gly
            20                  25                  30

Leu Val Val Pro Pro Thr Asp Ala Pro Val Ser Pro Thr Thr Leu Tyr
        35                  40                  45

Val Glu Asp Ile Ser Glu Pro Pro Leu His Gly Ser Ala Trp
    50                  55                  60

<210> SEQ ID NO 7
<211> LENGTH: 124
```

```
<212> TYPE: PRT
<213> ORGANISM: Homo sapiens

<400> SEQUENCE: 7

Lys Val Thr Leu Asn Pro Ser Asp Pro Glu His Cys Gln Ile Cys His
1               5                   10                  15

Cys Asp Val Val Asn Leu Thr Cys Glu Ala Cys Gln Glu Pro Gly Gly
            20                  25                  30

Leu Val Val Pro Pro Thr Asp Ala Pro Val Ser Pro Thr Thr Leu Tyr
        35                  40                  45

Val Glu Asp Ile Ser Glu Pro Pro Leu His Gln Glu Pro Gly Gly Leu
    50                  55                  60

Val Val Pro Pro Thr Asp Ala Pro Val Ser Pro Thr Thr Leu Tyr Val
65                  70                  75                  80

Glu Asp Ile Ser Glu Pro Pro Leu His Gln Glu Pro Gly Gly Leu Val
                85                  90                  95

Val Pro Pro Thr Asp Ala Pro Val Ser Pro Thr Thr Leu Tyr Val Glu
            100                 105                 110

Asp Ile Ser Glu Pro Pro Leu His Gly Ser Ala Trp
        115                 120

<210> SEQ ID NO 8
<211> LENGTH: 23
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 8

Val Val Pro Pro Thr Xaa Ala Pro Val Xaa Pro Thr Thr Xaa Tyr Val
1               5                   10                  15

Xaa Xaa Xaa Ser Xaa Pro Pro
            20

<210> SEQ ID NO 9
<211> LENGTH: 23
<212> TYPE: PRT
<213> ORGANISM: Homo sapiens

<400> SEQUENCE: 9

Val Val Pro Pro Thr Asp Ala Pro Val Ser Pro Thr Thr Leu Tyr Val
1               5                   10                  15

Glu Asp Ile Ser Glu Pro Pro
            20

<210> SEQ ID NO 10
```

```
<211> LENGTH: 26
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid

<400> SEQUENCE: 10

Pro Pro Pro Thr Xaa Pro Pro Xaa Xaa Ala Xaa Val Thr Val Xaa Pro
1               5                   10                  15

Xaa Xaa Xaa Xaa Val Ser Thr Xaa Xaa Pro
            20                  25

<210> SEQ ID NO 11
<211> LENGTH: 26
<212> TYPE: PRT
<213> ORGANISM: Homo sapiens

<400> SEQUENCE: 11

Pro Pro Pro Thr Leu Pro Pro Asp Met Ala Gln Val Thr Val Gly Pro
1               5                   10                  15

Gly Leu Leu Gly Val Ser Thr Leu Gly Pro
            20                  25

<210> SEQ ID NO 12
<211> LENGTH: 47
<212> TYPE: PRT
<213> ORGANISM: Homo sapiens
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
```

```
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(37)
<223> OTHER INFORMATION: Xaa can be any naturally occurring amino acid
<220> FEATURE:
<221> NAME/KEY: misc_feature
<222> LOCATION: (39)..(41)
<223> OTHER INFORMATION: Xaa can be any naturally occurring amino acid
<220> FEATURE:
<221> NAME/KEY: misc_feature
<222> LOCATION: (44)..(47)
<223> OTHER INFORMATION: Xaa can be any naturally occurring amino acid

<400> SEQUENCE: 12

Val Ser Ser Thr Ser Xaa Xaa Xaa Xaa Ser Thr Xaa Pro Ser Xaa Xaa
1               5                   10                  15

Xaa Ala Ala Xaa Thr Xaa Xaa Thr Ser Ser Xaa Pro Pro Ser Xaa
            20                  25                  30

Pro Val Xaa Xaa Xaa Ser Xaa Xaa Thr Thr Xaa Xaa Xaa Xaa
            35                  40                  45

<210> SEQ ID NO 13
<211> LENGTH: 47
<212> TYPE: PRT
<213> ORGANISM: Homo sapiens

<400> SEQUENCE: 13

Val Ser Ser Thr Ser Asn Asn Leu Ile Ser Thr Ile Pro Ser Asp Asn
1               5                   10                  15

Leu Ala Ala Gly Thr Asp Asp Thr Ser Ser Leu Gly Pro Pro Ser Met
            20                  25                  30

Pro Val His Tyr Asp Ser Gln Leu Asp Thr Thr Leu Phe Gly Lys
            35                  40                  45

<210> SEQ ID NO 14
<211> LENGTH: 20
<212> TYPE: PRT
<213> ORGANISM: Homo sapiens
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 14

Xaa Xaa Xaa Ala Thr Thr Xaa Pro Xaa Xaa Xaa Xaa Xaa Xaa Thr Xaa
1               5                   10                  15

Pro Xaa Xaa Xaa
            20
```

<210> SEQ ID NO 15
<211> LENGTH: 20
<212> TYPE: PRT
<213> ORGANISM: Homo sapiens

<400> SEQUENCE: 15

Gln Phe Asn Ala Thr Thr Ile Pro Glu Asn Asp Ile Glu Lys Thr Asp
1               5                   10                  15

Pro Trp Phe Ala
            20

<210> SEQ ID NO 16
<211> LENGTH: 10
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 16

Xaa Xaa Thr Thr Ala Ala Thr Xaa Xaa Xaa
1               5                   10

<210> SEQ ID NO 17
<211> LENGTH: 10
<212> TYPE: PRT
<213> ORGANISM: Homo sapiens

<400> SEQUENCE: 17

Leu Gly Thr Thr Ala Ala Thr Glu Leu Lys
1               5                   10

<210> SEQ ID NO 18
<211> LENGTH: 17
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 18

Xaa Xaa Pro Thr Pro Xaa Xaa Xaa Ser Xaa Ser Xaa Xaa Xaa Glu Ala
1               5                   10                  15

Xaa

<210> SEQ ID NO 19

```
<211> LENGTH: 17
<212> TYPE: PRT
<213> ORGANISM: Homo sapiens

<400> SEQUENCE: 19

Gln Ser Pro Thr Pro His Gly Leu Ser Leu Ser Asp Leu Gln Glu Ala
1               5                   10                  15

Lys

<210> SEQ ID NO 20
<211> LENGTH: 37
<212> TYPE: PRT
<213> ORGANISM: Homo sapiens
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid

<400> SEQUENCE: 20

Val Xaa Xaa Xaa Xaa Xaa Xaa Xaa Xaa Xaa Thr Xaa Thr Ser Xaa Xaa
1               5                   10                  15

Ser Pro Xaa Xaa Xaa Xaa Xaa Val Xaa Xaa Ser Xaa Xaa Xaa Xaa Thr
                20                  25                  30

Xaa Xaa Ala Xaa Xaa
            35

<210> SEQ ID NO 21
<211> LENGTH: 37
<212> TYPE: PRT
<213> ORGANISM: Homo sapiens

<400> SEQUENCE: 21

Val His Ile Tyr Gln Lys Asp Leu Phe Phe Thr Glu Thr Ser Asp Gly
1               5                   10                  15

Ser Pro Gly His Leu Asp Leu Val Glu Gly Ser Leu Leu Gln Gly Thr
                20                  25                  30

Glu Gly Ala Ile Lys
            35
```